United States Patent [19]

Ryan et al.

[11] Patent Number: 5,866,410
[45] Date of Patent: Feb. 2, 1999

[54] CLONING OF THE BIOSYNTHETIC PATHWAY FOR CHLORTETRACYCLINE AND TETRACYCLINE FORMATION AND COSMIDS USEFUL THEREIN

[75] Inventors: Michael J. Ryan, West Milford; Jason A. Lotvin, Union, both of N.J.; Nancy Strathy, Monsey, N.Y.; Susan E. Fantini, Ridgewood, N.J.

[73] Assignee: American Cyanamid Company, Madison, N.J.

[21] Appl. No.: 474,933

[22] Filed: Jun. 7, 1995

Related U.S. Application Data

[60] Division of Ser. No. 125,468, Sep. 22, 1993, Pat. No. 5,589,385, which is a continuation-in-part of Ser. No. 821,109, Jan. 15, 1992, abandoned, which is a continuation of Ser. No. 558,040, Jul. 26, 1990, abandoned, said Ser. No. 125,468, is a continuation-in-part of Ser. No. 821,419, Jan. 15, 1992, abandoned, which is a continuation of Ser. No. 558,039, Jul. 26, 1990, abandoned.

[51] Int. Cl.$^6$ ................................................. C12N 15/00
[52] U.S. Cl. .......................................................... 435/320.1
[58] Field of Search ........................ 435/6, 91.1, 172.1, 435/252.35, 320, 320.1; 536/27

[56] References Cited

U.S. PATENT DOCUMENTS 4,921,801  5/1990  Rao et al. ............................. 435/172.1
4,935,340  6/1990  Baltz et al. ................................. 935/6
4,992,371  2/1991  Wohllenben et al. ............... 435/172.3

FOREIGN PATENT DOCUMENTS 0 183 571  6/1986  European Pat. Off. .

OTHER PUBLICATIONS

Old, R.W. and Primrose, S.B. Principles of Gene Manipulation. Blackwell Scientific Publications, Oxford, 1985.

Sambrooke et al. Molecular cloning. A laboratory Manual. pgs. 3.5 and 3.6 Cold Spring Harbor Laboratory Press 1989.

Reynes wt al. 1988 J. Gen Micro. 134 p. 585–598.

Butler et al. 1989 Mol. Gen Genet 215 p. 231–238.

Stanzak et al. Bio/Technology Vol. 4 p. 229–232.

*Primary Examiner*—James Ketter
*Assistant Examiner*—Irem Yucel
*Attorney, Agent, or Firm*—Anne M. Rosenblum

[57] ABSTRACT

The present invention describes a purified and isolated nucleic acid molecule which encodes for the biosynthetic pathway of tetracycline, chlortetracycline or an analogue thereof. The invention relates to the isolation and cloning of the nucleic acid molecule in an isolated fragment from *Streptomyces aureofaciens* and the expression of the biosynthetic gene in a heterologous host such as *Streptomyces lividans*.

1 Claim, 16 Drawing Sheets

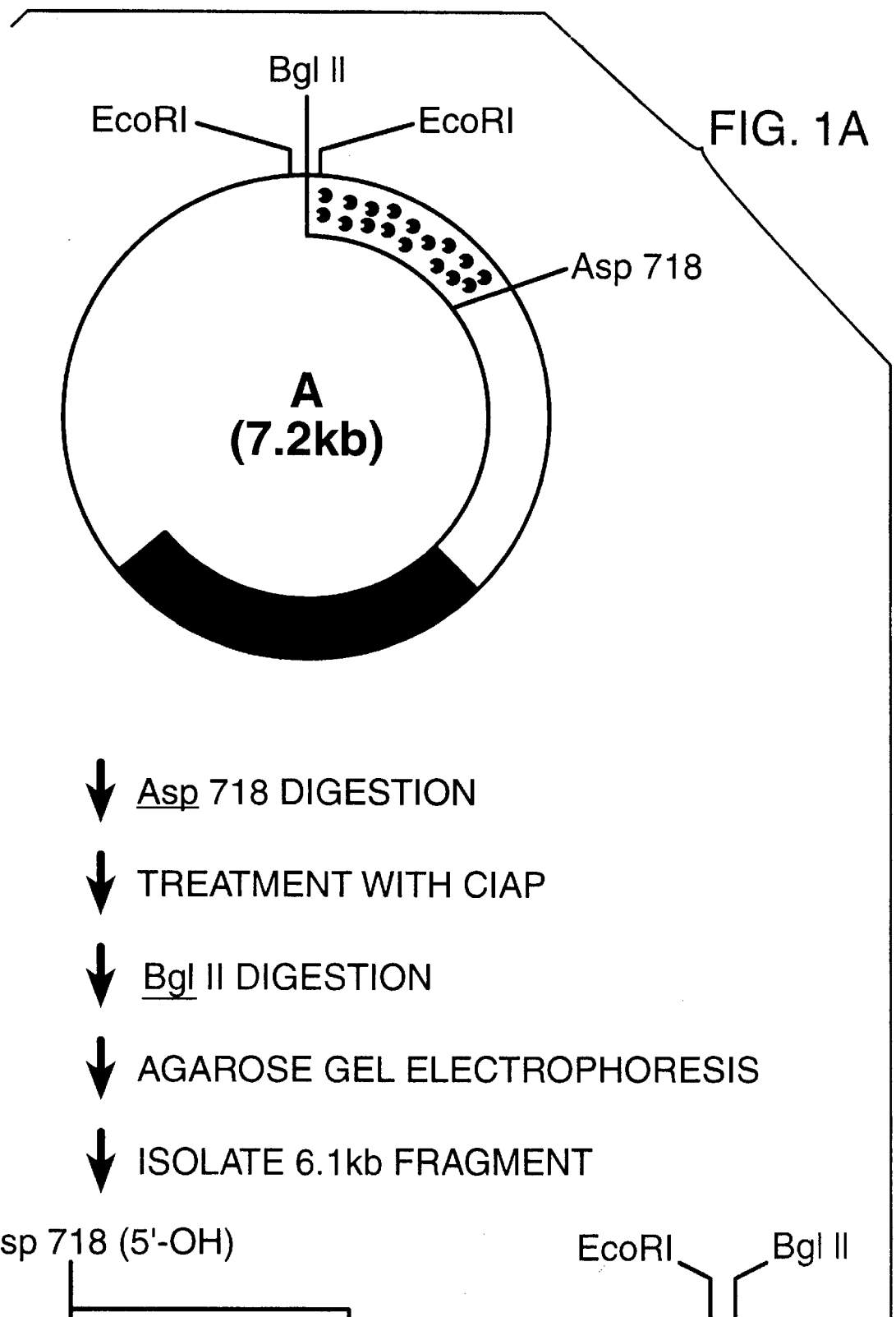

FIG. 4A

| | | | | | |
|---|---|---|---|---|---|
| GATCGGCCGA | CGGCTCCAGG | ACAGCCCGGG | CCGTCCCGGC | CCCCGCGGCA | 50 |
| CGGCCCACCC | CGCAGCGACC | CCGGCCCGGC | CGCTCCACGG | CCCGCTCCCG | 100 |
| GCCCGCACAC | CTTCCGGGCC | CCACTCCGAA | GAATCGGTTC | TCTTGGGCCC | 150 |
| GTCACCGGGC | CCGGGGCGTC | CACCGCACCG | CCCGCCGCGG | CCAGCCCGGA | 200 |
| TCGCTCCACT | CATCGGTCAC | TCGCGCCTGT | CGCCATCGGG | GGTCAACCGT | 250 |
| GTCAGTCGGC | AACAACCATC | CGTCGGTTCT | CGTCGTCGAG | GACAACGTCC | 300 |
| TGCTGCGCAC | GGGCCTGCAG | GCCCTGCTGT | CGGCCGAGCC | CGACCTCGTC | 350 |
| CTCCGCGCCG | CCGTCGGCGG | CGTGGACGAA | GCACTCGCCG | TCATGGCCGG | 400 |
| GCACCCCGTG | GACGTCGTGG | TGTACGGAGC | GGGCGAGTCG | GTGGCCGACA | 450 |
| CCGAGCGGGG | CCTCGAGCGC | CTGCTCGACC | GGGGCACCCG | GGTGGTCGTA | 500 |
| CTGAGCCGGC | GGGACCACCC | CGGCGAGATG | GAGACGTACC | TCAGCAGCGG | 550 |
| TGTGCACGCC | TACCTGGCAG | AGGACGCGGC | CGGGGAGTGC | CTCGGCTCGG | 600 |
| TGATCCGGGG | CCTGACCTCG | GACCGGGAGC | GGGTCTACAT | CATGGCCTCG | 650 |
| CGCTCCGGCC | TCGACTGGAT | GGCCGGCCAG | CGCGGCAACC | GCCTGTCCGG | 700 |
| ACGCGAGCGG | GAGGTCATGG | GCCTGGTCGC | GAACGGGCTG | AGCAACTCGG | 750 |
| CCATCGCGGG | CCGGCTCTGC | ATCTCGCCCG | GCACCGTCAA | GCGCCATCTC | 800 |
| CGGAACGTGT | TCGTCAAGCT | CAACGCCGTC | TCCCGGATCG | ACGCCGTGAA | 850 |
| CAAGGCCCGG | GCCGCTTCCA | TGCTGGTCCC | GGCCGGCCGG | GCCTGAGCCC | 900 |
| CGCGGACCGG | TCCGGCGCGG | ATCCGTCCGC | GGTGGACCGG | TCCGGCGCGG | 950 |
| ACCCTGCGG | GGACGACGGC | CCGGCAGGGA | GCGGAGCAGG | GCTCGGCCGG | 1000 |
| GACGGGCCTC | AGGCCGAACG | GGCCCGCAGG | CCCTGCTCCA | TCGCCCGCGC | 1050 |
| GGCAAGCGCC | TGGAACTCCT | GCCGAGTGGG | CGACGTGCCG | CTGAGCAGGT | 1100 |
| CGTTGTGCAG | CTCCTGCAGC | GGTCGGGAGG | GGGCGATGCC | GAGGTCCTCG | 1150 |
| TCGAGCCGGC | GGTAGAGCAC | GCGGTAGACG | TGCAGGGCCT | CGCTCCGCCG | 1200 |
| CCCGGCGCGT | CCCAGGGCGA | GCATGAGCTG | CTCGTGGTAC | CACTCGTTCA | 1250 |
| TCGGCTGGTG | CAGGGTCAAC | AGTCTGAGTT | CGGGGATGAG | TTCCCGGTGG | 1300 |
| CGCCCGAGCT | GCCGGTCGGC | CAGGATGCGG | TGCTCCAGGG | CGCGCAGGCG | 1350 |
| CATCTCCTCC | AGGACGGCGA | CGTGACCGGC | GAGCGGAGCA | CCCCACCGGG | 1400 |
| ATGTCCGCCA | GGCGGTGCCC | CGCCACAGGT | CCAGCGCCTG | CCGCAGCCGC | 1450 |
| TGGGCGGCCG | CCTCGGGGTG | GCCGGCGGCC | AGCAGCCGGT | CCCCCTCGTG | 1500 |
| GTGCAGCCGC | TCGAACTCCT | GGGCGTCCAG | CTCCTCCTCC | CCCAGCAGCA | 1550 |
| GCACGTAGCC | GGGGGCCTTG | GTGAGGATGA | CCTCGCGGCC | CAGCGGACGG | 1600 |
| CAGAGCTTGC | GCAGTTGGTA | GATGTACGTC | TGCGCGGTGG | TGACCACCGT | 1650 |
| GCGTGGCGGG | CTGCTGCCCC | AGATCTCCTC | GATGATGAGG | CCGAGGTCCA | 1700 |
| CGATCCGGTT | CGCGTTCATG | AGCAGGACCG | CCAGCGTCCA | GCGGACCTTC | 1750 |
| AGCGCGCTCG | GGGTACACGG | AATTCCCTTG | TCGAGGACTT | CCAGCGGACC | 1800 |
| CAGAATGTTG | AACTTCACCA | TGCCTCCGAT | GTCGCTCGGA | TTCCCTCGGC | 1850 |
| CCCAGGTATA | TCCGGGTCCG | CGGACGGGTC | TCAAGAGGAA | TCCGCACAAG | 1900 |
| GTGGCAGGCG | CGCAATTCCA | AGGTGGCACC | GACGCATTTC | CAGAGCGGTC | 1950 |
| CGGCTCCCTG | TCCCGAGGGA | AACACCCCG | CCGACCGACC | CCCGCCGATC | 2000 |
| GGCTGGCGGA | TCGACAAGTC | CTGTTAGGGT | GGGGGCGGTT | GGCCCCATGG | 2050 |
| GCCGGGCACC | AGTCACCTGA | TACCCGCGAG | ACAGAGCCAC | GAGGAGAAGG | 2100 |
| ACGTGCCCCC | GAAAGATCCG | TGTTGCTCCG | GTAATCCGTA | CGAAGACCGC | 2150 |
| AGAACTAGGG | GACACACGTC | TTGACAACCG | TGAACATCGG | AATCCTGGCC | 2200 |
| CATGTCGACG | CCGGTAAGAC | CAGCCTGACC | GAGCGACTGC | TGCACACCGC | 2250 |
| CGGCGTCATC | GACCGGGTCG | GCAGCGTCGA | CCGCGGCGAC | ACCCAGACCG | 2300 |
| ACTCGCACGA | ACTCGAGCGC | CAGCGCGGCA | TCACCATCCG | GTCCGCGGTG | 2350 |
| GTGTCCTTCA | CCGTGGGCGA | CGTCAAGGTC | AACCTCATCG | ACACCCCGG | 2400 |
| CCACCCGGAC | TTCATCTCCG | AGGTGGAACG | GGCCCTCGGC | GTGCTCGACG | 2450 |
| GCGTGGTGCT | GGTCATCTCC | GCCGTGGAGG | GCGTACAGGC | CCAGACCCGG | 2500 |
| CTGCTGATGC | GCACGCTGGT | GAAACTGCGC | ATGCCGGTCA | TCCTCTTCGT | 2550 |

FIG. 4B

```
CAACAAGATC GACAGGATGG GCGCGCGCTA CCACGAGCTC CTGGACGAGA      2600
TCCGCTCCGA GCTCACCCCG GCCGTCGTCG CCCTGACCCG GGTCGAAGGG      2650
CCGGGCACCC CCGGAGCACG GGCGTTCGCC CGGACCGTCG GGACCGACGA      2700
CCCCGACTTC GCCGCCGAAC TGGCCGACGT CCTGGCCGAG CACGGCGACG      2750
ACTTCCTGGC CCGCTACCTC GAGGACGAGA CCTCCCTGAC CGCGCAGGAC      2800
TACAGCGCGG AACTCGCCCG CCAGGCGGCC CGGGCCCAGC TCTACCCGGT      2850
GCTCTTCGGC TCGGCCGTGG CCGGCGCCGG CATCGATGCC CTGGTCGACG      2900
GGATCACCAG GCTGTTTCCG GTCAATCACG GCGGCTCCGG GGGCACCCTC      2950
CGCGGTACCG TGTTCAAGAT CGAGCGCGGG TGGGCGGGCG AGAAGGTCGC      3000
CTACGTCCGG TTGCACGGGG GCGAGCTCGG GTCGCGGGAG AAGGTGTCCG      3050
TGTTCCGGCG CGACCAGCAC GGAGCCGTCA CCGAGATTCC CGGCCGCACC      3100
ACGGTGGTCG AGGTGTTCGA CCGGGGCTCG GCCGTCGTCG AGTCGCGGGC      3150
CCGGGCCGGG GACATCGCCA AGGTCTGGGG GCTCAAGGGC ATCCGGATCG      3200
GCGACCGGCT CGGTTCGGCC GAGGGGCTGG ACGGGGAGCA CCTGTTCGCG      3250
CCGCCGAGCC TGGAGACCGT GATCCGACCC TCCCGGCCCA GCGCGATGCC      3300
CGAACTGTAC GACGCGCTGC TGCAGTTGGC CGACCAGCAC CCGTTCATCA      3350
ACGTCCGCAA GGACGACGAG GAGCAGGAGA TCGCCGTCTC GCTCTACGGT      3400
GAGGTGCAGA AGGAGGTCAT CGCGGCCACG CTCGCCGACG AGTTCAAGCT      3450
GGACGTGGCC TTCGAGGGCA CCCGGATCAT CTGTGTCGAG CGCCCGATCG      3500
GGGTCGGCGA GTCGGTGGAG GAGATCGACT ACCGGAGCAA GACCTTCTTC      3550
TGGGCCACGA TCGGCCTGCG GGTGGAACCC GGGGAGCCGG GATCAGGGGT      3600
CGTGTTCCGC CGCTCGGTGG AGCTCGGCTC GCTGCCGCAC GCATTCCACA      3650
AGGCCGTCGA GGAGGCCGTG CGGGCCACCC TGCAGCAGGG GCTGAACGGC      3700
TGGGAGGTGC TGGACATCCT GGTGACCCTC ACCCGTTCCG GGTTCGCCAG      3750
CCCGGTGAGC GCGGCGGGCG ACTTCCGCAA GCTCACGCCG CTCGTGCTGA      3800
TGAACGCGCT CAAGCAGGCG GGCACGCAGG TGTACGAACC GGTCAACCGC      3850
TTCGAGCTGG AGGTGCCGGG TGAGAACGCC AGCGCCGCCC TGCTGAGCCT      3900
GGTGGAGTGC GGCGCCACCC CGGAGAGCAC CCGGGGCCTG GCAGCAGCT       3950
GCCTGGTGGA GGGGACGATC CCGGCCCGCA CGGTGCAGGA GTTCGAGCAG      4000
CGGCTGCCGG GCCTGAGCCA GGGCCAGGGC GTGCTGGTCA CCCGGTTCCA      4050
CAGCTTCCAG CCGGTGGTCG GGGCGGCGCC GAGGCGGCGG CGGACCGACC      4100
TCAACCCGGT GGACCGCTCG GAGTACATGC TGCGGGCCTT CGGCGGGATC      4150
TGACGGGACG TCGCGAAAGT GAGGGCCCGA CCACCGTGAC GGTGGTCGGG      4200
CCCTCAGCCG TGGCGCACTC CGTCCTCAGT CGAGCAGTGC CACCGCTCGC      4250
GTCCAACCCG CCCCCGCCCC GGCGATCTTG ACCGGGAACG CCTGCACGGT      4300
GAACCCGGTC GGCGCGGGCA GTGCGCCCAG ATTGCTCAGA CGCTCGATCT      4350
GGCAGTACTC CCGCTGCCGC CGCGAAATGC GCGGGCCACA GCACGGAACG      4400
GTCGCGGGTG CGCTGGAACT CGGCGAGCAT GTGCGTGAAC GGAGCGTCCA      4450
GCCCGAAGCG TCCGTCCCGA TGAGCCGCAC GCCGAGGTCG AGCAGAAGGT      4500
TCGTCGCCGC CCCGTCCAGG CCCGCGAACC GGGTGAAGTA CTCGGGAGTC      4550
CCGGCGAGTC GTTCGGCACC GGTGTGCAGC AGCACGATCT CCCCGGCGCT      4600
CGGCCGGTGG TCGATCTCGT CGAAGGCGCG CCGCAGCCGG TCCACGCCGA      4650
CCGTCCCGAC CCCGCAGTCG GTGAGGTCCA GCCGGACGCC CGGCCCGATG      4700
AACCATTCCA GCGGCAACTC GTCGATGTGG CGCGGCACTC CGTAGGCGGC      4750
CCTGCTGCCG TAGTGGGAGG GTGCGTCGAC GTGCGTGCCG GTGTGGGTGG      4800
TCAGGGTCAG GGTGTCCAGC GAGAGCAGTT CCCCGTCCGG CAGGTCCGCG      4850
ACGTCGAACT CGAGGCCGTG GTCACGGAGC ATGCCCTCGG CCATGTGGCG      4900
CGCGCCGTCG GCCGGCGTCA GCACCTCGTG GCGGATGCCG TCCACCTCCC      4950
AGGCGTTGGC GTCGATCGTC GAGGAGAGGT CAATGAGGCG CATGCGCGGC      5000
TCCTTCCGGC AGCAGGGCGC AGTCCCGCAG GACGTCGAGG CAGCGCTCCG      5050
GCCCCGATC CCGCGCGGCG AGGTGGCCGT CCGGCCGGAT CAGCAGGAAC       5100
```

FIG. 4C

```
TCCCCTGGTG CCAGGCCGAG TTCGCGGCGC AGAATACCCC CGGGGTCGGG    5150
CAGCTCGCCC GGGGCTCCGG GGTCGGCGAC GGTACGGACG GAGACGGCGG    5200
AGCCGAACAG CCGCTCCACC CGGGCGAGCG CCTCCCGGTG CCCGGTGCTC    5250
CCGCCCTCGG CCGGGGTGGC GAGCAGGGTC CAGCGGGGGT CGGCGAGTTC    5300
GGCGCAGAGC GCGGACCAGC CGGGGTGCCC GGCGGCCGTC CGGGCGTCGC    5350
AGCCCACCCG GTCCCCGGGG GAGGGCCGCC CGGCGCGCGA GCCGGCCGGG    5400
CGGGTGAGCG GGCTGTCCGG GTAGCCGAGG GCCAGTCCGC AGAAGCCCCG    5450
GATCATCCGG CCCTCGACCT TGCGCCGCAG CGGCGTGATC CGGCGCAGCG    5500
CCGCGGTGCC CACGGTCAGC AGGGCCGGGG CCAGCGCGGT GCGCAGCGAC    5550
ACCAGGGCGG TGGCCGTGCG GGTGGAGCGC AGCAGCACGG CCCCGGTCGG    5600
GACGCGCTCG GCGTCGTAGC TGTCCAGCAG GGCGGGCCCG GCGTGGCCGC    5650
GGATCACGTC GGCGAGCTTC CAGGCGAGGT TGTAGGCGTC CTGGATACCG    5700
CTGTTCATGC CCTGCCCGGA GGCCGGGCTG TGGACGTGGG CGGCATCCCC    5750
GGCGAGGAAG CAGCGGCCCT CGCGCATCCG GGTGATCTGG CGTTGCTGGA    5800
CGGTGAAGAC GGAGAGCCAG GTCGGGGTGC CGACCTGACG GGGCGCCCGA    5850
GCGCCCGGCC CGATCTTGTC GGCCAGGCGG CGGCGGACCA GCTCGCGGTC    5900
CTCGGCGCCG TCGGTGTCCA CCGTGTCCAC CACGCGCCAC TTGCCGGGCT    5950
CGGGGAACGG GACGAGCAGC AGGGTGCCGG GCTCGGTGTG CAGCAGGTGG    6000
TTGCTGTCCG GCGGGAGGTC GGCGTCGAGG GTGACGTCGG CGTTGAGCCA    6050
GACCTCGGTG GAGTCGCCGA TCAGGCGCAT CCCGAGCTGC TTGCGCACGG    6100
TGCTGCGGCC GCCGTCGGCG CCGACCAGCC AGGGCACCCG GGTCTCCTCG    6150
GTGCGCCCGT CGGCGTGGCG GAGGGTGACG AGCACGGAGT CGGGCCCGGG    6200
CTGCAGCGCG GCGAGTTCGA CGCCCATTC CACGGGGACG CCGAGTTCGG    6250
CGGTGCGCTC GCGCAGCACC TGCTCGGTGA CCACCTGGTC GACCATCAGG    6300
CTGAACGGGT AACGGGTCGG CAGTGAGCGG TAGTTGGTGT CGAAGCGGAT    6350
GAGGGTGCGG CCCCGGCGGT GCATGGTGAA GTGGGTGACC CGCCGGCCGA    6400
GCGGCAGCAG CCGGTCGAGG GCGCCCATCT GCTCGAGCAC CTCCATGGTC    6450
CGGGCGTGCA CCGCCAGGGC CCGGCTGCTG GTGGCCGGGG CCGGGCGCGG    6500
CGTCGACCAG CCGGACGGGA ACGCCCCGCG CCTGGCGAGT TCGTGGGCCG    6550
CGGTGAGGCC GACCGGGCCG GCCCCGCGA TCAGGACGGC CGGAGCGGGG    6600
TCAGCCACGG CGTTCCTCGG CGAAGCGCTT GGCCAGGCCG AGCGTGGCGC    6650
GGCTGTTGCC GCCGGCGGCC TCGCGGATGA AGCGGCGGGC GGTGGCGGCG    6700
GTGGCGTCCG GGCCGAGGAC GGTGGGGACC GCCTCGGGGT TGAGGACGAC    6750
GGCGTGCCAG GAGGTGACCC GCACTCCGCG GTCGGTCGAC TCGACGGTCC    6800
AACGGCCGGT GTGGGCGGCC ATCATGGAGG GGGTGCGCAG CTGCTTGTAG    6850
GCGATGCCGG ACTCCGGGAA GCAGATCCGG ATGGACTCGG TGGTGTGTTC    6900
GGAGCCGTCG GCGGTGCGGG TGTCCATGGA CATGTGCTGG ATGCCGCCGG    6950
CCTCCTCGCG CAGGTCGAGG CGGGCGACGT GGGGCAGCCG GCGGGCCAG    7000
GCGGCGGCGT CCCGCAGGAA GTCGTAGACG GCCTCCGGGG CGGCGTCGAC    7050
CAGCACCGAG TCCTCGAACT CGAACTCGAA CTCGGCGAGC CGGTTCCAGC    7100
GTTCGGCGAG GTCCTTGATG CCGGCGAGCT CGCTGCGGCT GTTGCGGTCC    7150
GTCGCCTCGC TGATCCAGCG CAGGCCCTGC GGGTCGTCGT CGAGCGCGCT    7200
GAACTCGTGG GTGAGGGTGA GGTGGTGCC GCCGGGCGC TCGGCGACCT    7250
GCCACTCCCC CGCCATCGAG GCGACCGGGG CCGAGGAGGC CTCCTGGCGG    7300
AAGCGGATCC GGCGCAGGTC GGCGTCCAGG TCTCGGCGGG ACGTCCAGTG    7350
CTTGACCTCG CCGTTGGCCC GGGCCCAGAT CCGCAGGCGC TCGGCGCCCG    7400
GCCCCAGCTC CTCGCGCTCG ACGTGGAGGG TGGGGCGAA GCGCCGCGGC    7450
CAGGCCAGGG CGTCGGCGAT GACGGTGTAG ACGACCTCGG CGGGGGCGTC    7500
GACGTCGATC GAGTGGGTGG TGTGCTGGAT GGTGCTCATG GGTGGGACCG    7550
GCCCTTTCCG TCGGCGGGGT GAAGTTCGGC GGGGTGCGTG GGGTGCGGCT    7600
CAGTAGATGC CGAGGCCACC GCAGACGTTG ATCGCCTGCG CGGTGACCGA    7650
```

FIG. 4D

```
CGCGGCGTCG GGGGTGGTCA GGTAGTCGAC CATGCCGGCG ACCTCCTCCG    7700
CGGTGGAGTA GCGGCCGAGC GGGATCTTCT GCTCGAAGCG CGAGAGCACG    7750
TCCTCCTCGG TGGTCGCCCA GGTCGCGGCG TACGCCTGGC GGACCCGCAC    7800
GGCCATCGGC GTCTCGACGT AGCCGGGGCA GACGGCGTTG ACCGTGGTGC    7850
CGGTGTGGGC GAGTTCCTTG CCAGCGCCT TGGTGAAGCC GATGACGCCG    7900
GCCTTGGAGG CCGAGTAGGG GGCGCCCAGC GGGACACCCT GCTTGCCGCC    7950
GGTGGAGGCG ACGCTGATGA TCCGCCCGTG CCCGGCCGCC TCCATGCCGC    8000
CGGTGGTGAG GACCTCGCGG GTGACGCGGA AGACGCTGGT GAGGTTGGTG    8050
TCGATCACGT CCTGCCACAG CTCGTCGGTG AGGGTGGAGG TGACGCCACC    8100
GCCGTTGCGT CCGGCGTTGT TGACCAGCAC GCCGATCGCG CCGAAGCGGT    8150
CCACCGCCGC CCGGACGAGC CTGCTCACGT CCGGCGCGGA GCGGACGTCG    8200
GCCGCGAGGC CGTCCACCTC CAGGCCCTCG CCGCGCAGGC GGGCGACCGT    8250
CTCGGCGACG CCCTGCGCGG TGCGGGCGCA GATGAAGACG CTCAGCCCGC    8300
GCCGGGCCAG CCGCTCGGCG CTGGCCAGTC CGATGCCGCT GGTCGCCCCG    8350
GTCACCAGGG CGACGTCGCC GGTCGTCACG GTGCTCATCG CATCGATCTC    8400
CTGTCTCGCT CACGGATCGC GGGCCCGGCG GGCCCGCCGG TCGGGCCCG    8450
CCCCCGCGCC CCGTCGGGAA CCCGGGGGA CAGGCCCCGG GCCGACCCTG    8500
CCCGGACGGC TTCGACTGCG GTTCGAGCGC GCCGCACACG CCGACCGCTC    8550
CAACGGGATT CGAAGCGCGG GTGGGAGCGT CGGCGCTGCC CAACCACCGA    8600
CGCAACGAGG AGGCCCGGAG CATGACCGGT TCGCTCTACG AGGAGGTCCA    8650
GCACTTCTAC GGGCGGCAGA TGCGCCACCT GGACGAGGGT GAGGTCACCG    8700
AGTGGGCCGC GACCTTCACC GAGGACGGCG TGTTCGCCGC CAACGCCCGC    8750
CCGCACCCGC AGGAGGGGCG CGCGGCGATC GAGCAGGGCG CCCGGGAAGC    8800
CGCGCAGCGC CTGGCCGATG CCGGAATCCG GCACCGGCAC TGGCTGGGGA    8850
TGCTGGAGGT CGCCGCGCAG CCGGACGGCC TGGTGCTCGC CAAGACCTAC    8900
GCGCTGATCG TCGCGACGCC CAAGGGCGGG CCGGCCGCCG TGCACCTGAG    8950
CTGCAGCTGT GAGGACCAGC TGGTGCGCGT CGACGGCGAG TTGAAGGTCC    9000
GGCACCGCCG GGTGCACCGG GACGACCTGC CCGCCTGAGA GGAGGCCACC    9050
GTGGACCTCC CACGGGACAG TACGACCTTC GGTCCGCCGC TGGACGTGGT    9100
GGCGGAGCTG ATCGGCGGGC CCCGGATCGA CGACCTCGTC CGTCGCGCGG    9150
CTGAGCTGAC GCCTCGTCAT GTAGCTCTGG TGCACGGTGA CCTGGTGCTC    9200
GACCACGCCG CGCTGGAGGC CCGGGTGAGC GACTGCGCCG AGGCGCTGCG    9250
CGCCGCGTTC GGCGGTCCCG GCACGGTCAT CGCGATCGCC GCCGAACTGA    9300
CCGTCGACTT CGCCGTCACC TTCCTGGGCA TCTCCCGCTC CGGGAACACC    9350
AGCGCCATGT TCAACCCGCT CGTCCCGGAC GACACCCTGG TGCACGTCCT    9400
GAACTCCTGC GGCGCCCGGG CGGCCGTGCT GTCGCCCCGG ATGCACCGCC    9450
GTGTCCTGGC CCTGCGGGAC CGGCTGCCGC TGCTGCGGCA ACTGGTGGTG    9500
ACCGCCGACG CGCTCGACGG CACGCCCGTC CTGGACGCCC TGGAGCGCAC    9550
CGCCGTCCCG GCCGGCGAGG TGGTGGAGAC CGCCTGCCTG CAGTTCACCA    9600
GCGGCACCAC CGGCGCGCCG AAGACCGTCC GGCTCAGCCA CCGCAACCTG    9650
CTGGTGAACG CGGCGCAGTC GGCGCACGCC CACCGGCTGA CGGCCGACGC    9700
CGTCTCGCTC AACAACCTGC CCTCCTTCCA CCTGATGCAC CTGAACACCG    9750
CGCTCGCGGT CGGCGCGACG CACGTGCTCT GCCCGGAGGA GGACCGCGCG    9800
GCGCTGGTGG GACTGGCCCG TACCTGGCGG GCCTCGCACC TGTACAGCCT    9850
GCCGGTGCGG TTGTCCCGGC TCGCCGGGGA CGAGCGGCTG CCCGGCTTCC    9900
GCATCCCCTC GCTACGGGCG GTGCTGTCCG GTGGATCGGC GCTGCCGCCC    9950
CGGACGACGA CCGCCCTGCA GGAGCACTTC GGGGTGCCGG TCGTCCAGGG   10000
CTACGGCCTC GCCGAGACGT CCCCGTCGAC GCACTTCGAC CTGCCCGAGG   10050
GGCCCACCCT CGGCTCCAGT GGGCCCCGG TCGCCGGGAC GGCCTGCCGG   10100
ATCGTGGACG TGCGCACCGG CGCGGTGCTG CCGGTGGGCG AGCGCGGTGA   10150
GATCCAGGTC CGGGGCCCGC AGTTGATGCT GGGCTACCTG GGCGACGGGC   10200
```

FIG. 4E

| | | | | | |
|---|---|---|---|---|---|
| CCACCGACGC | CGTCGACGCG | GACGGCTGGT | TCCGCACCGG | TGACGTCGGC | 10250 |
| CGGATCGACG | AGGCCGGCCG | CCTGTTCGTC | GTCGACCGGA | TCAAGGACGT | 10300 |
| CTTCAAGTGC | GACAACTGGC | TGGTGTCGCC | GACCGAGATC | GAGCGGGTGC | 10350 |
| TGATGCGGCA | CCCGGCCGTC | GCCGACTGTG | TGGTCTTCGA | CCAGCCCGAC | 10400 |
| GAGCTGAGCG | GCGCCGTCGC | CGTCGGCCTC | GTCGTGCCGC | GCGGCGAGGG | 10450 |
| CGTCGACCCG | GCCGCCCTGG | CCGCGTTCGC | GAACGCCCGG | CTCCCCTACT | 10500 |
| ACGAGCACCT | GAAGCAGCTG | CGCCTGGTGG | AGGGCATCCC | GCGCTCCGCC | 10550 |
| ACGGGCAAGG | TCCAGCGGCG | CGAGCTCCGT | GACCGGCTGT | TCGGCTCCCT | 10600 |
| CTGACCCGCA | CCACCCCACC | CGTCCGACCC | ACCACAGGAG | GAACACCGTG | 10650 |
| TACACCTTCA | TCAACCGTTT | CACCGTCACC | GGGGACGTCG | CCGAGTTCGA | 10700 |
| GACGCTCGTC | GGCGAGATCA | GCGAGTTCAT | GAGCGGCCGG | CCCGGCTTCC | 10750 |
| GCTCGCACCG | GCTGTACCGC | TGCGCCACGG | ACGCCTCGGT | GTACGTGGAG | 10800 |
| ACCGCCGAGT | GGGACGACGC | GGCCTCGCAC | CGGGCGGCGA | CCGGCTCGCC | 10850 |
| GGAGTTCCGC | GCCCGGGTCG | GCAAGGTGAT | GAGCCTGGCC | AAGGCCGAGC | 10900 |
| CGGCCCCGTT | CGACCTGCTC | GCGCAGCACG | GCGCCTGAGA | GGGGGAGCAC | 10950 |
| CATGACGGAC | AACGGCGAGA | TCATTGCGCA | GCCGGTGATC | CAGCTGCGCG | 11000 |
| AGCTGGGGCT | GGCGGCGGCC | GGCGCCGCCG | CCGTGCGGGC | CGCGGCCCGG | 11050 |
| CTGGGCCTGG | CTGACGCCCT | GGGCGAGGAG | CCCGCCGGCG | CGGCCGAGCT | 11100 |
| GGCCCGGGCC | GTGAACGCGG | ACCCGGACAC | CCTGCAGCGG | CTGCTGCGCG | 11150 |
| CCCTGGCCTG | CTACGGCGTG | TTCGCCGAGC | AGCCGGACGG | TCGGTACGTG | 11200 |
| CACACCGGCG | CCTCCCGGCT | GCTGCGCGAG | GACACCCCGC | GCAGCCTGAA | 11250 |
| GGACATGGTG | CTCTGGGGCA | CCGAGCCGTG | GACCTGGGAG | CTGTGGGGCC | 11300 |
| ACCTCGACGA | GGCGGTGCGC | ACCGGCAAGG | CCGTCTTCCC | CGAGCTGCAC | 11350 |
| GGCATGGACT | TCTTCGACCA | CCTGCACGCC | CACTCCCCCG | AGTCGGCGGC | 11400 |
| CGTGTTCGAC | CGGGCGATGA | CCCAGTCCAG | CCGGCTCTCC | GCGCTCGCGT | 11450 |
| TGGCCGACCG | GCTGGACCTC | GGCGGGGTCG | GCACGGTGGT | GGACATCGCC | 11500 |
| GGTGGCCAGG | GGCACGTGCT | GGCCACCCTG | CTGGAGCGCA | ACCCCGGTCT | 11550 |
| GCGCGGCACC | CTGCTGGACC | TGCCCGAGGT | CGTCTCCGGG | GCCGACGCCC | 11600 |
| GGCTGCGGCC | GGGCGGTGCG | CTGGCCGGGC | GCGCCACGCT | GCTCGGCGGC | 11650 |
| GACTGCCGGC | GGGAGATCCC | GGTGCAGGCC | GACGTCTACC | TGCTGAAGAA | 11700 |
| CATCCTGGAG | TGGGACGACG | AGAGCACCGT | CCTGACGCTG | CGCAACGTCG | 11750 |
| TCCGGGCGGC | TGCTCCGGGC | AGCCGGGTGA | TCGTGGTCGA | GAACCTGGTG | 11800 |
| GACGGCAGCC | CCGAGCTGCG | GTTCACCACG | GCGATGGACC | TCCTGCTGCT | 11850 |
| GCTCAACGTC | GGCGGCCGCA | AGCACACCAG | GGCCGGCCTG | GTCTCGCTGA | 11900 |
| TCGAGGAGGC | GGGCCTGACC | CGGGCCGAGG | TCCGTCCGGT | CAACTCCTAC | 11950 |
| CTGCACCTGG | TGGAGAGCGT | GGTGCCCGAA | CGGGGCTGAC | CCGCCCGCCC | 12000 |
| ACGGCCGCCG | CCCCCGGACC | CGTCCGGGGG | CGGCGGCCGT | GCTGGTCCGG | 12050 |
| GGGCGGCGGC | CCTCGCACTG | TCCGGGGGCG | GCGGTGAGCC | CTCGGCACGG | 12100 |
| CCGACGGGGC | TCGGGGGGGC | GGAACGGGAA | GGGGAGCGGG | GTCAGATGCC | 12150 |
| CTCGGCGAGC | CGCTTCACCG | CCTGCTCGAC | CCGCTCGTCG | GTCTCGGTGA | 12200 |
| CGGCCACCCG | CACGTGCCGG | GCGGCCGCAG | CGCCGTAGAA | CTCACCGGGC | 12250 |
| GCCACCAGGA | TGCCGCGGTC | GGCCAGCGCA | CCGACGGTCG | TCCAGCACGG | 12300 |
| CTCGTCCCTG | GTCGCCAGA | GGAACAGCGC | ACCGGCCGAG | TGCTCGATCC | 12350 |
| GGAAGCCGGC | GTCCACCAGC | GCCCCGCGCA | GCAGCTCGCG | CCGCCGGGCG | 12400 |
| TAGCGCTGGC | GCTGGGCCGC | CAGGTGCGCG | TCGTCACCGA | GCGCGGCGAC | 12450 |
| CATGGCGGCC | TGCACCGGGG | CGGGGACCAT | GTGGCCGGCG | TGCTTGCGCA | 12500 |
| CCTCCAGCAG | CGTCGCGATG | ACGGCCGGGT | CGCCGGCGGC | GAAGCCCGCC | 12550 |
| CGGTAGCCGG | CCAGGTTGAA | GCGCTTGGAC | AGCGAGTGCA | CCGCCAGTAC | 12600 |
| GCCGTGGTGG | TCGCCGCCGG | TGACCTCGGC | GTGGAGCACC | GAGCGGGTCG | 12650 |
| AGCGCTCCCA | CACGTGGTCC | AGGTAGCACT | CGTCGTTGAC | CACCAGGGTG | 12700 |
| CCGCGCTCGC | GCGCCCACTC | GACGACCGCG | CGCAGTTCGG | CGGCGTCGAG | 12750 |

FIG. 4F

```
CACCCGGCCC TCCGGGTTGG ACGGGGAGTT CAGCCACAGC AGGCGCGGCG    12800
CGGGGCCGTC GTAGCTCAGC GGGTCGTCCG TCCGGACGAA GGTGGCACCG    12850
GCCAGTCGAG CGCTCACCTC GTAGGTGGGG AAGGACAGTT GGGGGGCAAG    12900
GACGACGTCC CCCGGGCCCA GGCCCAGCAT GGTGGGCAGC CAGGCGATCA    12950
GCTCCTTGGT GCCGACCGCC GGGATCACGG CCTCCGGCTC GACGCTCACG    13000
CCCTCGCGGC GCAGCAGCCA GGCCGCGGCG GCGGCCCGCA GCGCGGGCGT    13050
GCCCTCGGTG GACGGGTAGC CCGGGGCGTC GGCCGCGGCG GCCAGGGCCG    13100
CGCGCACGGC CTCCGGGGTC GGGTCGACCG GGTCACCGAG CGCCAGGTTG    13150
ACCAACCCGT CGGGGTGGGC GGCCGCGCGC CTGCGGTACG GAACAGAAC    13200
GTCCCAGGGG AACTTCGGCA GCCGCTCGAT CATGCCTGCG CCCCCGCCCC    13250
GACGTTGCGG GCCAGCGGCG GAGCCTGGCA GTCGGAGTCG ATGCCCCAGG    13300
AGACGATCCG CTCCGGCGTG ATCCGGATCA GCTCGTCGTC GACGTGCGGC    13350
AGGATCTCCT TGCCGCCGGT CGCCAGCGCG ACGGCGGTGC CCCGGATCTC    13400
GATCCCGCGG ACGACCCAGC GCTGCGCGTC CACGATGTCG TCCACCACCA    13450
GCGACACCCG CGGATGCCCC TGCACGTGGC GGTACTTGAG GCTGCGGGCC    13500
ATGCCGCGCC CGGTCACGTC GACGGTGCCG AGCTCGGCGT TGTAGTGGAA    13550
GCCCAGCGGG ACGACGTGCG GCTGTCCCCG GCCGTCCACG GTGGCCAGGC    13600
GGGCGAGCGG CTGCGAGGCC AGGTAGGCGG CCTCTTTCGC GGTGAATGGC    13650
ATGGCTGTCC TCGGTGTCTG CGGGTCAGGG TCGGCGCCCA CGCTAGGCAG    13700
CCTGCTTCGA GCGGCCTTGG TGCCGTTCGG CCTGCTCGCG TACCCGCGCT    13750
GGACTCCGGC TCGAAGTCCG GCTGACACGG TGAGGCCGTC GTACCGGACC    13800
GAGACGGGAG GTCGCGTTGG ACTGCGATGT GGTGGTGGCG GGAGCGGGC    13850
CGACGGGCCT GATGCTCGCC TGCGAACTGG CCCTGGGCGG AGCCCGGGCG    13900
GTGGTGGTGG AACGGCGCCG CGAGCCGGAG AAGCACTCCA AGGCCATGGG    13950
CATGCAGGGC CGCACCGTGG AACTGCTCGA ACTGCGCGGG CTGCTCGACC    14000
GCTTCAAGGA GGGCGCGGGC GTGCTGCAGG GCGGCAACTT CGCCAGCCTG    14050
GGCGTGCCGA TGCGCTTCGA GGAGTTCGAC ACCCGCCACC CGTACGTGCT    14100
GCTGGTGCCC CAACTGCGCA CCGAGGAGCT GCTCGCCGAA CGGGCCCGCG    14150
AACTGGGCGT GCGGATCGTG CGCGGCTCGG GCGTCACCGG CTTCGCCCAG    14200
GACGCCGACG GGGTCACCGT CGAGACGGAC ACGGGCCTGC TTCGGGCACG    14250
GTACCTGGTC GGCTGCGACG GCGGCGGCAG CACCGTCCGC AAGGCCGCCG    14300
GCATCGGCTT CACCGGACAG GACCCGCACA TGTACGCCCT CATCGGCGAC    14350
ATGCGCTTCA GCGGCGACCT GCCGCGCGGC GAGGGCCTCG GCCCAATGCG    14400
GCCGGTGGGC CTGGTCAACC CCGCCAAGCG GTCCTGGTTC GGCGCCTTCC    14450
AGCACCAGCC GGGCGTCTAC CGGGCCACCG TCGCCTGGTT CGACCGGCCC    14500
TTCGCCGACC GCCGCGCCCC GGTCACCGAG GAGGAGATGC GCGCCGCACT    14550
GGTCGAGCAC ACCGGCAGTG ACCACGGGAT GCACGACGTC ACCTGGCTGT    14600
CCCGCCTCAC CGACGTCTCC CGGCTGGCCG ACTCCTACCG GCTGGGCCGG    14650
GTGCTGCTGG CCGGCGACGC CGCGCACATC CACCTGCCGG CCGGCGGCCA    14700
GGGGCTCAAC CTGGGCTTCC AGGACGCCGT CAACCTCGGC TGGAAGCTGG    14750
CCGCCGTGGT CCGCGGCCAC GGCACCGAGG AGCTGCTGGA CAGCTACGGC    14800
CGCGAGCTGT CGCCCGATCG CCGACGGGTG GTGCGCAACA CCCGCACCCA    14850
GGCCGTCCTG ATCGACCCGG ACCGCGGTA CGAGGCACTG CGCCAGACCT    14900
TCCGCGACCT GATGGCGCTG CCCGACACCA ACCGCCACAT CGCCGGCATG    14950
CTCTCCGGCT TCGACGTCGC CTACGGCGGC GGCGACCACC CTCTGGTCGG    15000
CCGCCGGATG CCGGACGCCG AGCTGATCAC CGCGGACGGG CCGCGGAGGA    15050
TCAGCGATTG CTTCGCCGGG GCCCGCGGTC TGCTGCTGCT CCCCGAACAG    15100
GGCCCGACCG CCTCGCCGCT GGCCGCCTGG GCGGACCGCG TGGACACCCT    15150
GACCGTCAAG TCGGGCGGCC CGGACCCGGA CACCGCCCAC CTCGTCCGCC    15200
CGGACGGCTA CGTGGCCTGG GCCGGCGAAC CGGCCCGCAC CGAGGAACTG    15250
CACCACGCCG CGACCACCTG GTTCGGCGCG GCGGCCTGAT CCCCCTCCCC    15300
```

FIG. 4G

```
CTGAGAAAGG ACGCACGATG ACCTCGTCCA CCGACAGCGC CGCCGCCCGC    15350
GCGCGCCGGA TCGTCGCCCT CAACACCGCC TACTTCCAGG CGAAGGCGCT    15400
GCAGAGCGCG GTCGAGCTCG GCCTCTTCGA GCTGCTCGCC GAGCGCTCCG    15450
CCGGGCTCGA CCAGATCCGC GCCGAACTGG GCGTCCGGCA CCGGCTGTTC    15500
AAGGACTTCC TGAACGCCCT GGTCGGCCTC GGCCTGCTGG ACGAGCAGGA    15550
CGGCGGCTAC CGGGCCTCCG AGCTCGCCCG GGAGTTCCTG CTCCCCGGCC    15600
CCACGTACCT CGGCGGCACC GCCGCCAGC ACGCTCGGCT GCACTACCAC     15650
GCCTGGGCGC AGCTGACCGA CGCGCTGCGC GACGGCAAGG CCAAGTCGGC    15700
CGTGGCCGCG CAGGGCCAGC TGGCCTACCC CAAGCAGTAC GAGGACCTGG    15750
ACCGCGCCCG GCAGATCATG CTGCACATGG ACGCCCACAA CGGTTTCACG    15800
GCCGACGAGT TGGCGCGCGC GATCGACTGG AGCCGGTACA CCTCCTTCGT    15850
GGACGTCGGC GGCGGGCGCG GCAACGTCGC CTCCCGGATC GTCACCGCCC    15900
ACCCGCACCT GCGCGGCGGG GTCTTCGACC TGCCGGCGCT GCGCCCGCTC    15950
TTCGAGGAGC TGGTGGCCTC GGCCGGAACC GCCGACCGGG TGGACTTCCA    16000
CGGCGGTGAC TTCTTCGCCA CCGACCTGCC GGAGGCGGAC GTGGTGATCT    16050
TCGGTCACGC CTGCCGGACT GGGCCGGTCG GGACCGCAG GGAGCTGCTG     16100
CGCCGCGCCC ACAAGGCGGT GCGCCCGGGC GGCCTGGTGG TGCTGTACGA    16150
CGCCATGATC GACCCGGAGG AGCGCGACCC CGAGGTCCTG CTGCAGCGGA    16200
TCAACCACAC CATGATCCGG GACGAGGCCG GGCCTACTC GCTGCAGGAG     16250
GCCCGCGCCT ACCTGGAGGA GGCCGGCTTC ACCGTCGACC GGATCGCCGC    16300
CTCCGACACC ATCACCCGCG ACCACTTCGC CATCGGCGTC AAGTCGGTCT    16350
GAAGGAAAAG GAGTTCGACA TGACCGACAC AACCGCGGAT CAGACGCGGC    16400
ACGGCGACCG GCCGTACGAC GTCGTCATCA TCGGCAGCGG GCTGTCGGGC    16450
ACCATGCTCG GCTCGATCCT CGCCAAGCAC GGCTTCCGGA TCATGCTGCT    16500
GGACGGTGCC CACCACCCCC GCTTCGCCGT CGGCGAGTCC ACCATCGGGC    16550
AGACGCTGGT GGTGCTGCGG CTGATCTCGG ACCGGTACGG GGTGCCGGAG    16600
ATCGCCAACC TGGCGAGCTT CCAGGACGTC CTCGCCAACG TCAGCAGTTC    16650
GCACGGGCAG AAGAGCAACT TCGGCTTCAT GTTCCACCGG GACGGCGAGG    16700
AGCCGGACCC GAACGAGACC AGCCAGTTCC GCATCCCCTC GATCGTCGGC    16750
AACGCGGCCC ACTTCTTCCG CCAGGACACC GACTCCTACA TGTTCCACGC    16800
CGCGGTGCGC TACGGCTGCG ACGCCCGGCA GTACTACCGG GTGGAGAACA    16850
TCGAGTTCGA CGACGGCGGG GTGACCGTCT CCGGCGCGGA CGGCAGCACC    16900
GTCCGGGCCC GCTACCTGGT CGACGCCAGC GGCTTCCGCT CGCCGCTGGC    16950
ACGGCAGTTG GGGCTGCGGG AGGAGCCGAG CCGGCTCAAG CACCACGCCC    17000
GCTCGATCTT CACCCACATG GTCGGAGTGG ACGCGATCGA CGACCACGTG    17050
GACACGCCGG CCGAGCTTCG CCCGCCGGTG CCGTGGAACG ACGGGACGAT    17100
GCACCACATC TTCGAGCGCG GCTGGATGTG GATCATCCCG TTCAACAACC    17150
ACCCCGGGGC CACCAACCCG CTGTGCAGCG TCGGCATCCA GCTCGACGAG    17200
CGCCGCTACC CCGCCCGGCC GGACCTGACG CCCGAGGAGG AGTTCTGGTC    17250
CCACGTGGAC CGCTTCCCGG CGGTGCAGCG GCAGTTGAAG GGCGCCCGCA    17300
GCGTGCGCGA GTGGGTGCGA ACGGACCGCA TGCAGTACTC CTCGAGCCGG    17350
ACGGTCGGCG AGCGCTGGTG CCTGATGTCG CACGCGGCCG GCTTCATCGA    17400
CCCGCTCTTC TCCCGCGGCC TGTCCAACAC CTGCGAGATC ATCAACGCGC    17450
TGTCCTGGCG GCTGATGGCC GCGCTGCGCG AGGACGACTT CGCGGTCGAG    17500
CGCTTCGCCT ACGTGGAGGA ACTGGAGCAG GGCCTGCTGG ACTGGAACGA    17550
CAAGCTGGTC AACAACTCCT TCATCTCCTT CTCGCACTAC CCGCTGTGGA    17600
ACTCGGTCTT CCGGATCTGG GCCTCGGCCA GCGTGATCGG CGGCAAGCGC    17650
ATCCTCAACG CACTGACCAG GACCAAGGAG ACCGGCGACG ACAGCCACTG    17700
CCAGGCGCTG GACGACAACC CGTACCCGGG CCTGTGGTGT CCGCTGGACT    17750
TCTACAAGGA GGCCTTCGAC GAGCTCACCG AGCTGTGCGA GGCCGTGGAC    17800
GCCGGGGACA CCACGGCCGA GGAGGCCGCG CGGGTGCTGG AGCAGCGGGT    17850
```

FIG. 4H

| | | | | | |
|---|---|---|---|---|---|
| CCGCGAGTCG | GACTGGATGC | TGCCGGCCCT | GGGCTTCAAC | GACCCCGACA | 17900 |
| CCCACCACAT | CAACCCGACG | GCGGACAAGA | TGATCCGGAT | CGCGGAGTGG | 17950 |
| GCCACCGGTC | ACCACCGCCC | GGAGATCCGT | GAGCTGCTGG | CCGCCAGCGC | 18000 |
| CGAGGAGGTC | AGGGCGGCGA | TGCGGGTCAA | GCCGTAACAC | GAGGGGCAAC | 18050 |
| GGGCAGCAGC | GTCCGCGGGA | CGGCTGCTCC | CGGACGCGGG | CCTCGCCGTT | 18100 |
| CGCCGCACGC | GGGCGGGCTC | AGCCCTCGGC | CGCCAGGGTC | AGGGCGGCCG | 18150 |
| TCCGCGGATC | CTCCTCCACC | GGCCAGCGGG | CGTAGGAGCG | GCGCCAGTAC | 18200 |
| ATCAGCGGGC | TGGGCACCCT | CGGGCCGGGG | CCCGCCGGCC | CACCACCGCG | 18250 |
| CCGATCACGA | TGGTGTGGTC | GCCCGCTGTC | GAGGGCCGCG | GCCGACCCGG | 18300 |
| CACTCGGCGT | GCGCGACGAC | GTCGGCCGAC | AGTGACCGGC | ACGCCACCGG | 18350 |
| CGCTGCCCGG | CTCCCACCGG | GACGTCCCGG | AAGCGGTCGT | CCACGGGCGC | 18400 |
| GGCGAAGCGC | GGGGACGTGG | ACTCCCCCTC | CGCCGCGCAG | CACGTTGACG | 18450 |
| GCGAACTCGC | CGCGCTCCAG | GAGGGCCTTC | AGCACCCGGC | TGTCGCGGTT | 18500 |
| GATGCAGACC | CAGCAGCAGG | GGCGGGGCCT | TGGAGACGCT | GCAGGCGGCC | 18550 |
| GAACAGGTCA | ACCCGTACGG | CTCCCCGTCC | GGTCCCAGGG | TCGTCACCAC | 18600 |
| GGTGACCCCG | GTCGGCAGGG | CGCCCATGAT | CGACAGGAAG | GTGTCGCCGT | 18650 |
| CCACCAGGCC | GGGAGCCAGG | TCCAGCGGCA | GGGACAGGGG | TTCGGGGGGC | 18700 |
| ATCGGTCCTC | CACTCTCGGC | GGGTCGGTGT | CCCCATGCTC | GCGGGGCGCC | 18750 |
| TTCGAGCCGG | CGCCGGGCCG | TCGTCGGGCC | CTCCGCGCAC | GCGAACGGGC | 18800 |
| GCGCAAACGG | GCGCGCGAAC | GGGCGCGCGC | GAGGGCGCGC | GGACGCGGCC | 18850 |
| GGAGCCGGAG | CGGAAAAGCG | CGTACCCCCG | GCACGGGGGT | GACCGGGGGT | 18900 |
| ACGCGCGGTT | CAGGGGGTCG | CGTGCGCGCG | CTCACTCCTC | GTCGCGCAGT | 18950 |
| TCCCGCAGCG | GGAAGGTGAG | CAGGAAGCCC | ACCGCAAGGA | TCAGGCCGCC | 19000 |
| GACCAGGAAC | ATCGTGTCGA | AGCCCGAGGT | GAAGGCGTCG | ACCGCCGAGG | 19050 |
| CGCTCAGGCC | GCCGGTGGAG | TCCGGGTCGG | AGAGCGCACG | GCGCACGGCC | 19100 |
| TCGTCCGGGT | CGGCCCCGTC | GAGCCTGCCG | GCGGCGACGC | CGAACAGCAC | 19150 |
| CGACATGAAG | ACGGCGGCGC | CGCTCGTGCC | GCCGAGCTGG | CGGAACAGCC | 19200 |
| CGGAGGCGGC | GTTGGCCACG | CCCAGCTCGG | ACTTGGGCGC | CGAGCTCTGG | 19250 |
| ATCGCCAGGG | TGATGACGGT | CTGGGAGAGC | CCGATGCCGA | AGCCCAGCCA | 19300 |
| GGCCGCGATC | ACCACGATCA | CCGCGAGCGG | GGTGTCCGCG | CCCGCGGCGG | 19350 |
| AGAGCGACAG | CAGTGCTCCG | GCCATCGAGC | CGAGGCCCAC | GATCGCGGGC | 19400 |
| TTCTTGTAGC | GGTTCCACTT | CTTGATGATC | TTGGCGCAGA | TCGTCTGGGA | 19450 |
| GACGATCGCC | CCGGTCATCA | CCGGGATGAT | CACCAGTCCG | GCGACGGTGG | 19500 |
| CACTGCGCCC | CTGCACCAGC | TGCAGGAACA | GCGGCAGGGT | GGAGACCGTA | 19550 |
| CCGAAGATGC | CGACGCCGAT | GGTGAAGTTG | ACGGCCGTGG | TCATCGTGAT | 19600 |
| GCCACCGCGC | CGGAACAGCC | GTAGCGGGAC | CATCGCCTCC | AGCCCGCGGG | 19650 |
| CCCGTTCGGC | GAGCACGAAC | AGCACCAGGC | CGATCAGCGA | GACGGCGAAC | 19700 |
| AGCGTCAGCG | AACGCGCCGA | TCCCAGCCC | CAGTCGAGGC | CCTCCTCCGC | 19750 |
| CACGATCAGC | AGCGGCACCA | GGCAGAGCGC | CAGGGTGAGC | GCCCCCCGGA | 19800 |
| AGTCGATCGG | GTGGTCCACC | CTGCGGTGCG | GCAGGTTGAG | CGCCTTGCGC | 19850 |
| ACGCTGAGCA | GCGCCACGAG | ACCGAGCGGC | ACGTTGATCA | GGAAGGCCCA | 19900 |
| GCGCCAGCCG | GTCACCCCGA | GGATCTCGCC | GGCGCCCGCG | AACAGGCCCC | 19950 |
| CGACGAGCGG | GCCGAGCACA | CTGGCCGCCA | CCCAGGCCAT | CATCAGGTAC | 20000 |
| GAGAAGTAGC | GCCCGCGCTC | GCGCACCGGG | GCGAGGTCGG | CGATGACGGC | 20050 |
| CGTCGGCAGC | GACATCAGCC | CGGCGCCGCC | GAAGCCCTGG | AGGACGCGGG | 20100 |
| CGATCGCCAG | CGTCTCCATC | GAGTTCGCCA | TCGCGCAGGC | CGCCGAGCCG | 20150 |
| ACGATGAAGA | CCGCGATCGC | CGCCAGATAG | AGCGGCTTGC | GGCCGTAGAT | 20200 |
| GTCGGACAGC | TTGCCGTAGA | ACGGCATCGC | GATCGTGGAG | CTGACCAGGT | 20250 |
| AGCCGGTGAT | CACCCAGGCC | TGGACGGTCT | GGCCGTGCAG | TTGGTCGCCG | 20300 |
| ATCGTACGCA | GCGCGGTGGA | GACGATCGTC | TGGTCGAGTG | CGGCGAGCAG | 20350 |
| CACGGCCAAC | AGGAGCCCGG | ACAGCGCGGT | GATGATCTGG | CGGTGAGTGA | 20400 |

FIG. 4I

```
AGCCGGCGGG GCCGCCGGCC TCGTCCGCGA CGGCCTCGCC GGTCTGCGAG    20450
GTGGCGTTCG CCATTCCCAT TTCTCCCACC GAATTCGACA AGGTCTTGTC    20500
GAACTGAGCG TAGTGGGCTA CCGTGGCGGA ATGACAAGTT CTTGCCGAAA    20550
TCCCGGCCCG GACGAGGCTA GGCTGGCCGT GGAGAGCCTG CGATTAGGCT    20600
GCCCCCATGA CCGATCTCTC CCCCGCGGCC GAGACCTTGA GTGACATCAC    20650
CACCGAACTG TTCGCCGTCA ACGGAGCCCT GCTGCGCGCG GGCGACGCGC    20700
TGTCCGCCCG CTTCGGGCTC ACCTCCGCGC GCTGGCAGGT CCTCGGGCTG    20750
CTGGCCGAGG GGCCGCAGAG CGCCGCCCAC CTGGCGCGCG AGCGGGCTGC    20800
GCCGCCAGCC GTCCAGCAGA CCGTGGTGAA GCTGGTCGAG GAGGGCCTGG    20850
TCAGCACCTC CCCCAACCCG GCCGACCGGC GGGCCCCGTT GGTCTCGCTG    20900
ACCGCCAAGG GCACCGACGC CCTCGCCCGG ATCGAACCCG CCGAACGCCT    20950
GTGGATGGAG CACCTCGCGG GCGGCCTGGA TCCGGACGAC CTGACAGGCC    21000
ACGCTGCGGC TGCTGCGTGG CTTCGGGCGG TCCTGGCCGA GGGGCTGCCC    21050
CCGACGGCGG TCGGCGGCGC GGACGCCGCC GACGTCACAG GTCCAGCGTG    21100
ACCTCGTACT CGGCGAGCCA GGAGTTGAGC CACAGCACCA GCTCCAGACT    21150
GCCCCGGTCG TAGGGCCGGC TCACCGCCCC GGTCGGACGG GCAGCCGCGG    21200
CCAGGGCCCG CTCGCGGTCC AGCAGCGGCA GCACCGGAGC GTCCGGATCG    21250
GCGAGCACCC CGGCCAGTTC GGCCCGCAGG GCGCCCTCGT AGCCCGGATC    21300
CTGGGTCGCC GGGTACGGGG TCTTCACCCG CTCGACCACC GAGCGCGGCA    21350
GCAGGTCGGC CACCGCCGCC CGCAGCAGGC TCTTCTCCCG GCCGTCGAAA    21400
CTCTTCATCT CCCAGGGCAC GTTGAAGACG TACTCCACGA GCCGGTGGTC    21450
GCAGAACGGC ACCCGCACCT CGAGGCCGAC CGCCATGCTC ATCCGGTCCT    21500
TGCGGTCGAG CAGGGTCTGC ACGAAGCGGG TCAGGTTCAG GTGACCGATC    21550
TCGCGCATCC GCCTCTCGGG CGCCGACTCA CCCGGCAGCA CCGGCACTTC    21600
GGCGAGCGCC TCGGCGTACC GGGCCGCCCG GTAGCCGTCC AGGTCGAGCT    21650
TGTCCAGCAG ACCCGCCTGG AACAGCGAGC TGCCGCCGAA GTAGCGCGCC    21700
GAACCCGGGG TGAGCCACGG GAAGGTGGCC GCCCGCAGGG CCAACGGGTT    21750
GCGGAACCAC CGGTAGCCGC CGAAGAGTTC GTCCGCGGCC TCGCCGGACA    21800
GCGCCACCGT GACGTTCTCC CGCACCGCGC GGAAGAACAG GTAGAGCGAG    21850
GGCCACATGT CGCCCCAGTA CGCGGGCGGC AGGTCGGTGG CGCGCAGCAC    21900
CGCGGAACGC ACCGCCGGGT CCGACAGGCC GGGGCTGTCC AGCAGCACCT    21950
CCAGGTGGTC CGCTCCGACG TGCCCCGCCA GCTCGCGCAC GTACGGCGCG    22000
TCCGCCTCCC GCCGGACGGC GTCGGAGGCG AAGGCGTCGG CGGCGCCCCG    22050
GAAGTCCACC GAGAAGGAGC GCACCGGCCC GCTGCGGGCG GCCAGCGCCG    22100
TCACGGCCGA CGAGTCCAGG CCGCCGGAGA GCAGCGTGCC CAGCGGGACG    22150
TCCGAGACCA GCTGACGGGT GACGGTGTCG GCGAGCAGGT CACGGACGGT    22200
GCCGATGGTC GTCGGCAGGT CGTCGGTGTG CTCGCGGGCC TCCAGCCGCC    22250
AGTACGTCTG CCGGCGCACC CCGCCGCGCC CCACCCGGAC GAGCTGACCC    22300
GGACGGACCT CGACGAGCCC GGAGAAGACG GCCGCTCGG GCGTCTTCAC     22350
CATGTCCAGC ACCTCGCACA GCCCGTCCGG GCCGACCCGG CGGGACAGGG    22400
TCCGGTCCGC CAGGACGGCC TTGGGCTCCG AGCCGAAGCG CACGCCGGCG    22450
GCGGTCGGCC AGTAGTAGAG CGGCTTGACG CCCATCCGGT CGCGGACCAG    22500
CAGGAGTTCC TCGCTGTGCT CGTCCAGAC GGCGAAGGCG AACATCCCGT     22550
TGAGCCTCTC GACCAGCGCG GCGCCCCACT GGAGGTAGCC GCGCAGGACG    22600
ACCTCGGTAT CGCAGGACGT CCTGAACCGG TGGCCGTGCG AGGTGAGTTC    22650
GGCGCGCAGC TCACGGAAGT TGTAGATCTC GCCGCTGAAG GTGATCGCCG    22700
CGCCGCGGCC CTCGTGTTCC GCGGTCATCG GCTGCCGGCC GTGCTCGGGG    22750
TCGATCACCG ACAGGCGCCG GTGACCGAGC CCGGCCGCGC GGCCGAACCA    22800
GAGGCCCTCG GCGTCCGGCC CCCGGCAGGC CATGGTGTCG GTCATCGCCT    22850
GGAGCAGGTC CCGGCGGTGT TCGGCCGGGG CGTCGTAGTC GACCACCCCC    22900
ACGATTCCGC ACATGCTCAG CCGGCCGTGG CGAGACCGAG GTTGACCGCG    22950
```

FIG. 4J

```
TCCAGGAGCA TCCGCGGCGT GGTGGCCTCC ACCACGGTCT CGTCGGGCAG    23000
GGTGATGCCG CGCTCGCGCT CGATGGTGTT GAGGGTGTTG AACAGGGCGA    23050
GCGAGTCGTA GCCGAGGTCG GCGAAGGGGA CGTCCAGGAT GTCGTCGAGG    23100
GCGACGCCCT CGTCGGCTCC GGCAGCCTCC TTCAGCGCGG CGATCAGGTC    23150
GTCAAGGGTG AACTCTGCCA TGGCTGTTCC TCACATCGGT GGGTCGGTCT    23200
GTCGAATCCG GAAGGTCAGG CGGGCGGTCG GCCGGCCCGG TCAACTGGTC    23250
AGTACGAGAG CGCTGTTGAA GCCGCCGTGG CCGCGGGCGA GGACCAGCGC    23300
GCTGCCCAGC CGGGCCGGCC TCGGCGGTCC CAGCACCAGG TCGAGGTCCG    23350
GGTGGGCCGG CCGGCCGATG TGCACGGACG GCGGGATCAC CCCGTCCCGC    23400
AGGGAGAGCA GCGCGGCCGC GACGTCCAGC GGGGCGCCAC CGGCCAGCAG    23450
CCGGCCGGTC ATCGTCTTGG GCGCCGTCAC CGGCACCCCG CGCGGGCCGA    23500
ACACCGCGCC CAGCACCTCG GCCTCGGCGC GGTCCTGCTC GGCCACACCG    23550
CTGGCGTCGG CGAAGACCAC GTCGACGTCG GAGGGGCCGA TCCCGGCGTC    23600
GGCGAGCGCC GTGTCGATCG CCCGGCGCAG CCCGGGCGGG CGCCCGGAGC    23650
CGGGTCGGGG GTCGAAGGTG GCCGCGTAGC CGGCGATCCG CCCGTAGTGG    23700
CGGTGCTGCC CGCGCTCGGC GGCGCCGTCC GGGGTCTCCA GCACGAGCAG    23750
TGCGCCGCCC TCGCCCGGCA CCCCGCCGGA GGCGTCGGCG TCGAAGGGCA    23800
GGAAGGCCCG CTGCGGGTCC CGCCGGGGGC TGACCGTGCC GCTGCGGCTG    23850
AGGCAGAGCC ACGACCAGGG GCAGAGCGAG CCGTCCACCG CGCCGGCCAG    23900
CATCAGCGCG GTGCCCTCGC GCACGTGCCG GCGGGCCTTG GCCAGCGCGT    23950
CCAGGCCGCC CGCCTGCTCG GCCACCAGGG CCGAACCGGG GCCGCGCATG    24000
CCGTGCCGGA TCGAGATCTG CCCGGTGTTG ACCGGGTAGA ACCACGCGAA    24050
GGACTGGTAG GCGCTGACGT AGGCCGGGCC CTTGCTCCAC AGCGCCTGGA    24100
GTTCCTTCTG GCCGAACTCG AAGCCGCCGG CCGAGGCGGC CGTCACGACG    24150
CCGGCGGAGA AGTCCGGCAT CGTCGTCGGG TCCGCCCCCG CGTCGGCGAG    24200
CGCCTCCTCG GCCGCGACCA GGGCCAGCCG CGTCATGTGG TCGGTCTGCG    24250
GCAGCAGTCG GCCCGGCAGG TGTTCCTCCG GCGTGAAGTT CACCTCGCCG    24300
GCCACGTGCG CCCGGTACCC GGTGGAGTCG AAGCGGGTCA GCGGCCCGAG    24350
ACCGGACCGG CCCGCCAGTG TGGCGTCCCA GTACTCCGCA ACGCCCAGC    24400
CGTTCGGTGC CACCACGCCG ATCCCGGTCA CCACGACGTC GGTCATCCCC    24450
GGCTCCACTC CGGCTCGGCG AGCACGATCG CGCTCTGGAA GCCGCCGAAG    24500
CCGCTCGCCA CGCTGAGCAC CGTGCGCACC CGCTGTTCCC GCGCCACCAG    24550
CGGCACGTAG TCGAGGTCGC ACTCGGGATC GGGCACGTGC AGGTTGGCCG    24600
TGGGCGGCAC CACCGAGTGC TCGATCGCCA GCGCGCTGGC GGCGAACTCC    24650
AGGGCGCAGA CCGCGCCCAG CGAGTGTCCG ATCATCGACT TGATCGAGCT    24700
GACCGGCACC CGGTAGGCGT GGTCGCCCAG GCTCTTCTTG AACGCGGCGG    24750
TCTCGTGCCG GTCGTTCTGC TTGGTCGCCG AGCCGTGCGC GTTGACGTAG    24800
CCGACGTCCT CGGGGTTCAT CCGGCTGCGG TCGAGCGCGA CCCGGATAGC    24850
CTCGGCCATC TCGTTCCCGT CGACCCGCAG CCCGGTCATG CTGTAGGAGT    24900
TGCAGCGCCC GGCGTAGCCG GTGACCTCGG CGTAGATGTG CGCGCCGCGC    24950
CGGATCGCGT GCTCCGCTC CTCCAGCACG AACATCGCCC CGCCCTCGCC    25000
GAGGGCGAAG CCGTTGCGGG TCAGGTCGAA GGGGCGCGAG GCGCTCTCGG    25050
GTTCGTCGTT GCGCGGGGTG GTCGCCTTGA TCGCGTCGAA GCAGGCCACC    25100
GTGATCGGGG AGATCGCCGC GTCCGAGGCG CCGGCCAGCA TCACGTCGGC    25150
CGCGTCGTCG CGGATCAGGT CGCAGGCGTG CGCGATCACG TCGATCCCCG    25200
AGGTGCATCC GGTCGACACC ACGCCCACCG GACCCTCCGC CTCGACCAGC    25250
CAGGCCAGTT CGGTGGCCAT CGAGGACGGG ACGAAGTAGT CGTAGAGGTA    25300
CGGGACGCCG TGCGCGTCGT CGACCAGCCG CTTGCGGCCC TCGTCGCTCA    25350
CCACGGCGAA CTCGCGGTCC AGACTGATCG TCATCCCACA GGCGGTGCCG    25400
GCCATCACCC CGGTGCGGAT CGGGTCGTTG ACGCCCGACA CCCCCGAGTC    25450
GTCCAGCGCC TCGCGCGCGG CGACCACCGC GAACTGCGCG GTGCGGTCCC    25500
```

FIG. 4K

| | | | | | |
|---|---|---|---|---|---|
| ATTGACGGAT | CTGACGCTGC | GTCAACCCCG | CGGCCTGCGG | GTCGAAGTCG | 25550 |
| CACTCGGCGG | CGACCCTGGA | CCGGAACGGC | GAGGGGTCGA | AGGTCGAGAT | 25600 |
| CGTCCGGGTC | GCGGTCCGGC | CGGCCGTCAG | CAGCTCCCAG | AACGCCTTGG | 25650 |
| TGCCCACCTC | GCCCGGTGCC | ACCACGCCGA | TCCCGGTGAC | CACCACGCGC | 25700 |
| CGGCGGCCGT | CGTCAACTCC | CACCACTGCT | CCCCCTGTCG | ATCTCCCCGT | 25750 |
| GCGTGTCCGG | CGTCATGCCC | TGACCTCCTG | TCCGTGCGGC | CCGTCCGCGG | 25800 |
| GCTCGGGCGG | GCGGGACTT | GAGCCGGATC | AGATCGTCCT | GGCAGGCGTT | 25850 |
| CGCGGCGGCT | TCGAGCCGCC | GTCCACGCGC | CTCCGGCCCC | CGCCTTCCCG | 25900 |
| CCGCGGCGGG | AAGAGCCGCA | CGCACGACGG | CGGCGGCGCC | GCACCCACGG | 25950 |
| CGGCGGGAAG | ACGACGCGAA | CCGGCGTCGA | AGGGCGCCCC | CTAGCGTCTG | 26000 |
| GCCGCATGGA | CATCGACACC | GACATCTGCG | TGGTCGGCGG | CGGCCCGGCC | 26050 |
| GGGCTGACCC | TCGCCCTGCT | GCTGGTCCGC | TCGGGCCTGC | GCGTCACCGT | 26100 |
| GCTGGAACGC | AGCCGCTCCC | TGGACCGGGC | CTACCGCGGC | GAGATCCTCC | 26150 |
| AACCCGGCGG | CCAGGCCTTG | CTGGACGAGC | TGGGCGTGCT | CGGCCCGGCC | 26200 |
| CGGGCGCACG | GCGCCGTCGA | GCACGACCGC | TTCCTGCTCG | AGGAGCACGG | 26250 |
| ACGCGTCCTC | ATCGACGGCG | ACTACCGGCG | CCTGCCCGGG | CCGTACAACT | 26300 |
| GCCTGCTGAG | CCTGCCCCAG | CGGCACCTGC | TGACCGAACT | GCTCGCGGCC | 26350 |
| TGCGAACGCC | ACGAAGGATT | CCGCCAGTTC | GCGGGCGCCA | AGGCCACCGC | 26400 |
| CCTGATCGAG | GAGGGCGGCT | TCGTCCGCGG | TGTGGTCGCG | GGCGGCGCGG | 26450 |
| GCGGCTCCCC | CGACCGGGTG | GTGCGGGCCC | GCTGCGTCGT | CGCCGCGGAC | 26500 |
| GGCCGCTTCT | CCAAGGTCCG | CTCGCTCGCC | GGGATCGGCT | ACCGGCGCCA | 26550 |
| GGAGCTGTTC | AGCCAGGACG | TCCTGTGGTT | CCGGCTGAGC | GCACCGCCGC | 26600 |
| GCACGGACAC | CCGACGCCCG | TGCGACGTCC | GGGTCTTCCG | GGCCGGCGGC | 26650 |
| AATCCGGTAC | TCAGCTACCG | CTCGGTGCCC | GAGGCGCTCC | AGCTCGGCTG | 26700 |
| GACCCTCCCG | CACGGCGGCT | TCCGCAAGCT | GGCCGACCGC | GGCATCGGCC | 26750 |
| ACATCGTCGA | CCAACTCGTC | GACGCCGCAC | CGGAGTACGC | CGACCTGATC | 26800 |
| CGCCAGGAGA | TCACCGGCTT | CGGCGACGTC | TCCCTGCTGG | ACGTCTTCTC | 26850 |
| CGGCAGCGCC | GAGCACTGGG | TGCGCGACGG | CCTGCTCCTG | ATCGGCGATG | 26900 |
| CCGCCCACAC | CCACAGCCCG | ATCGGCGCCC | AGGGGATCAA | CCTGGCCGTC | 26950 |
| CCGCCGCCGC | GTCGGGCCCA | CCCGGTGCTG | GTCGAGGCCG | TCCGCGGCGG | 27000 |
| CGACGCGGCG | CGGCCCGGCT | CGCCCCGTAC | GAACGGCAAC | GCCGCCCCCG | 27050 |
| AAGTGGAACG | GATCACCCGG | ATCCAGCAGG | TCCAGAGCCG | CATGATGCTC | 27100 |
| TCCACCGGGC | GCATCTCCTC | CACGGTGCGC | CCCCGGGCCG | CGGCGCTGGT | 27150 |
| GTCCAGGACC | CCGCTGTACG | GGGCCGTGCT | GCGCCGGATC | GCCTTCGGCA | 27200 |
| CCGCGCCCGT | CCGGCTGCGC | GCCGATCTGC | TCGCCGGGGC | GGGGCGGTGA | 27250 |
| GCGGCGGGGC | AGCGATCGCC | GCCGGCGACT | CGGCGACGGC | GAGCGGGGTG | 27300 |
| CTCCTCGCCC | TCGCCGTCGT | CCTCGCCAGC | GCGTTCGTCT | GCGGCCGGCT | 27350 |
| CGCCGCCCGG | GTGCGCCAGC | CCGTCGTCAT | GGGGGAGATC | GTCGGCGGGG | 27400 |
| TGGCCCTCGG | CCCCAGCCTG | CTCGGGCTGC | TGCCGGGGCA | CCTGGACGCC | 27450 |
| TCACTGTTCC | CGGCGGAGGT | CCAGTCCTAC | CTGCGGGTGC | TGTCCCAACT | 27500 |
| GGGCCTGGTG | CTCTTCATGT | TCACCGTCGG | CCTGCGCTTC | GACGTCGGCC | 27550 |
| ACCTGCGCGG | CGCCGGGCGC | CGGGTGACAG | CGGTGTCGCT | CAGCTCGGTG | 27600 |
| GCCCTGCCGT | TCGCGCTCGG | CGTGGGCTC | GCGGTGCTGC | TCTACCCCTG | 27650 |
| GTTCGACAAG | GCCCAGTTGA | GCACCGACGG | GAGGCTCGGC | CCGGCCCTGT | 27700 |
| TCCTGGGCGC | GGCGATGTCC | ATCACGGCCT | TTCCCGTCCT | CGCCCGGATC | 27750 |
| ATCGCCGAGC | GACGGATGCA | GCACGACCCG | CTCGGCAGCC | TGTCATTGGC | 27800 |
| CTGCGCGGCC | TTCCAGGACT | TCCTCGCCTG | GTGCGCGCTG | GCGGTGGTGG | 27850 |
| TGGCGGTGGT | GGAGGCCAAG | GGCCTCTGGT | CGCTGGGACG | GCTGGCGCTC | 27900 |
| GACACGGCGG | TGGTGGTCCT | GGTGCTGGTC | GGCGTCGTCC | GCCCGCTCCT | 27950 |
| CTCCCGGCTG | CTCGCCCCCG | GCCGGCGCCC | TCCCCTCCCC | CGGCCGTGGA | 28000 |
| TCCACGCGGT | GCTCGTCACC | GGCACCCTGG | TCACCGCCTG | GGTCACGGCC | 28050 |

FIG. 4L

```
GAGATCGGCC TGGACGCGGT GTTCGGGGCG TTCATGTTCG GTGCGGCGGT      28100
GCCCCGGGAC CGGATCGAGG CGATCGCGCC CGACGTCCCG GAGCAGATCG      28150
AGCGGGCGGG TCTCCTGCTG CTGCCGGCCT TCTTCGCGGT GACCGGCCTC      28200
GCCGTCGACC TCACCGGCCT CGGGCTGCGC GGCCTGGCCG TCGTGGCGGC      28250
GGTGCTGGTG GCGGCCTGCG CCGGCAAGTT CGTCGGTGCG GTCGCCGCCG      28300
CCCGGGCCAC CGGCTCGAGC CGGCGCGAGG CGCGGGTGCT CGGCATCCTG      28350
CTCAACGCCC GGGGCCTGAC CGAGCTGGTC ATCCTCAACG TGGGCCACCG      28400
GCTCGGGGTG ATCGACACCC GGATGTTCAC CGCCATGGTG GTGATGGCCC      28450
TGGTCACGAC GCTGATGACG GGGCCGCTCC TGGAGCGCCA CACGGCGGGC      28500
TCCGCCGGAT CCGCCACGCT CCCGGACCCG GCGCCCGAGG CCGCACAGGC      28550
CTCGCGGACA ACCTCCTGAT GGCGGGCCGG CCACGACCTC CGGGGGGCGT      28600
GCCCCTCACG GCGGCTCCGT CCACCCGGAG ACCCGGCGCA GCCGCGACTC      28650
AGCCGCCGCT CGACCGGGCT GAGCGGAACG TCGGGCGCA GCCGCTCCGG       28700
GTGCCCCGAC GGTGGCCCGC CCCCGGCAGG GCCGCCCGGC TCGCCGGGCG      28750
CCGGACCGGC CCGGGCTGCG GCGGCGGGGC CACGTAGCCG GCCATCTGCC      28800
CCAGCGCCGC CAGTCCGCGC AGGAGCACGG CCAGCAGATC GAGGAGCCGT      28850
TCGTTCGGTT CGCACATCCG CCGAGCATGG CGACCGGTCC TGAAGCGCGG      28900
TTCGAGCGGT ACGGGAGGGG CGCCGGGCAC GGCGGAGAGG ACAGCCCGGC      28950
ACCCTCGGAA CCGCTGGAGC ATGACCACGG CGCCGTCGGA GCTGCGGGTG      29000
CCCGTCACAC TGACGATCCG CCGCAGGAGG GTCGGGCGTG TCCGAGGGTT      29050
CCCGCCGGAC CGGCCCCGAG CCTCACTGGT ACCGGTAGGT GGCGGCCACC      29100
GCGAGGTGGT CGCTGCCGTC CCGGGGCAGG GTGCGGGAGT CCACCGGCTT      29150
CAGCCCGCCC TTGCTCATGA TCTGGTCGAT CCGCGCCATC GGGAACGCCG      29200
CGGGCCAGCT GAAGCCGAAG CCGTCCCCGG CCGCGCCCTG GCCGAGCGC       29250
ATCTGCGAGG TGACCGGTGC CAGGCTGCGG TCGTTCATGG TGCCGTTGAG      29300
GTCGCCGAGC AGCAGGACCT TCTTCACCGG CTCGGCCTGG ATCGCGTCGC      29350
CGAGCGCCTG GGCGCTGACG TCCCGCTGGT GGGCGGTGAA GCCGCTCTCG      29400
GCCTTGAGCC GGACGGACGG CAGGTGCGCG ACGTACACCG CGACCGGGCC      29450
CTGGGGGGTG GTGACCCGGG CCCGGAAGGC CCTGGTCCAA CCGATCTTCA      29500
GGTCCACCGA GGAGACCTCG CCGATCGGGT ACTTCGACCA GAGTCCGACC      29550
GTCCCCTCCA CCGTGTGGTG CGGGTACGCC CCGGCGAGCC CGGTCTCGTA      29600
CGACCGCAGC TGGTTGCCGG CCAGTTCCTG GAGCGCGACG ATCTGGGCGT      29650
CCGAGGCGAC CAGGCCGCGG ATGGTGCCCG GCACGTCGGT GTTCCCGGCC      29700
TCGACGTTGT GGGTGACCAC CGTCCAGTCG CCGGTGCCGC CGCTCTTGTC      29750
GGACACCAGC CCGCCGAACA GGTTGGCCCA CAGCACGGCG GCACCAGCA       29800
GGGCGAGCAG CGCGGTGGCG GAGCGGCGCA GCAGCGCGGG CACCAGCAGC      29850
ACCGGGACGG CCAGGCCGAC CCAGGGCAGG AAGGTCTCCA GCAGGCTGCC      29900
GAGGTTGCCG ACGCTGTTCG GCATCTCGGC GTGGAAGGCC AGCAGCACCG      29950
CGGTGAGCAG GGCCAGCAGG GCGATCGGCC AAGTGGGCGG CCGTCGGGAT      30000
C                                                          30001
```

CLONING OF THE BIOSYNTHETIC PATHWAY FOR CHLORTETRACYCLINE AND TETRACYCLINE FORMATION AND COSMIDS USEFUL THEREIN

RELATED U.S. APPLICATION DATA

This is a divisional of application Ser. No. 08/125,468 filed on Sep. 22, 1993, U.S. Pat. No. 5,589,385, which is a continuation-in-part of two U.S. applications, (1) Ser. No. 07/821,109, filed on Jan. 15, 1992, now abandoned, which is a continuation of application Ser. No. 07/558,040, filed on Jul. 26, 1990, now abandoned, and (2) Ser. No. 07/821,419, filed on Jan. 15, 1992, now abandoned, which is a continuation of application Ser. No. 07/558,039, filed on Jul. 26, 1990, now abandoned.

BACKGROUND OF THE INVENTION

DESCRIPTION OF THE RELATED ART

The antibiotic chlortetracycline and its derivative compounds (e.g., tetracycline, demethylchlortetracycline, demethyltetracycline) are produced commercially in submerged fermentation by *Streptomyces aureofaciens* (Dugar, 1948). More than thirty years of industrial manipulation of this microorganism has resulted in the development of sophisticated fermentation techniques and media formulations that have allowed significant improvements in fermentation yield (Goodman, 1985). These advances in yield improvement have also been aided by the isolation of mutants of *S. aureofaciens* with increased ability to produce antibiotic (Veselova, 1969). These high-producing strains have largely been isolated by the process of mutagenesis, followed by random screening for improved yield. The same techniques allowed the isolation of mutants blocked in antibiotic biosynthesis which were critical tools for the elucidation of the biosynthetic sequence for chlortetracycline formation (McCormick, 1968). Despite these accomplishments, an understanding of the genetic regulation of chlortetracycline biosynthesis was not completely realized. Recent developments in the field of Streptomyces genetics have created the opportunity to study molecular genetics of organisms producing industrially important metabolites.

The demonstration of recombination of chromosomal markers by the fusion and subsequent regeneration of Streptomyces protoplasts- (Hopwood et al., 1978 and Baltz et al., 1981) was a pivotal event in the genetics of the actinomycetes. Prior to the development of techniques for protoplast fusion, genetic crosses could only be reliably performed in a few species with demonstrated conjugal systems (Hopwood, 1967). Now, genetic analysis can be performed in any species which can be protoplasted and regenerated. More importantly, protoplasts later proved to be an ideal substrate for transformation by plasmid DNA, thus creating the opportunity to do recombinant DNA experiments in these organisms (Bibb et al., 1978). The isolation of genes for several antibiotic resistances, such as thiostrepton, viomycin and neomycin, allowed the construction of readily selectable cloning vectors from indigenous Streptomyces plasmids (Thompson et al., 1982).

One of the first antibiotic biosynthetic genes to be cloned was the o-methyltransferase involved in the formation of the antibiotic pigment undecylprodigiosin (UDP) (Feitelson et al., 1980). The gene was identified by its ability to complement a known mutation in the UDP biosynthetic pathway. Other techniques employed in these early efforts to isolate biosynthetic genes included mutational cloning using phage OC31 for methylenomycin (Chater et al., 1983), a sib selection of recombinant clones using Ln vitro enzyme assays for the actinomycin phenoxa-zinone synthetase (Jones et al., 1984) and sulphonamide resistance conferred by the p-aminobenzoic acid synthetase involved in candicidin production (Gil et al., 1983). Bialaphos biosynthetic genes were identified via complementation of blocked mutants (Murakami et al., 1986).

Genes involved in actinorhodin biosynthesis were cloned by complementation of biosynthetically blocked mutants of *Streptomyces coelicolor* (Malpartida et al., 1984). In this last case, two overlapping clones complementing distinct classes of mutants were combined on a single plasmid which was shown to confer the ability to synthesize actinorhodin when introduced into a heterologous *Streptomyces parvulus* host.

Another important series of observations was that genes for antibiotic biosynthesis were physically linked to the resistance determinant(s) for that same antibiotic in the producing organism. Thus, a DNA fragment from *Streptomyces ariseus* conferring streptomycin resistance was shown to be contiguous with DNA that complemented biosynthetic blocks (Distler et al., 1985). The same situation was seen in *Streptomyces fradiae* where biosynthetic genes had been identified by probing a cosmid library for homology to a mixed-base oligonucleotide constructed to represent the DNA sequence for the amino-terminus of the final enzyme in the tylosin biosynthetic pathway (Fishman et al., 1989). A previously cloned tylosin resistance gene (tlrB) was shown to be contained within this region of DNA, which complemented nine classes of blocked mutants (Baltz et al., 1988). In the cases of puromycin (Vara et al., 1988) and tetracenomycin (Motamedi et al., 1987), a primary selection for expression of antibiotic resistance gene in the heterologous host *Streptomyces lividans* allowed subsequent identification of antibiotic biosynthetic genes located on the same cloned DNA fragment.

The use of nucleic acid probes has aided the isolation of biosynthetic genes. This approach relies on the existence of a pre-existing body of information concerning the pathway or prior cloning having been performed. Thus, in the case of tylosin above, a probe was constructed using information from a partial amino acid sequence of a biosynthetic enzyme (Fishman et al., 1987). Similarly, the gene for isopenicillin N synthetase was cloned from *Streptomyces clavuliperus* by identifying a clone hybridizing to an oligonucleotide probe constructed with a knowledge of the N-terminal amino acid sequence of the enzyme (Leskiw, 1988). Genes involved in the biosynthesis of erythromycin were identified by probing a cosmid library with a previously cloned erythromycin resistance gene (Stanzak, 1986). Similarly, genes involved in the biosynthesis of oxytetracycline have been identified by hybridization to both a previously cloned resistance determinant (Butler et al., 1989) and an oligonucleotide synthesized to represent the DNA sequence corresponding to the partially elucidated amino acid sequence of the biosynthetic enzyme anhydrotetracycline oxygenase (Binnie et al., 1989). The use of heterologous actI and actIII probes allowed the identification of genes involved in anthracycline biosynthesis in *Streptomvces peucetius* (Stutzman-Engwall et al., 1989).

The use of these techniques individually or in combination has allowed the isolation or assembly of entire biosynthetic pathways from fragments of genes, and in some instances, their expression in a heterologous host. The entire biosynthetic cluster for bialaphos was cloned by a combination of selections for complementing activities and heterologous expression of bialaphos resistance (Murakami et al., 1986). While a successful isolation of the entire pathway in a single step in *Streptomyces lividans* by selecting for bialaphos resistance was noted, no mention is made concerning expression of the biosynthetic genes.

A bifunctional cosmid clone which hybridized to a homologously derived erythromycin resistance determinant was isolated from a *Saccharopolyspora erythrea* library and shown to direct the synthesis of erythromycin when transferred to *Streptomyces lividans* (Stanzak et al., 1986). An *E. coli* cosmid clone that showed hybridization to both an oxytetracycline resistance gene probe and biosynthetic gene probe (for anhydrotetracycline oxygenase) allowed the isolation of the oxytetracycline biosynthetic cluster from *Streptomvces rimosus* (Binnie et al., 1989). Subsequent subcloning into a Streptomyces plasmid vector allowed production of oxytetracycline in *Streptomyces lividans*.

Two overlapping clones from the tetracenomycin producer were identified by complementation of blocked mutants of *Streptomyces glaucescens* and ability to confer tetracenomycin resistance in *S. lividans* (Motamedi et al., 1987). When both were separately resident in *S. lividans* and co-fermented, or when they were co-resident in the same *S. lividans* host, tetracenomycin was produced. Bifunctional clones isolated from an *E. coli* library of *Streptomyces peucetius* DNA by hybridization to actI and actIII probes of *S. coelicolor* were shown to direct the synthesis of pigmented antibiotic when introduced into *S. lividans* (Stutzman-Engwall, 1989).

Additionally, the isolation of the biosynthetic pathway for cepthamycin C production has occurred (Chen et al., 1988). In this case, random clones in *S. lividans* were individually screened for cephamycin C production using an agar plug fermentation method. Out of 30,000 screened, one transformant of *S. lividans* was shown to be producing cephamycin C.

Although reports have been published concerning the cloning of a tetracycline-resistance determinant (Reynes et al., 1988) and a bromoperoxidase (Van Pee, 1988) from *Streptomyces aureofaciens*, these studies are in no way extended toward the isolation of chlortetracycline biosynthetic genes or the entire gene cluster.

The present invention is the first instance wherein the single DNA gene cluster related to the entire biosynthetic pathway for producing tetracycline and chlortetracycline is isolated and utilized.

BRIEF DESCRIPTION OF THE DRAWINGS

The background of the invention and its departure from the art will be further described hereinbelow with reference to the accompanying drawings, wherein:

FIGS. 4A–4L show the total DNA sequence from the cosmid clones designated LP$^2$127 and LP$^2$128 (this sequence is also set forth in Sequence I.D. No. 1). The sequence is obtained using the dideoxy chain termination method (Sanger et al., Proc. Natl. Acad. Sci. USA, 74:5463–5467, 1977). The *S. aureofaciens* DNA carried in the cosmid clones is fragmented either by digestion with appropriate restriction endonuclease or by sonication. The smaller pieces are eventually cloned into the M13 vectors M13mp18 and M13mp19 (Yanisch-Perron et al., Gene 3:103–119, 1985) using conventional methods and vectors (see, e.g., Sambrook et al., Molecular Cloning: A Laboratory Manual, 2d ed., Cold Spring Harbor Laboratory Press, Cold Spring Harbor, N.Y., 1989). The DNA sequencing is carried out at elevated temperatures using Taq DNA polymerase employing fluorescently-labeled primers using materials and methods supplied by the manufacturer (Applied Biosystems, Foster City, Calif.). The data are collected using a Model 370A/373A DNA sequencing system (Applied Biosystems, Foster City, Calif.). Compilation of the data, generation of overlapping sequences and the overall analysis of this DNA sequence information are carried out using the collection of standard computer programs contained within the Genetics Computer Group package (Devereaux et al., Nucleic Acids Research, 12:387–395, 1984).

SUMMARY OF THE INVENTION

The present invention relates to the cloning of the entire biosynthetic pathway for the formation of tetracycline and chlortetracycline from *Streptomyces aureofaciens* and its expression in a heterologous host such as *Streptomyces lividans*. In particular, the present invention concerns the purified and isolated nucleic acid molecule, e.g., a DNA gene cluster, coding for the biosynthetic pathway for producing the antibiotics or an analogue thereof.

The more detailed description of the present invention is provided hereinbelow through nonlimiting examples which are illustrative of the invention.

DETAILED DESCRIPTION OF THE INVENTION

In accordance with the present invention, there is provided a single, purified and isolated nucleic acid molecule which encodes the entire pathway for the biosynthesis of chlortetracycline and, indirectly, for the biosynthesis of tetracycline and analogues thereof. The nucleotide sequence of the nucleic acid molecule is shown in FIG. 4. Desirably, the nucleic acid molecule is a DNA gene cluster isolated from *Streptomyces aureofaciens*, or an antibiotic-producing mutant thereof, and expressed in a suitable heterologous host, such as an Actinomycetales, preferably *Streptomyces lividans*, which will make the antibiotics.

The present invention further includes the DNA sequences which hybridize under standard or stringent conditions to the sequence of the nucleic acid molecule isolated from the microbial source and encode for the biosynthetic pathway of tetracycline, chlortetracycline or the analogues thereof. It should be understood to those skilled in the art that the invention encompasses the purified and isolated polypeptides which may be encoded by the sequences of the nucleic acid molecules of this invention.

Figure 1B:
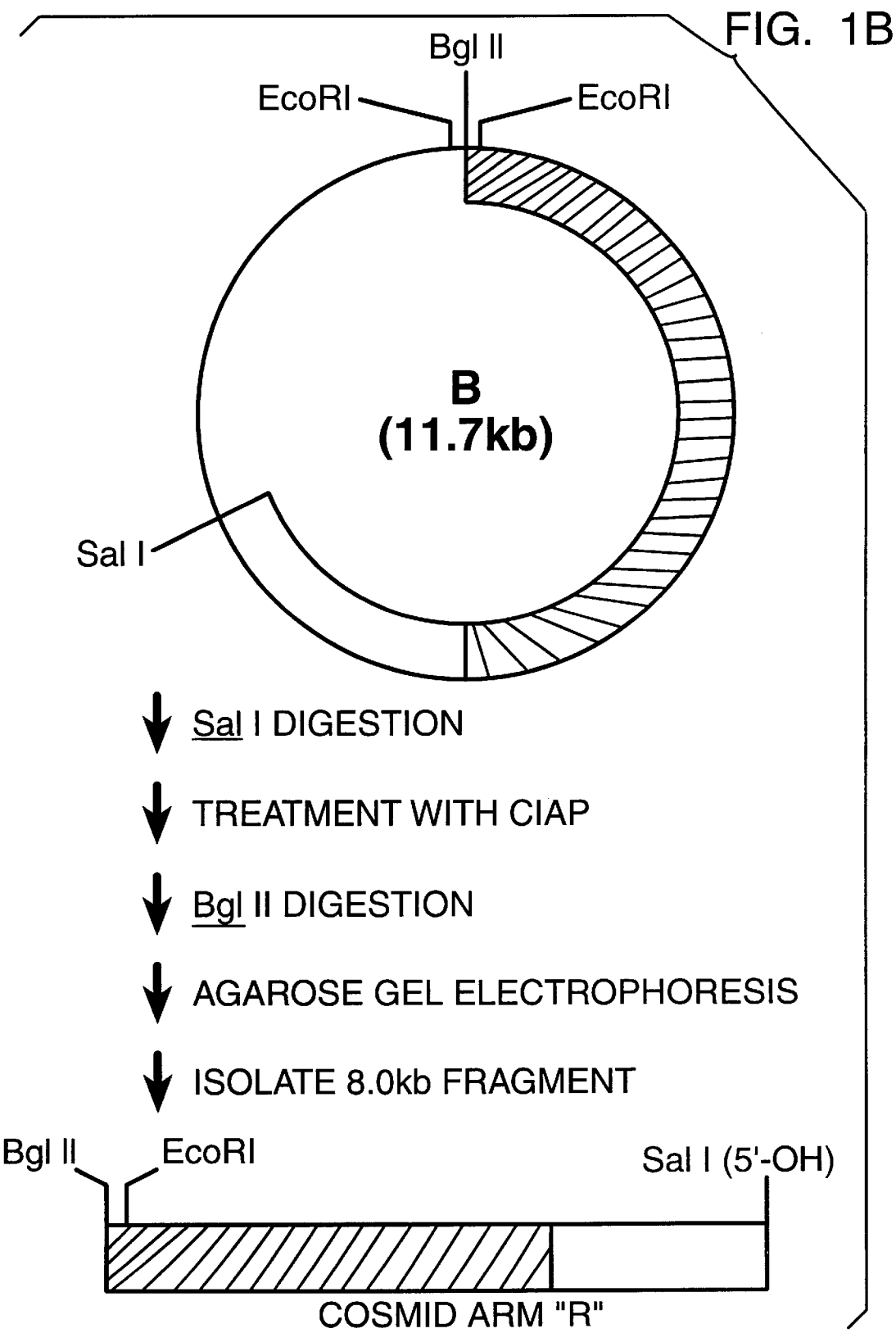
FIG. 1 shows the structure of the components of the bifunctional cosmid vector and method for generating cosmid arms. Cosmid vector arms L and R are generated from plasmids A and B, respectively, as shown in the figure and as detailed in Example 3. Single lines represent *Escherichia coli* replicon portions of the constructs. In plasmid B, the *E. coli* portion is derived from the 3.7 kb EcoRI-SalI fragment of pBR322 (Sutcliffe, 1979). Plasmid B contains a 5.9 kb EcoRI-SalI fragment from SCP2* (striped) that provides for replication function in the actinomycetes (Larson et al., 1986). Three tandem cohesive end sites derived from a 700 bp BglII-BstEII cos-containing fragment of pHC79 (Hohn et al., 1980) are provided on both plasmids (open). The thiostrepton-resistance gene (darkened) present in plasmid A is derived from a 1.1 kb BclI fragment recovered from pIJ702 (Katz et al., 1983). A 1.1 kb spacer region in plasmid A (stippled) is derived from a SacI fragment of bacteriophage λ (Sanger et al., 1982).

Additionally, the invention embraces a two-plasmid system and the use thereof for cloning the biosynthetic pathway of tetracycline, chlortetracycline or the analogues thereof. The preparation of the system is explained in Example 3 and the structures designated A and B are shown in FIG. 1. Together, the plasmids comprise an efficient cosmid vector which allows for the cloning and packaging of large, contiguous pieces of DNA. It is contemplated that these plasmids described herein may be employed for cloning large DNA from any source.

For the isolation of the biosynthetic genes, a screen of a recombinant *S. lividans* library for a clone expressing tetracycline-resistance is utilized. The *S. aureofaciens* DNA inserts in the recombinant cosmids which comprise the library are large since the constraints of the in vitro lambda packaging system demands cosmid molecules with DNA inserts of 25–40 Kb to yield a viable transducing phage particle. When tetracycline resistant clones are selected from among this population of *S. aureofaciens* genomic clones, a limited subset of cosmid clones is chosen. Many or all of these are expected to contain antibiotic biosynthetic genes linked to the selected tetracycline resistance gene. Among those that are sufficiently large and correctly positioned is a subset encompassing the entire biosynthetic pathway. Thus, the cloning of all of the genes for tetracycline and chlortetracycline formation is unexpectedly possible without any pre-existing knowledge of the structure or sequence of the region.

The method for isolating the DNA involves lysozyme digestion of cells in an osmotic buffer, followed by gentle lysis, protein extraction and enrichment for, and concentration of, high molecular weight DNA. Although the method described is efficient, those skilled in the art will recognize that a variety of alternative procedures may be employed such as those described by Hopwood et al., 1985.

The source of total DNA used in the examples is *Streptomyces aureofaciens* ATCC 13899 but the invention is not limited to this particular source. A variety of other *Streptomyces aureofaciens* strains producing antibiotics of the tetracycline class can be used in the present invention with equal success. These strains include mutant strains and alternative wild-type isolates producing chlortetracycline, tetracycline, 6-demethylchlortetracycline, 6-demethyltetracycline,7-chloro-5a,11a-dehydrotetracycline,2-decarboxamido-2-acetyltetracycline and other members of the tetracycline family of compounds. The present invention relates also to the cloning of chlortetracycline, tetracycline and tetracycline-related compounds from other organisms producing such compounds, which include, but are not limited to, *Streptomyces rimosus, S. avellaneus, S. lusitanus, S. viridifaciens, S. psammoticus, Actinomadura brunnea* and *Dactylosporangium vesca*.

A partial digestion of *S. aureofaciens* DNA with restriction endonuclease Sau3A to generate large DNA fragments in the desired 35-kilobase size range with ends homologous to those of the arms of the bifunctional cosmid vector is employed. In this case, an empirical determination of the optimal digestion conditions is obtained by conducting a series of digestions and analyzing a sample of the end products by agarose gel electrophoresis. Those skilled in the art will recognize alternative library construction and recovery methods for cloned DNA of interest. The present invention is not limited to the use of *Escherichia coli* and the size selection imposed by lambda packaging as described herein, since other vectors may be useful as well. Those skilled in the art will recognize that monofunctional Streptomyces vectors, such as pIJ922 (Lydiate et al., 1985), can be employed in the present invention with the proviso that library construction and recombinant plasmid recovery are conducted within the actinomycete.

The steps that follow in the examples involve in vitro packaging of the ligation products of cosmid arms and size fractionated DNA, transduction to *E. coli* X2819T, collection of the population of transductants and isolation of DNA from them to give a cosmid library. The methods used are described, but the invention is not limited by those described in the example. Alternative methods could be employed to the same end with no untoward consequences. Thus, alternative protocols for ligation and in vitro packaging may be employed, as well as alternative recombination-deficient (recA) *E. coli* hosts, library amplification procedures (e.g. selective broth growth) and plasmid preparation procedures, all of which have been published in the scientific literature (Maniatis et al, 1982).

Subsequent steps in the examples describe introduction of the pooled cosmid DNA preparation into *Streptomvces lividans*, creation of a cell library and subsequent screening of such a library for transformants of *S. lividans* exhibiting resistance to 100 μg of tetracycline/mL. Though more laborious, transformants could be directly screened for tetracycline-resistance by replica plating. Alternative levels of tetracycline could be used for screening as dictated by the innate resistance exhibited by the host or source organisms. Other tetracycline-sensitive, non-restricting hosts, such as *Streptomyces ariseofuscus*, could be substituted for *S. lividans*.

Next, recovery of recombinant plasmid by isolating plasmid DNA from the tetracycline-resistant *S. lividans* followed by in vitro packaging of said DNA and transduction into *E. coli* is obtained. Plasmid DNA isolated from such transductants is structurally characterized by restriction enzyme mapping analysis; and the two plasmids isolated in the example, LP$^2$127 and LP$^2$128, are shown to possess equivalent structures. Those skilled in the art will recognize that similar DNA regions cloned from alternative organisms could show polymorphism in the arrangement of restriction sites, but that a sufficiently large DNA fragment conferring tetracycline-resistance would be expected to confer the properties described hereinbelow.

The plasmid-borne nature of the tetracycline resistance is confirmed by demonstrating that thiostrepton-resistant transformants of *S. lividans* obtained with LP$^2$127 and LP$^2$128 are also tetracycline resistant. The elaboration of tetracycline-like antibiotic is demonstrated by the production on agar by the aforementioned thiostrepton and tetracycline resistant *S. lividans* of antibiotic activity effective against *E. coli* but less so against a tetracycline-resistant *E. coli*.

Finally, it is demonstrated that the synthesis of tetracyclines is directed by LP²127 in the heterologous host *Streptomyces lividans*. This is accomplished in both agar and broth fermentation. Both the originally isolated tetracycline resistant *S. lividans* and a LP²127 transformant of *S. lividans* produce tetracycline and chlortetracycline under conditions where the same products are isolated from the DNA source organism *Streptomyces aureofaciens* ATCC 13899. On the other hand, a *S. lividans* transformant containing only plasmid vector with no inserted DNA shows no antibiotic production.

The demonstration of production of tetracyclines by the heterologous host is not limited to the fermentation conditions or HPLC analytical systems described in the example, although these clearly allow efficient analysis. A large number of procedures for fermentation and analysis of tetracyclines have been described and can be substitued herein. Also, although *Streptomyces lividans* is used as the heterologous host in the examples, the heterologous expression of antibiotic biosynthetic genes is expected in a number of actinomycetes and other bacterial groups including, but not limited by Bacillus, Corynebacteria, Thermoactinomyces, so long as they are transformed with the relatively large plasmid constructions described here. Those that are transformed include such as *Strentomyces ariseofuscus* and *Streptomyces ambofaciens* which are known to be relatively non-restricting.

EXAMPLE 1

PREPARATION OF *STREPTOMYCES AUREOFACIENS* TOTAL DNA

A lyophilized preparation of *Strentomvces aureofaciens* ATCC 13899 is suspended in 0.8 mL of 1× synthetic salts solution (6 g of $Na_2HPO_4$/L, 3 g of $KH_2PO_4$/L, 0.57 g of sodium citrate/L) and plated onto Bennett's agar (1 g of yeast extract/L, 2 g of NZ-Amine A/L, 1 g of beef extract/L, 20 g of D-glucose/L, 20 g of Bacto-agar/L). After incubation at 28° C. for two days, cells from a single plate are scraped into 5 mL of Tryptic Soy Broth (Difco) and sonicated briefly (~10 seconds) with a Heat Systems Ultrasonics W200P sonicator equipped with a microtip. A seed culture is developed by inoculating 2 mL of the sonicated suspension into 50 mL Tryptic Soy Broth (TSB), followed by incubation at 28° C., 200 rpm for 2 days. Five mL of seed culture is then inoculated to 100 ml TSB supplemented with 2% glycine and incubated at 28° C., 200 rpm for 48 hrs.

Cells are harvested by centrifugation at 9800 ×g for 30 minutes. The cell pellet is washed with 200 mL P medium (100 g of sucrose/L, 0.2 g of $K_2SO_4$/L, 2 mL of trace element solution/L which consists of 40 mg of $ZnCl_2$/L and 10 mg/L each $FeCl_3.6H_2O$, $CuCl_2.2H_2O$, $MnCl_2.4H_2O$, $Na_4B_2O_7.10H_2O$ and $(NH_4)_6MO_{724}.4H_2O$). The cell pellet is frozen at −20° C. then defrosted and suspended in 12 mL P⁺ (P medium suppplemented to contain 25 mM TES, 25 mM $CaCl_2$, 10 mM $MgCl_2$, 03.7 mM $KH_2PO_4$) containing 10 mg/mL lysozyme (sigman, 3× recrystallized). The cells are incubated at room temperature for 2 hours by which time protoplast formation is evident. An addition of 2.5 mg of Proteinase K (Boehringer-Mannheim) is made and the mixture incubated at 37° C. for 15 minutes. Lysis is achieved by adding 10 mL 0.2M EDTA pH8, 0.1M Tris pH 8 followed immediately by the addition of 2.4 mL 10% sodium lauryl sulfate (SDS). The viscous mixture is incubated at 50° C. for 60 minutes with occasional gentle mixing.

Once lysis is complete, 20 mL of equilibrated phenol (50 g phenol+6.5 mL of 100 mM NaCl, 10 mM Tris pH8, 1 mM EDTA pH8+0.05 g 8-hydroxyquinoline) is added, the preparation gently shaken and then spun in a table top centrifuge at 1500 ×g for 30 minutes. The aqueous top layer is collected and re-extracted as above; the spent phenol from the first extraction is back-extracted with 20 mL 10 mM Tris pH7.4, 1 mM EDTA pH 8 (TE). The collected aqueous phases are then extracted with an equal volume of chloroform, spun as above and 10-mL portions distributed to separate test tubes. One mL of 3M ammonium acetate pH 5 is added to each and 10 mL of cold ethanol layered on top of the viscous solution. The DNA is gently spooled onto a glass rod, rinsed twice in cold ethanol and dissolved in 8 mL TE overnight at 4° C. An $A_{260}$ spectrophotometric reading is taken as an estimate of total nucleic acids present (predominantly DNA).

EXAMPLE 2

PARTIAL DIGESTION AND SIZE ENRICHMENT OF *S. AUREOFACIENS* DNA

A partial digestion condition that yields Sau3A digestion products of *S. aureofaciens* DNA in the range of 35 kilobases (Kb) is determined empirically. A series of reaction tubes containing ~25 µg DNA contained in 300 µL of reaction buffer consisting of 100 mM NaCl, 10 mM Tris pH7.4 10 mM $MgCl_2$ are prepared, and restriction endonuclease Sau3A (New England Biolabs) added to give final concentrations of 0.5, 0.1, 0.05, 0.01, 0.005 enzyme units/µg DNA. The reactions are incubated at 37° C. for 60 minutes, then placed at 65° C. for 20 minutes and finally removed to ice. Twenty µL is removed and loaded to 0.5% agarose gel for size comparison to fragments of known length (lambda DNA digested with HindIII, XhoI and undigested). The DNA in the remaining volume is precipitated by the sequential additions of 50 µL 3M ammonium acetate and 1 mL ethanol, followed by chilling at −20° C. The precipitated DNA is then pelleted by centrifugation at 8800 ×g, redissolved in 300 µL 0.3M ammonium acetate, similarly precipitated, pelleted, rinsed with ethanol, vacuum dried and.the dried pellet finally dissolved in 100 µL TE. An inspection of the ethidum bromide stained agarose gel which is electrophoresed overnight at 1 volt/cm, reveals that digestion with 0.05 units Sau3A/µg DNA gives digestion products largely in the desired 35 Kb size range.

EXAMPLE 3

PREPARATION OF COSMID ARMS

The components of the bifunctional cosmid vector are retrieved from plasmids A and B shown in FIG. 1. Plasmid A contains pIBI24 which provides an origin of replication and an ampicillin resistance gene for replication and selection in *E. coli*. This plasmid also provides a thiostrepton-resistance gene for plasmid selection in the actinomycetes, as well as multiple cohesive end sites (cos) from bacteriophage lambda which serve as substrates for in vitro packaging. Plasmid B is designed to provide an SCP2* origin of replication for plasmid maintenance in the actinomycetes, and multiple cos sites.

Plasmid A is digested with Asp718 and then desphosphorylated with calf intestine alkaline phosphatase (CIAP). The DNA then is extracted with chlorpane and chloroform, precipitated with ethanol and vacuum dried. The DNA is then resuspended and digested with BglII. Plasmid B is digested with SalI and subsequently treated with CIAP. After chlorpane extraction, ethanol precipitation and vacuum drying, the DNA is resuspended and digested with BglII.

The digestion reactions noted above are loaded to an agarose gel and electrophoresed overnight.

A 6.1 Kb fragment from plasmid A and an 8.0 Kb fragment from plasmid B, which contain the functional regions described above, are isolated from the agarose gel by electroelution.

EXAMPLE 4

LIGATION OF COSMID ARMS TO SAU3A DIGESTED GENOMIC DNA AND IN VITRO PACKAGING

The Sau3A digested and size "inspected" genomic fragments of *S. aureofaciens* DNA are joined to cosmid arms via in vitro ligation. Four µL Sau3A digested *S. aureofaciens* DNA, corresponding to ~8 µg, are combined with 1 µg each of cosmid arms 1 and 2 in a 10 µL ligation mixture that contains 66 mM Tris pH7.4, 10 mM $MgCl_2$, 1 mM ATP, 10 mM dithiothreitol and 40 units (cohesive end unit) T4 DNA ligase (New England Biolabs). The ligation mixture is incubated at 11° C. for 18 hours then subjected to an in vitro packaging reaction by adding the entire 10 µL reaction to a Packagene$^R$ lambda DNA packaging system extract (Promega Biotec). After a 2 hour incubation at room temperature, 500 µL phage dilution buffer (PDB) (100 mM NaCl, 10 mM TRIS-HCl pH7.4, 10 mM $MgSO_4$) is added followed by the addition of 25 µL chloroform. The mixture is vortexed and stored at 4° C.

EXAMPLE 5

TRANSDUCTION INTO *ESCHERICHIA COLI* AND PREPARATION OF A BIFUNCTIONAL COSMID LIBRARY

The phage preparation derived from the m vitro packaging reaction is transduced into *Escherichia coli* X2819T (R. Curtiss), with the objective of obtaining thousands of transductants from which a pooled plasmid DNA preparation, or bifunctional cosmid library, can be obtained. To this end, 0.3 mL of an overnight culture of X2819T is inoculated into 10 mL 20-10-5 (20 g of Tryptone/L, 10 g of yeast extract/L, 5 g of NaCl/L, 50 mg of thymidine/L) and incubated at 28° C., 2.5 hours. Four portions of 0.4 mL X2819T cells are then combined with 0.8 mL PDB and spun in a microfuge at full speed for 5 minutes. The pelleted cells are suspended in 100 µL PDB. Then 50 µL of phage preparation from in vitro packaging is added to each. Phage are absorbed to cells at 37° C., 25 minutes. Two mL of 20-10-5 are added to each mixture and the suspension incubated with shaking at 28° C. for 2 hours. One-tenth mL aliquots are plated onto a total of 50 Petri plates containing 20-10-5 agar (20-10-5 broth and 20 g of Bacto agar/L) supplemented with 100 mg of ampicillin/L (sodium salt-Sigma). The plates are incubated at 28° C. overnight and then left at room temperature for three days. A plate count of five representative plates reveals that a total of ~12,000 ampicillin-resistant colonies are obtained.

Each plate is flooded with 5 mL of solution consisting of 50 mM glucose, 25 mM Tris-HCl pH 8, 10 mM EDTA pH 8 (GTE). The colonies are suspended with a sterile spreader and all eluates pooled to yield a cell suspension which is spun at 9800 xg for 5 minutes. The pelleted cells are resuspended in 72 mL-GTE. Then 8 mL of GTE containing 40 mg of lysozyme/mL is added. The lysozyme digestion is incubated at room temperature for 20 minutes. Then 160 mL of alkaline-SDS (8 g of NaOH/L, 10 g of SDS/L) is added which yields a viscous lysate after gentle mixing. After incubation on ice for 20 minutes, 80 mL of 5M potassium acetate is added, mixed, and incubated an additional 20 minutes on ice. The preparation is then spun at 9800xg for 20 minutes, the supernatent collected and 200 mL of cold isopropanol *added, mixed in and incubated on ice for 15 minutes, followed by centrifugation at 9800 xg for 20 minutes. The nucleic acid pellet is dissolved in 20 mL TE supplemented with 1% sodium sarcosine. Twenty-two grams of CsCl is added, and once dissolved, 2 mL of a solution of 10 mg ethidium bromide/mL is added. The CsCl-ethidium bromide mixture is loaded into appropriate tubes and centrifuged in a Beckman 70.1Ti rotor at 55,000 rpm for 19 hours. The tubes are removed and plasmid band is recovered by syringe side puncture. Ethidium bromide is removed from the sample by extracting 4 times with equal volumes of butanol saturated with water. The aqueous solution is brought to 6 mL with TE; 1 mL 3M ammonium acetate is added and the plasmid DNA precipitated with 18 mL of ethanol. After chilling at −20° C. the DNA is pelleted by centrifugation at 3400 xg for 30 minutes. A second precipitation is similarly performed, then the DNA is rinsed with ethanol, vacuum dired, dissolved in 1 mL TE and the DNA concentration is determined spectrophotometrically.

EXAMPLE 6

INTRODUCTION OF PLASMID LIBRARY INTO *STREPTOMYCES LIVIDANS* AND CONSTRUCTION OF A *S. LIVIDANS* RECOMBINANT CELL LIBRARY

The bifunctional plasmid library constructed in the previous step is transformed into *Streptomyces lividans* TK54 where phenotypic expression of Strertomyces genes is achieved. To this end protoplasts of *Streptomvces lividans* TK54 are prepared is by essentially standard methods (Hopwood et al, 1985). Briefly, the cells from a 45-hour culture of *S. lividans* TK54, developed by inoculating 0.2 mL of a spore suspension into each of ten-50 mL aliquots of complete YEME medium (3 g of yeast extract/L, 5 g of peptone/L, 3 g of malt extract/L, 10 g of glucose/L, 340 g of sucrose/L, 5 g of glycine/L, 5 mM $MgCl_2$, 40 mg/L each L-histidine and L-leucine) are pelleted by centrifugation at 9800 xg for 15 minutes. The cell pellet is washed twice with P medium and then suspended in 60 mL P$^+$. Twenty mL of P$^+$ containing 14 mg of lysozyme/mL is added and the suspension incubated at 30° C. in a shaking water bath at 150 rpm for 90 minutes. Subsequently, 100 mL P$^+$ is added and the protoplast suspension is passed through sterile non-absorbent cotton. The filtrate is spun at 3800 xg for 10 minutes, the protoplast pellet resuspended and washed with 100 mL P$^+$, and after a second centrifugation resuspended in 120 mL P$^+$. The protoplast preparation is distributed to 1.8 mL cryotubes and frozen at −70° C. Transformation is conducted by distributing 0.3 mL of the TK54 protoplast preparation (containing ~1×10$^9$ protoplasts) to each of 4 centrifuge tubes containing 5 mL P$^+$. The protoplasts are pelleted by spinning at 3400 xg for 10 minutes and then resuspended in the residual volume. Approximately 10 µg of cosmid library DNA is added to each, followed by the addition of 0.5 ML of 25% PEG1000 (1 g PEG1000 (Sigma) dissolved in 3mL of a solution consisting of 25 g of sucrose/L, 2 mL 500X trace elements solution/L, 0.25 g of K$_2$SO$_4$/L, 100 mM CaCl$_2$, 50 mM TRIS-maleate pH 8). After mixing and incubating for 30 seconds, 5 mL P$^+$ is added. The protoplasts are then pelleted and resuspended in 1 mL P$^{30}$. One tenth ml volumes are then spread onto dried R$_2$YE agar (100 g of sucrose/L 0.25 g of K$_2$SO$_4$/L, 2 ml of 500X trace elements solution/L, 2g of L-proline IL, 20 g of D glucose/L, 5 g of yeast extract/L, 0.05 g of KH$_2$PO$_4$/L, 25 mM TES, 25 mM CaCl$_2$, 5 mM MgCl$_2$, 20 g of Bacto-agar/L) and incubated at 28° C. At 24 hours each plate is overlayed with 3 mL of soft R agar (formulated as above but without yeast extract, glucose, or KH$_2$PO$_4$ and containing 8 g of Bacto-agon IL) containing 500 µg of thiostrepton/mL and then incubated an additional 12 days.

Approximately 9100 thiostrepton-resistant colonies are obtained. These are collected by scraping colonies from the agar plates into 3 tubes containing 25 mL each 20% glycerol. The colony suspensions are fragmented by sonicating for 90 seconds, pooled, then distributed to 1.8 mL cryotubes and frozen at −70° C. This frozen preparation constitutes the *S. lividans* recombinant cell library.

EXAMPLE 7

ISOLATION OF *S. LIVIDANS* LL535, A TETRACYCLINE-RESISTANT TRANSFORMANT FROM WHICH PLASMID LP$^2$127 IS DERIVED

The recombinant cell library of *S. lividans* is next subjected to a screen for tetracycline resistance. One-tenth mL portions of the fragmented *S. lividans* cell library are plated onto Bennetts agar supplemented with 100 µg of tetracycline/mL. After incubation at 28° C. for 5 days, two tetracycline-resistant colonies are detected. One of these, LL535 (initially designated LL529-2) is chosen for further analysis. The LL535 colony is streaked to fresh Bennetts agar containing 100 µg of tetracycline/mL. Growth is observed after 3 days incubation at 28° C. The growth obtained is scraped into 50 mL TSB supplemented with 10 g of glucose/L (TSBG) and 100 µg of tetracycline/mL and the suspension incubated at 30° C., 200 rpm for 3 days. The LL535 culture is briefly sonicated and a portion distributed to 1.8 mL cryotubes and stored at −70° C. The remaining volume is used to inoculate four 2 liter flasks containing 500 mL each modified YEME medium (as previously described but containing 16 g of glycine/L, 25 mM MOPS and without MgCl$_2$, L-histidine or L-leucine) containing 100 µg of tetracycline/mL. The growth obtained after two days is then processed for isolation of plasmid DNA as previously described except that all volumes employed are four times that of the previous example. The final DNA precipitate is dissolved in 1 mL TE.

A 10 µL portion of the plasmid DNA isolated from *S. lividans* transformant LL535 is subjected to an in vitro packaging reaction and subsequently transduced to *E. coli* X2819T using methods described hereinabove. An ampicillin-resistant transductant (designated LL537 is streaked to 20-10-5 agar containing 100 µg of ampicillin/mL and the growth obtained after a 1-day incubation at 30° C. is used. to inoculate two 500 mL portions of 20-10-5 broth containing 100 µg of amplicillin/mL. After incubation at 30° C., 200 rpm overnight plasmid DNA is isolated again as previously described. The isolated plasmid is designated LP$^2$127; the estimated size of the plasmid is 43 kilobase pairs.

A restriction map is generated for LP$^2$127 by performing single and double digests with restriction endonucleases. The location of cleavage sites for BamHI, BclI, BglII, BsmI, BstBI, ClaI, EcoRI, MluI, NcoI, SacI, ScaI, SphI and StuI (New England Biolabs) are determined by digesting with each enzyme alone and in combination with enzymes that cut at known locations within the vector portion, such as EcoRI, EcoRV or HindIII. Restriction endonuclease digestions are performed by combining 1–2 µg of plasmid DNA 4 µl of a 10× solution of salts that are optimal for the restriction endonuclease being employed and approximately 5–40 units of enzyme in a total volume of 40 µl. The 10× salt solutions employed are as follows: for BamHI, EcoRV and SalI, 1.5M NaCl, 0.06M Tris PH8, 0.06M MgCl$_2$; for BglII and ScaI, 1.0M NaCL, 0.1M Tris pH7.4, 0.1M MgCl$_2$; for BclI, 0.75M KCl, 0.06M Trish pH7.4, 0.1M MgCl$_2$; for BstBI, 0.6M NaCl, 0.06M Tris pH 7.4, 0.06M MgCl$_2$; for ClaI, 0.5M NaCl, 0.06M Tris pH8, 0.06M Tris pH7.4, 0.06M MgCl$_2$; for ClaI, 0.5M NaCl, 0.06M Tris pH8, 0.06M MgCl$_2$; for EcoRi, 0.5M Tris pH8, 0.1M MgCl$_2$; for MluI, 0.5M$^2$NaCl, 0.1M Tris pH7.4, 0.1M MgCl$_2$; for SacI, 0.1M Tris pH7.4, 0.1M MgCl$_2$; and for StuI, 1.0M NaCl, 0.1M Tris pH8, 0.1M Tris pH7.4, 0.1M MgCl$_2$; and for StuI, 1.0M NaCl, 0.1M Tris pH8, 0.1M MgCl$_2$. Double digests are performed with salt conditions compatible for both enzymes, as recommended by the manufacturer. All digestion reactions are conducted at 37° C. except for BclI which is performed at 50° C. and BsmI and BstBI which are performed at 65° C. The incubation time is 60–120 minutes. A 5 µl volume of tracking dye (50% glycerol, 0.1M EDTA pH8, 0.25% bromphenol blue) is added to stop the reaction and to facilitate the subsequent loading of agarose gels.

Figure 2:
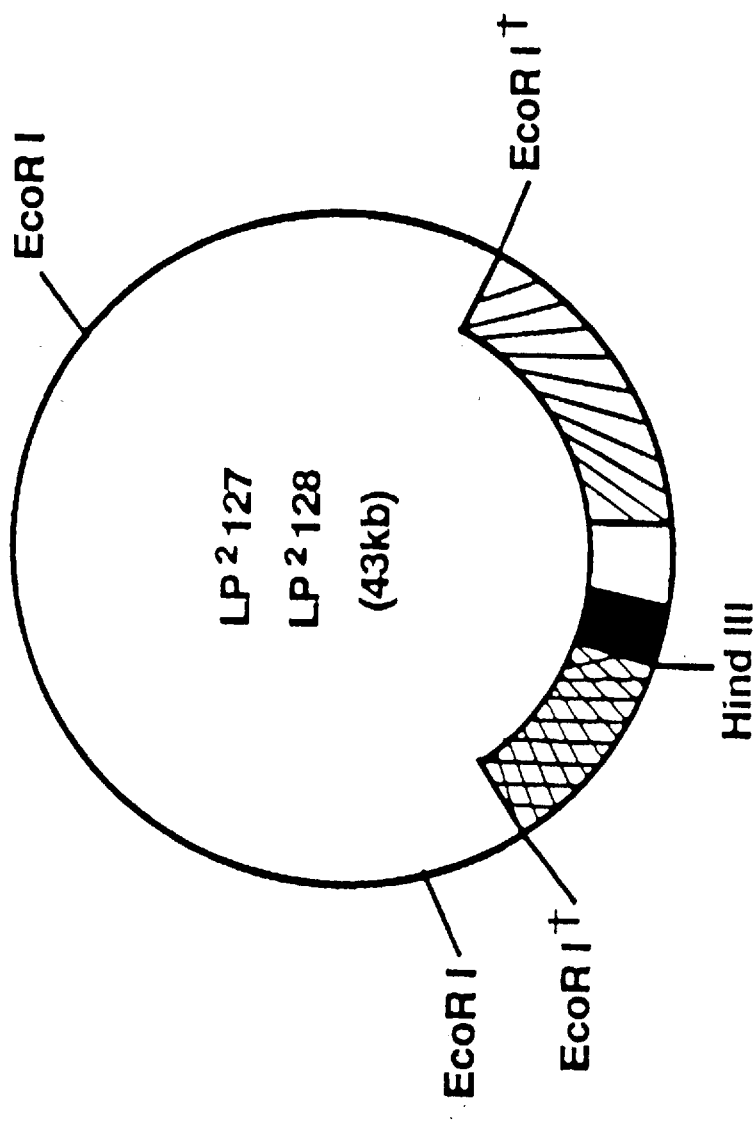
FIG. 2 shows a physical map for LP$^2$127 and LP$^2$128. Both plasmids show equivalent structures by restriction mapping. Therefore, a single structure, representative of both, is shown here and in FIG. 3. The vector portion is represented by double line. The TC/CTC biosynthetic region is shown as a single line. The DNA cloned from *S. aureofaciens* is 31.9 kb; the vector is 11.1 kb. The vector regions denoted are pIBI-24 (hatched), thiostrepton-resistance (striped). The two EcoRI sites marked with a (+) are vector-derived and flank the Sau3A-BglII junction which demarcates vector and *S. aureofaciens* DNA.
Figure 3:
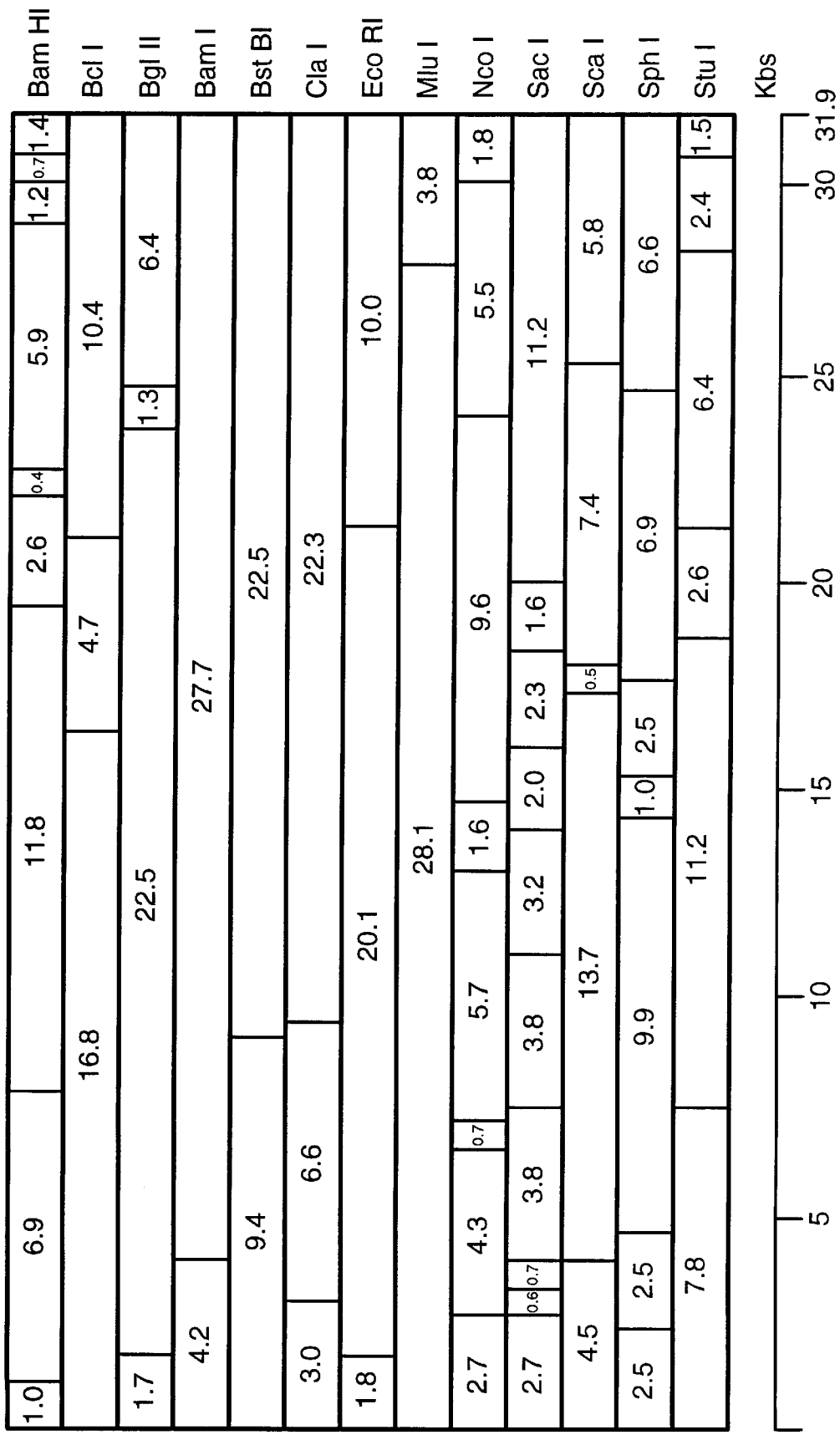
FIG. 3 shows the restriction endonuclease map for S. aureofaciens DNA which is cloned in LP$^2$127 and LP$^2$128. The 31.9 kb of DNA cloned in LP$^2$127 and LP$^2$128 is shown in linear form. The map is drawn so as to include the EcoRI sites derived from the vector as the start and finish positions at the left and right. The sizes of restriction fragments are presented in kilobase pairs and are accurate to within the normal resolution limits of agarose gel electrophoretic analyses (~500 bp).

Digestion results are visualized by electrophoresis through 0.8% agarose gels. The map is assembled by direct digestion of LP$^2$127 as well as by digestion of subcloned fragments. Mapping for BclI and ClaI sites is inhibited by host methylation and, therefore, aided by the use of LP$^2$258, which is obtained by in vitro packaging of LP$^2$127, transduction to *E. coli* GM119 (dam-dcm-) and plasmid isolation by previously described procedures. The physical structure of LP$^2$127 is shown in FIG. 2. A more detailed restriction endonuclease map for the 31.9kb at *S. aureofaciens* DNA cloned in LP$^2$127 is shown in FIG. 3.

EXAMPLE 8

ISOLATION OF *S. LIVIDANS* LL529-TT2, THIOSTREPTON-RESISTANT, TETRACYCLINE-RESISTANT TRANSFORMANTFROM WHICH PLASMID LP$^2$128 IS DERIVED

The isolation of *Streptomyces lividans* LL529-TT2 is performed in a similar fashion to that described for LL535 except that the recombinant *S. lividans* cell library is plated onto Bennetts agar containing 50 µg of thiostrepton/mL and 100 µg of tetracycline/mL. After incubation at 28° C., for 11 days, two resistant colonies are observed. One of these, LL529-TT2 is streaked to Bennetts agar containing both antibiotics. After three days incubation at 28° C., the resulting growth is used to inoculate 50 mL TSB containing 10 µg of thiostrepton/mL and 100 µg of tetracycline/mL. After five days incubation at 28° C., 200 rpm, plasmid DNA is prepared by a minipreparation procedure, which is similar to previously described plasmid isolation procedures up to the isopropanol precipitation step. However, in this case the volumes employed are ~¼ of those previously noted. After isopropanol precipitation, the nucleic acid pellet is dissolved in 1 mL TE and extracted with an equal volume of chlorpane (500 g phenol and 0.5 g 8-hydroxyquinoline equilibrated in a buffer containing 100 mM NaCl, 1 mM EDTA pH8, 10 mM sodium acetate pH 6, plus 500 mL chloroform) by agitating and then spinning in a microfuge at full speed for 3 minutes. The aqueous phase is next re-extracted with chlorpane and then extracted with chloroform in a similar fashion. The final aqueous layer is collected and 100 µL 3M ammonium acetate and 1.8 mL ethanol are added to precipitate nucleic acids. After chilling to −20° C., the precipitation reaction is centrifuged at 8800 ×g for 30 minutes. The resulting pellet is dissolved in 300 µL 0.3M ammonium acetate, similarly precipitated with 1 mL ethanol and centrifuged. The resulting pellet is rinsed with ethanol, vacuum dried and dissolved in 1 mL TE.

The LL529-TT2 plasmid minipreparation is used to perform in vitro packaging as previously described. An ampicillin-resistant transductant (designated LL538) is chosen for plasmid preparation which is performed as outlined in the example for LL535. The resulting purified plasmid is designated $LP^2128$. The restriction band patterns obtained when $LP^2128$ is digested with 20 different restriction endonucleases is compared to that obtained for $LP^2127$ by analyzing the digestion products on the same electrophoresed agarose gel. The gel banding patterns obtained for $LP^2128$ are identical to those seen for $LP^2127$, indicating that the two plasmids are equivalent. Thus, FIGS. 2 and 3 describe the structure of $LP^2128$ as well as $LP^2127$.

EXAMPLE 9

PLASMID $LP^2127$ AND $LP^2128$ CONFER A PLASMID LINKED TETRACYCLINE RESISTANCE

To verify that the tetracycline resistances encountered are plasmid-borne, plasmids $LP^2127$ and $LP^2128$ are transformed into protoplasts of *Strentomyces lividans* and the resulting thiostrepton-resistant transformants are tested for tetracycline-resistance. The procedures for preparation and transformation of *S. lividans* protoplasts and the subsequent selection for thiostrepton-resistant transformants are performed as previously described. Ten µg of both $LP^2127$ and $LP^2128$ are transformed, as well as 5 µg of a tetracycline-sensitive control, $LP^2111$ (a vector consisting of pIBI24, the -SCP2* replication and stability regions and thiostrepton-resistance gene). One hundred and fifty transformants for each plasmid tested are sequentially picked to pairs of Bennetts' agar plates containing 100 µg of tetracycline/mL or 25 µg of thiostrepton/mL.

Growth of the stabs are scored after incubation at 28° C. for 5 days. All the thiostrepton-resistant transformants derived from $LP^2111$ prove to be tetracycline-sensitive, whereas 80% of thiostrepton-resistant transformants tested from either $LP^2127$ or $LP^2128$ are shown to be tetracycline-resistant.

EXAMPLE 10

PRODUCTION OF CHLORTETRACYCLINE AND TETRACYCLINE BY *STREPTOMYCES LIVIDANS* CONTAINING $LP^2127$ AND $LP^2128$

A series of experiments is performed to demonstrate that $LP^2127$ and $LP^2128$ direct the biosynthesis of chlortetracycline (CTC) and tetracycline (TC) in the heterologous host *Stretomyces lividans*. The original isolate LL535, as well as *S. lividans* transformed with $LP^2127$, produce CTC and TC on agar and in broth fermentation, whereas *S. lividans* containing a plasmid cloning vector without inserted DNA does not yield a tetracycline antibiotic. $LP^2128$ transformed into *S. lividans* directs the synthesis of an antibiotic with acitivity against *Escherichia coli* that can be biologically characterized as tetracycline. No such activity is produced by the *S. lividans* host.

Initially, *S. lividans* strain LL535, the thiostrepton-resistant isolate from which $LP^2127$ is isolated, is plated onto Bennetts agar (which contains 25 µg of thiostrepton/mL) at a cell dilution designed to give approximately 200 colonies per plate. *S. lividans* strain LL531 (which contains the previously described plasmid vector $LP^2111$) is similarly plated at a target density of ~400 colonies per plate.

After eight days incubation at 30° C., colonies of LL535 exhibit a yellow UV flourescence when illuminated with a 366 nm UV lamp. This is characteristic of tetracycline producing cultures and is not observed for LL531.

Plates of each then are tested for biological activity by overlaying the colonies with 5 mL soft 20-10-5 agar (8 g of Bacto agar/L) which has been seeded with 0.1 mL of an overnight growth of assay organism. The assay strains employed are *Bacillus subtilis* strain T1325 obtained from the University of Leicester (Dr. Eric Clundliffe) T1325 (which contains a plasmid conferring thiostrepton-resistance), *Escherichia coli* MM294 and MM294 (ATCC 33625) containing pBR322 (which confers tetracycline and ampicillin resistance). The overnights are developed at 37° C. in 10 mL 20-10-5, which is supplemented with 25 µg of thiostrepton/mL for T1325 and 100 µg of ampicillin/mL for MM294/pBR322. Once overlayed and incubated at 37° C. overnight, the plates are examined for zones of inhibition in the lawns of overlay organism. Strain LL531 gives no zones with *E. coli* strains and only a few colonies give small localized zones with the gram-positive T1325. All of these latter colonies show red-pigment which is characteristic of expression of actinorhodin; *S. lividans* is known to express this normally cryptic pathway at observable frequency (Horinouchi et al, 1989). By comparison, strain LL535 shows production of an antibiotic that totally inhibits growth of the T1325 and MM294 in the overlay (In later experiments with fewer colonies per plate, small, discrete and very large zones of inhibition are seen around suitably separated individual colonies with these assay organisms). Colonies of LL535 overlayed in the present experiment with MM294/pBR322 show discrete zones around colonies. This reduced activity effect seen with MM294/pBR322 is taken to indicate a reduced sensitivity owing to the expression of tetracycline resistance resident on plasmid pBR322.

The antibiotic being elaborated on agar is characterized by extracting antibiotic from agar blocks of confluent plate cultures. Strains LL535 and LL531 are grown on Bennetts agar containing 25 µg of thiostrepton/mL; *S. aureofaciens* ATCC 13899, the source of the cloned DNA in $LP^22127$ and $LP^2128$, is plated on Bennetts agar without drug. After five days of growth at 30° C., 1" square agar blocks are cut out and macerated in 3 mL acid methanol (11.5 mL concentrated $H_2SO_4$ in 4 liters methanol). After vortexing for five minutes, the supernatant is filtered through an Acro®LC-25 membrane filter and subjected to HPLC analysis.

The HPLC analyses are carried out isocractically on a C18 reverse phase column with a mobile phase consisting of oxalate buffer at pH 2.9 containing 22% DMF=N.N-dimethylformamide. Flowrate is 1 mL/min and the eluate is monitored at 365 nm. Authentic tetracycline and chlortetracycline are used as standards.

The HPLC chromatograms show that LL535 and ATCC 13899 are producing substances with retention times indentical to TC and CTC. Extracts of LL531 do not show these peaks.

Thiostrepton-resistant transformants of *S. lividans* obtained with LP$^2$127, LP$^2$128 and LP$^2$63 (a plasmid vector consisting of pIBI24 cloned into the SacI site of pIJ702) are similarly analyzed for production of antibiotic by overlay with assay organisms T1325 and MM294. The LP$^2$127 and LP$^2$128 transformants show production of antibiotic(s) active against both assay organisms whereas LP$^2$63 transformants do not, thereby indicating that the ability to produce antibiotic is associated with the *S. aureofaciens* DNA present in LP$^2$127 and LP$^2$128.

Broth fermentations are also conducted as an additional confirmation that the antibiotics being produced by *S. lividans* bearing LP$^2$127 are tetracycline and chlortetracycline. Fifty mL seed cultures of ATCC 13899, LL531, and LL873 (a LP$^2$2127 transformant of *S. lividans*) are developed using S medium (4 g of yeast extract/L, 4 g of peptone/L, 10 g of glucose/L, 0.5 g of MgSO$_4$.7H$_2$O/L) containing 5 $\mu$g of thiostrepton/mL; ATCC 13899 was grown without thiostrepton. After incubation at 30° C. for three days, 0.5 mL seed is transferred to 25-mL fermentations containing 10 $\mu$g of thiostrepton/mL (except no drug with ATCC 13899). After incubation at 28° C. for ten days, 0.5 mL samples of the final mashes are diluted into 4.5 mL acid methanol, processed as previously described and subjected to HPLC analysis. Strain LL531 yields no tetracycline compounds, whereas ATCC 13899, LL535 and LL873 yield 37, 56 and 6 $\mu$g/mL CTC respectively. A small amount of TC also is detected in the fermentation mashes of these three strains.

*E. coli* strains LL537 and LL538 are the *E. coli* transductants from which plasmids LP$^2$127 and LP$^2$128 are isolated and have been deposited, under the Budapest Treaty, in the American Type Cell Culture, 12301 Parklawn Drive, Rockville, Md. and have ATCC accession numbers as follows. *E. coli* X2818T containing LP$^2$127 (LL537) has accession number ATCC 68357, and *E. coli* X2819T containing LP$^2$128 (LL538) has accession number ATCC 68358. Both were filed on Jul. 10, 1990 and are available to the public when legally applicable.

BIBLIOGRAPHY

1. Baltz, R. H. and P. Matsushima. 1981. Protoplast fusion in Streptomyces: conditions for efficient genetic recombination and cell regeneration. J. Gen. Microbiol. 127:137–146.
2. Baltz, R. H. and E. T. Seno. 1988. Genetics of *Streptomyces fradiae* and tylosin biosnthesis. Ann. Rive. Microbiol. 42:547–574.
3. Bibb M. J., J. M. Ward, and D. A. Hopwood. 1978. Transformation of plasmid DNA into Streptomyces protoplasts at high frequency. Nature (London) 274:398–400.
4. Binnie, C., M. Warren, and M. J. Butler. 1989. Cloning and heterologous-expression in *Streptomyces lividans* of *Streptomyces rimosus* genes involved in oxytetracycline biosynthesis. J. Bateriol. 171:887–895.
5. Butler, M. J., E. J. Friend, I. S. Hunter, F. S. Kaczmarek, D. A. Sugden and M. Warren. 1989. Molecular cloning of resistance genes and architecture of a linked gene cluster involved in biosynthesis of oxytetracycline by *Streptomyces rimosus*. Mol. Gen. Genet. 215:231–238.
6. Chater, K. F. and C. J. Bruton. 1983. Mutational cloning in Streptomyces and the isolation of antibiotic production genes. Gene 26:67–78
7. Chen, C. W., H. -F. Lin, C. L. Kuo. H. -L. Tsai and J. F. -Y. Tsai. 1988. Cloning and expression of a DNA sequence conferring cephamycin C production. Bio/Technology 6:1222–1224.
8. Cox, K. L. and R. H. Baltz. 1984. Restriction of bacteriophage plaque formation in Streptopyces spp. J. Bacteriol. 159:499–504.
9. Distler, J., K. Mansouri and W. Piepersberg. 1985. Streptomycin biosynthesis in *Streptomyces griseus* II. Adjacent genomic location of biosynethetic genes and one of two stretomycin resistance genes. FEMS Microbiol. Lett 30:151–154.
10. Duggar, B. M. 1948. Aureomycin: a product of the continuing search for new antibotics. Ann. N.Y. Acad. Sci. 51:171–181.
11. Feitelson, J. S. and D. A. Hopwood. 1983. Cloning of a Streptomyces gene for an O-methyltransferase involved in antibiotic biosynthesis. Mol. Gen. Genet. 190:394–398.
12. Fishman, S. E., K. Cox, J. L. Larson, P. A. Reynolds, E. T. Seno, W. -K Yeh, R. Van Frank and C. L. Hershberger. 1987. Cloning genes for the biosynthesis of a macrolide antibiotic. Proc. Natl. Acad. Sci. USA 84:8248–8252.
13. Gil, J. A. and D. A. Hopwood. 1983. Cloning and expression of a p-aminobenzoic, acid synthetase gene of the candicidin-producing *Streptomyces griseus*. Gene 25:119–132.
14. Goodman, J. J. 1985. Fermentation and mutational development of the tetracyclines. p.5–57. In: J. J. Hlavka and J. H. Boothe (eds), Handbook of Experimental Pharmacology, vol. 78, The Tetracyclines. Springer-verlag, Berlin.
15. Hohn, B. and J. Collins. A small cosmid for efficient cloning of large DNA fragments. Gene 11:291–298.
16. Hopwood, D. A. and H. M. Wright. 1978. Bacterial protoplast fusion: recombination in fused protoplasts of *Streptomyces coelicolor*. Mol. Gen. Genet. 162:307–317.
17. Hopwood, D. A., 1967. Genetic analysis and genome structure in *Streptomyces coelicolor*. Bacteriol. Rev. 31:373–403.
18. Hopwood, D. A., M. J. Bibb, K. F. Chater, T. Kieser, C. J. Bruton, H. M. Kieser, D. J. Lydiate, C. P. Smith, J. M. Ward and H. Schrempf. 1985. Genetic manipulation of Streptomyces—a laboratory manual. The John Innes Foundation. Norwich, England.
19. Horinouchi, S., F. Malpartida, D. A. Hopwood and T. Beppu. 1989. afsB stimulates transcription of the actinorhodin biosynthetic pathway in *Streptomyces coelicolor* A3 (2) and *Streptomyces lividans*. Mol. Gen. Genet. 215:355–357.
20. Jones, G. H. and D. A. Hopwood. 1984. Molecular cloning and expression of the phenoxazinone synthase gene from *Streptomyces antibioticus*. J. Biol. Chem. 259:14151–14157.
21. Katz, E., C. J. Thompson and D. A. Hopwood. 1983. Cloning and expression of the tyrosinase gene from *Streptomyces antibioticus* in *Streptomyces lividans*. J. Gen. Microbiol. 129:2703–2714.
22. Larson, J. L. and C. L. Hershberger. 1986. The minimal replicon of a streptomycete plasmid produces ultrahigh level of plasmid DNA. Plasmid 15:199–209.
23. Leskiw, B. K., Y. Aharonowitz, M. Mevarech. S. Wolfe, L. C. Vining. D. W. S. Westlake and S. E. Jensen. 1988. Cloning and nucleotide sequence determination of the isopenicillin N synthetase gene from *Streptomyces clavuliaerus*. Gene 62:187–196.
24. Lydiate, D. J., F. Malpartida and D. A. Hopwood. 1985. The Streptomyces plasmid SCP2*: its funtional analysis and development into useful cloning vectors. Gene 35:223–235.
25. Malpartida, F. and D. A. Hopwood. 1984. Molecular cloning of the whole biosynthetic pathway of a Streptomyces antibiotic and its expression in a heterologous host. Nature (London) 309:462–464.
26. Maniatas, T., E. F. Fritsch and J. Sambrook. 1982. Molecular cloning: a laboratory manual. Cold Spring Harbor Laboratory, Cold Spring Harbor, N.Y.

27. McCormick, J. R. D. 1968. Point blocked mutants and biogenesis of tetracyclines. p. 163–173. In: G. Sermonti and M. Alecevic (eds), Genetics and Breeding of Streptomvyetes. Yugoslav. Acad. Sci. and Arts, Zagreb.
28. Motamedi, H. and C. R. Hutchinson. 1987. Cloning and heterologous expression of a gene cluster for the biosynthesis of tetracenomycin C, the anthracycline antitumor antbiotic of *Strentomyces alaucescens*. Proc. Natl. Acad. Sci. USA 84:4445–4449.
29. Murakami, T., H. Anzai, S. Imai, A. Satoh, K. Nagaoka and C. J. Thompson. 1986. The bialaphos biosynthetic genes of *Stregtomyces hygrosconicus*: molecular cloning and characterization of the gene cluster. Mol. Gen. Genet. 205:42–50.
30. Reynes, J. P., T. Calmels, D. Drocourt and G. Tiraby. 1988. Cloning, expression in *Escherichia coli* and nucleotide sequence of a tetracycline-resistance gene from *Streptomyces rimosus*. J. Gen. Microbiol. 134:585–598.
31. Sanger, F., A. R. Coulson, G. F. Hong, D. F. Hill and G. B. Peterson. 1982. Nucleotide sequence of bacteriophage lambda DNA. J. Mol. Biol. 162:729–773.
32. Stanzak, R., P. Matsushima, R. H. Baltz and R. N. Rao. 1986. Cloning and expression in *Strentomyces lividans* of clustered erythromycin biosynthesis genes from *Streptomyces erythreus*. Bio/Technology 4:229–232.
33. Stutzman-Engwall, K. J. and C. R. Hutchinson. 1989. Multigene families for anthracycline antibiotic production in *Streptomyces neucetius*. Proc. Natl. Acad. Sci. USA 86:3135–3139.
34. Sutcliffe, J. G. 1979. complete nucleotide sequence of the *Escherichia coli* plasmid pBR322. Cold Spring Harbor Symp. Quant. Biol. 43:77–90.
35. Thompson, C. J., T. Kieser, J. M. Ward, and D. A. Hopwood. 1982. Physical analysis of antibiotic-resistance genes from Streptomyces and their use in vector construction. Gene 20:51–62.
36. van Pee, K. -H. 1988. Molecular cloning and high-level expression of a bromoperoxidase gene from *Strentomyces aureofaciens* Tu24. J. Bacteriol. 170:5890–5894.
37. Vara, J. A., D. Pulido, R. A. Lacalle and A. Jimenez. 1988. Two genes in *Streptomyces alboniger* puromycin biosynthesis pathway are closely linked. Gene 69:135–140.
38. Veselova, S. I. 1969. Combined effect of nitrous acid, ultraviolet light, streptomycin and chlortetracycline on *Actinomyces aureofaciens*. Antiobiotiki 14:698–702.

In the foregoing, there has been provided a detailed description of particular embodiments of the present invention for the purpose of illustration and not limitation. It is to be understood that all other modifications, ramifications and equivalents obvious to those having skill in the art based on this disclosure are intended to be included within the scope of the invention as claimed.

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 30001 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

```
GATCGGCCGA  CGGCTCCAGG  ACAGCCCGGG  CCGTCCCGGC  CCCCGCGGCA  CGGCCCACCC      60
CGCAGCGACC  CCGGCCCGGC  CGCTCCACGG  CCCGCTCCCG  GCCCGCACAC  CTTCCGGGCC     120
CCACTCCGAA  GAATCGGTTC  TCTTGGGCCC  GTCACCGGGC  CCGGGGCGTC  CACCGCACCG     180
CCCGCCGCGG  CCAGCCCGGA  TCGCTCCACT  CATCGGTCAC  TCGCGCCTGT  CGCCATCGGG     240
GGTCAACCGT  GTCAGTCGGC  AACAACCATC  CGTCGGTTCT  CGTCGTCGAG  GACAACGTCC     300
TGCTGCGCAC  GGGCCTGCAG  GCCCTGCTGT  CGGCCGAGCC  CGACCTCGTC  CTCCGCGCCG     360
CCGTCGGCGG  CGTGGACGAA  GCACTCGCCG  TCATGGCCGG  GCACCCCGTG  GACGTCGTGG     420
TGTACGGAGC  GGGCGAGTCG  GTGGCCGACA  CCGAGCGGGG  CCTCGAGCGC  CTGCTCGACC     480
GGGGCACCCG  GGTGGTCGTA  CTGAGCCGGC  GGGACCACCC  CGGCGAGATG  GAGACGTACC     540
TCAGCAGCGG  TGTGCACGCC  TACCTGGCAG  AGGACGCGGC  CGGGGAGTGC  CTCGGCTCGG     600
TGATCCGGGG  CCTGACCTCG  GACCGGGAGC  GGGTCTACAT  CATGGCCTCG  CGCTCCGGCC     660
TCGACTGGAT  GGCCGGCCAG  CGCGGCAACC  GCCTGTCCGG  ACGCGAGCGG  GAGGTCATGG     720
GCCTGGTCGC  GAACGGGCTG  AGCAACTCGG  CCATCGCGGG  CCGGCTCTGC  ATCTCGCCCG     780
```

```
GCACCGTCAA  GCGCCATCTC  CGGAACGTGT  TCGTCAAGCT  CAACGCCGTC  TCCCGGATCG   840
ACGCCGTGAA  CAAGGCCCGG  GCCGCTTCCA  TGCTGGTCCC  GGCCGGCCGG  GCCTGAGCCC   900
CGCGGACCGG  TCCGGCGCGG  ATCCGTCCGC  GGTGGACCGG  TCCGGCGCGG  ACCCCTGCGG   960
GGACGACGGC  CCGGCAGGGA  GCGGAGCAGG  GCTCGGCCGG  GACGGGCCTC  AGGCCGAACG  1020
GGCCCGCAGG  CCCTGCTCCA  TCGCCCGCGC  GGCAAGCGCC  TGGAACTCCT  GCCGAGTGGG  1080
CGACGTGCCG  CTGAGCAGGT  CGTTGTGCAG  CTCCTGCAGC  GGTCGGGAGG  GGGCGATGCC  1140
GAGGTCCTCG  TCGAGCCGGC  GGTAGAGCAC  GCGGTAGACG  TGCAGGGCCT  CGCTCCGCCG  1200
CCCGGCGCGT  CCCAGGGCGA  GCATGAGCTG  CTCGTGGTAC  CACTCGTTCA  TCGGCTGGTG  1260
CAGGGTCAAC  AGTCTGAGTT  CGGGGATGAG  TTCCCGGTGG  CGCCCGAGCT  GCCGGTCGGC  1320
CAGGATGCGG  TGCTCCAGGG  CGCGCAGGCG  CATCTCCTCC  AGGACGGCGA  CGTGACCGGC  1380
GAGCGGAGCA  CCCCACCGGG  ATGTCCGCCA  GGCGGTGCCC  CGCCACAGGT  CCAGCGCCTG  1440
CCGCAGCCGC  TGGGCGGCCG  CCTCGGGGTG  GCCGGCGGCC  AGCAGCCGGT  CCCCCTCGTG  1500
GTGCAGCCGC  TCGAACTCCT  GGGCGTCCAG  CTCCTCCTCC  CCAGCAGCA   GCACGTAGCC  1560
GGGGGCCTTG  GTGAGGATGA  CCTCGCGGCC  CAGCGGACGG  CAGAGCTTGC  GCAGTTGGTA  1620
GATGTACGTC  TGCGCGGTGG  TGACCACCGT  GCGTGGCGGG  CTGCTGCCCC  AGATCTCCTC  1680
GATGATGAGG  CCGAGGTCCA  CGATCCGGTT  CGCGTTCATG  AGCAGGACCG  CCAGCGTCCA  1740
GCGGACCTTC  AGCGCGCTCG  GGTACACGG   AATTCCCTTG  TCGAGGACTT  CCAGCGGACC  1800
CAGAATGTTG  AACTTCACCA  TGCCTCCGAT  GTCGCTCGGA  TTCCCTCGGC  CCCAGGTATA  1860
TCCGGGTCCG  CGGACGGGTC  TCAAGAGGAA  TCCGCACAAG  GTGGCAGGCG  CGCAATTCCA  1920
AGGTGGCACC  GACGCATTTC  CAGAGCGGTC  CGGCTCCCTG  TCCCGAGGGA  AACACCCCCG  1980
CCGACCGACC  CCCGCCGATC  GGCTGGCGGA  TCGACAAGTC  CTGTTAGGGT  GGGGGCGGTT  2040
GGCCCCATGG  GCCGGGCACC  AGTCACCTGA  TACCCGCGAG  ACAGAGCCAC  GAGGAGAAGG  2100
ACGTGCCCCC  GAAAGATCCG  TGTTGCTCCG  GTAATCCGTA  CGAAGACCGC  AGAACTAGGG  2160
GACACACGTC  TTGACAACCG  TGAACATCGG  AATCCTGGCC  CATGTCGACG  CCGGTAAGAC  2220
CAGCCTGACC  GAGCGACTGC  TGCACACCGC  CGGCGTCATC  GACCGGGTCG  GCAGCGTCGA  2280
CCGCGGCGAC  ACCCAGACCG  ACTCGCACGA  ACTCGAGCGC  CAGCGCGGCA  TCACCATCCG  2340
GTCCGCGGTG  GTGTCCTTCA  CCGTGGGCGA  CGTCAAGGTC  AACCTCATCG  ACACCCCCGG  2400
CCACCCGGAC  TTCATCTCCG  AGGTGGAACG  GGCCCTCGGC  GTGCTCGACG  GCGTGGTGCT  2460
GGTCATCTCC  GCCGTGGAGG  GCGTACAGGC  CCAGACCCGG  CTGCTGATGC  GCACGCTGGT  2520
GAAACTGCGC  ATGCCGGTCA  TCCTCTTCGT  CAACAAGATC  GACAGGATGG  CGCGCGCTA   2580
CCACGAGCTC  CTGGACGAGA  TCCGCTCCGA  GCTCACCCCG  GCCGTCGTCG  CCCTGACCCG  2640
GGTCGAAGGG  CCGGGCACCC  CCGGAGCACG  GGCGTTCGCC  CGGACCGTCG  GGACCGACGA  2700
CCCCGACTTC  GCCGCCGAAC  TGGCCGACGT  CCTGGCCGAG  CACGGCGACG  ACTTCCTGGC  2760
CCGCTACCTC  GAGGACGAGA  CCTCCCTGAC  CGCGCAGGAC  TACAGCGCGG  AACTCGCCCG  2820
CCAGGCGGCC  CGGGCCCAGC  TCTACCCGGT  GCTCTTCGGC  TCGGCCGTGG  CCGGCGCCGG  2880
CATCGATGCC  CTGGTCGACG  GGATCACCAG  GCTGTTTCCG  GTCAATCACG  GCGGCTCCGG  2940
GGGCACCCTC  CGCGGTACCG  TGTTCAAGAT  CGAGCGCGGG  TGGGCGGGCG  AGAAGGTCGC  3000
CTACGTCCGG  TTGCACGGGG  GCGAGCTCGG  GTCGCGGGAG  AAGGTGTCCG  TGTTCGGCG   3060
CGACCAGCAC  GGAGCCGTCA  CCGAGATTCC  CGGCCGCACC  ACGGTGGTCG  AGGTGTTCGA  3120
CCGGGGCTCG  GCCGTCGTCG  AGTCGCGGGC  CCGGGCCGGG  GACATCGCCA  AGGTCTGGGG  3180
```

```
GCTCAAGGGC  ATCCGGATCG  GCGACCGGCT  CGGTTCGGCC  GAGGGGCTGG  ACGGGGAGCA   3240
CCTGTTCGCG  CCGCCGAGCC  TGGAGACCGT  GATCCGACCC  TCCCGGCCCA  GCGCGATGCC   3300
CGAACTGTAC  GACGCGCTGC  TGCAGTTGGC  CGACCAGCAC  CCGTTCATCA  ACGTCCGCAA   3360
GGACGACGAG  GAGCAGGAGA  TCGCCGTCTC  GCTCTACGGT  GAGGTGCAGA  AGGAGGTCAT   3420
CGCGGCCACG  CTCGCCGACG  AGTTCAAGCT  GGACGTGGCC  TTCGAGGGCA  CCCGGATCAT   3480
CTGTGTCGAG  CGCCCGATCG  GGGTCGGCGA  GTCGGTGGAG  GAGATCGACT  ACCGGAGCAA   3540
GACCTTCTTC  TGGGCCACGA  TCGGCCTGCG  GGTGGAACCC  GGGGAGCCGG  GATCAGGGGT   3600
CGTGTTCCGC  CGCTCGGTGG  AGCTCGGCTC  GCTGCCGCAC  GCATTCCACA  AGGCCGTCGA   3660
GGAGGCCGTG  CGGGCCACCC  TGCAGCAGGG  GCTGAACGGC  TGGGAGGTGC  TGGACATCCT   3720
GGTGACCCTC  ACCCGTTCCG  GGTTCGCCAG  CCCGGTGAGC  GCGGCGGGCG  ACTTCCGCAA   3780
GCTCACGCCG  CTCGTGCTGA  TGAACGCGCT  CAAGCAGGCG  GGCACGCAGG  TGTACGAACC   3840
GGTCAACCGC  TTCGAGCTGG  AGGTGCCGGG  TGAGAACGCC  AGCGCCGCCC  TGCTGAGCCT   3900
GGTGGAGTGC  GGCGCCACCC  CGGAGAGCAC  CCGGGGCCTG  GCAGCAGCT   GCCTGGTGGA   3960
GGGGACGATC  CCGGCCCGCA  CGGTGCAGGA  GTTCGAGCAG  CGGCTGCCGG  GCCTGAGCCA   4020
GGGCCAGGGC  GTGCTGGTCA  CCCGGTTCCA  CAGCTTCCAG  CCGGTGGTCG  GGGCGGCGCC   4080
GAGGCGGCGG  CGGACCGACC  TCAACCCGGT  GGACCGCTCG  GAGTACATGC  TGCGGGCCTT   4140
CGGCGGGATC  TGACGGGACG  TCGCGAAAGT  GAGGGCCCGA  CCACCGTGAC  GGTGGTCGGG   4200
CCCTCAGCCG  TGGCGCACTC  CGTCCTCAGT  CGAGCAGTGC  CACCGCTCGC  GTCCAACCCG   4260
CCCCCGCCCC  GGCGATCTTG  ACCGGGAACG  CCTGCACGGT  GAACCCGGTC  GGCGCGGGCA   4320
GTGCGCCCAG  ATTGCTCAGA  CGCTCGATCT  GGCAGTACTC  CCGCTGCCGC  CGCGAAATGC   4380
GCGGGCCACA  GCACGGAACG  GTCGCGGGTG  CGCTGGAACT  CGGCGAGCAT  GTGCGTGAAC   4440
GGAGCGTCCA  GCCCGAAGCG  TCCGTCCCGA  TGAGCCGCAC  GCCGAGGTCG  AGCAGAAGGT   4500
TCGTCGCCGC  CCCGTCCAGG  CCCGCGAACC  GGGTGAAGTA  CTCGGGAGTC  CCGGCGAGTC   4560
GTTCGGCACC  GGTGTGCAGC  AGCACGATCT  CCCCGGCGCT  CGGCCGGTGG  TCGATCTCGT   4620
CGAAGGCGCG  CCGCAGCCGG  TCCACGCCGA  CCGTCCCGAC  CCCGCAGTCG  GTGAGGTCCA   4680
GCCGGACGCC  CGGCCCGATG  AACCATTCCA  GCGGCAACTC  GTCGATGTGG  CGCGGCACTC   4740
CGTAGGCGGC  CCTGCTGCCG  TAGTGGGAGG  GTGCGTCGAC  GTGCGTGCCG  GTGTGGGTGG   4800
TCAGGGTCAG  GGTGTCCAGC  GAGAGCAGTT  CCCCGTCCGG  CAGGTCCGCG  ACGTCGAACT   4860
CGAGGCCGTG  GTCACGGAGC  ATGCCCTCGG  CCATGTGGCG  CGCGCCGTCG  GCCGGCGTCA   4920
GCACCTCGTG  GCGGATGCCG  TCCACCTCCC  AGGCGTTGGC  GTCGATCGTC  GAGGAGAGGT   4980
CAATGAGGCG  CATGCGCGGC  TCCTTCCGGC  AGCAGGGCGC  AGTCCCGCAG  GACGTCGAGG   5040
CAGCGCTCCG  GCCCCGATC   CCGCGCGGCG  AGGTGGCCGT  CCGGCCGGAT  CAGCAGGAAC   5100
TCCCCTGGTG  CCAGGCCGAG  TTCGCGGCGC  AGAATACCCC  CGGGGTCGGG  CAGCTCGCCC   5160
GGGGCTCCGG  GGTCGGCGAC  GGTACGGACG  GAGACGGCGG  AGCCGAACAG  CCGCTCCACC   5220
CGGGCGAGCG  CCTCCCGGTG  CCCGGTGCTC  CCGCCCTCGG  CCGGGGTGGC  GAGCAGGGTC   5280
CAGCGGGGGT  CGGCGAGTTC  GGCGCAGAGC  GCGGACCAGC  CGGGGTGCCC  GGCGGCCGTC   5340
CGGGCGTCGC  AGCCCACCCG  GTCCCCGGGG  GAGGGCCGCC  CGGCGCGCGA  GCCGGCCGGG   5400
CGGGTGAGCG  GGCTGTCCGG  GTAGCCGAGG  GCCAGTCCGC  AGAAGCCCG   GATCATCCGG   5460
CCCTCGACCT  TGCGCCGCAG  CGGCGTGATC  CGGCGCAGCG  CCGCGGTGCC  CACGGTCAGC   5520
AGGGCCGGGG  CCAGCGCGGT  GCGCAGCGAC  ACCAGGGCGG  TGGCCGTGCG  GGTGGAGCGC   5580
```

```
AGCAGCACGG CCCCGGTCGG GACGCGCTCG GCGTCGTAGC TGTCCAGCAG GGCGGGCCCG    5640
GCGTGGCCGC GGATCACGTC GGCGAGCTTC CAGGCGAGGT TGTAGGCGTC CTGGATACCG    5700
CTGTTCATGC CCTGCCCGGA GGCCGGGCTG TGGACGTGGG CGGCATCCCC GGCGAGGAAG    5760
CAGCGGCCCT CGCGCATCCG GGTGATCTGG CGTTGCTGGA CGGTGAAGAC GGAGAGCCAG    5820
GTCGGGGTGC CGACCTGACG GGGCGCCCGA GCGCCGGCC CGATCTTGTC GGCCAGGCGG    5880
CGGCGGACCA GCTCGCGGTC CTCGGCGCCG TCGGTGTCCA CCGTGTCCAC CACGCGCCAC    5940
TTGCCGGGCT CGGGGAACGG GACGAGCAGC AGGGTGCCGG GCTCGGTGTG CAGCAGGTGG    6000
TTGCTGTCCG GCGGGAGGTC GGCGTCGAGG GTGACGTCGG CGTTGAGCCA GACCTCGGTG    6060
GAGTCGCCGA TCAGGCGCAT CCCGAGCTGC TTGCGCACGG TGCTGCGGCC GCCGTCGGCG    6120
CCGACCAGCC AGGGCACCCG GGTCTCCTCG GTGCGCCCGT CGGCGTGGCG GAGGGTGACG    6180
AGCACGGAGT CGGGCCCGGG CTGCAGCGCG GCGAGTTCGA CGCCCCATTC CACGGGGACG    6240
CCGAGTTCGG CGGTGCGCTC GCGCAGCACC TGCTCGGTGA CCACCTGGTC GACCATCAGG    6300
CTGAACGGGT AACGGGTCGG CAGTGAGCGG TAGTTGGTGT CGAAGCGGAT GAGGGTGCGG    6360
CCCCGGCGGT GCATGGTGAA GTGGGTGACC CGCCGGCCGA GCGGCAGCAG CCGGTCGAGG    6420
GCGCCCATCT GCTCGAGCAC CTCCATGGTC CGGGCGTGCA CCGCCAGGGC CCGGCTGCTG    6480
GTGGCCGGGG CCGGGCGCGG CGTCGACCAG CCGGACGGGA ACGCCCCGCG CCTGGCGAGT    6540
TCGTGGGCCG CGGTGAGGCC GACCGGGCCG GCCCCGCGA TCAGGACGGC CGGAGCGGGG    6600
TCAGCCACGG CGTTCCTCGG CGAAGCGCTT GGCCAGGCCG AGCGTGGCGC GGCTGTTGCC    6660
GCCGGCGGCC TCGCGGATGA AGCGGCGGGC GGTGGCGGCG GTGGCGTCCG GGCCGAGGAC    6720
GGTGGGGACC GCCTCGGGGT TGAGGACGAC GGCGTGCCAG GAGGTGACCC GCACTCCGCG    6780
GTCGGTCGAC TCGACGGTCC AACGGCCGGT GTGGGCGGCC ATCATGGAGG GGGTGCGCAG    6840
CTGCTTGTAG GCGATGCCGG ACTCCGGGAA GCAGATCCGG ATGGACTCGG TGGTGTGTTC    6900
GGAGCCGTCG GCGGTGCGGG TGTCCATGGA CATGTGCTGG ATGCCGCCGG CCTCCTCGCG    6960
CAGGTCGAGG CGGGCGACGT GGGGCAGCCG GGCGGGCCAG GCGGCGGCGT CCCGCAGGAA    7020
GTCGTAGACG GCCTCCGGGG CGGCGTCGAC CAGCACCGAG TCCTCGAACT CGAACTCGAA    7080
CTCGGCGAGC CGGTTCCAGC GTTCGGCGAG GTCCTTGATG CCGGCGAGCT CGCTGCGGCT    7140
GTTGCGGTCC GTCGCCTCGC TGATCCAGCG CAGGCCCTGC GGGTCGTCGT CGAGCGCGCT    7200
GAACTCGTGG GTGAGGGTGA GGGTGGTGCC GCCGGGGCGC TCGGCGACCT GCCACTCCCC    7260
CGCCATCGAG GCGACCGGGG CCGAGGAGGC CTCCTGGCGG AAGCGGATCC GGCGCAGGTC    7320
GGCGTCCAGG TCTCGGCGGG ACGTCCAGTG CTTGACCTCG CCGTTGGCCC GGGCCCAGAT    7380
CCGCAGGCGC TCGGCGCCCG GCCCCAGCTC CTCGCGCTCG ACGTGGAGGG TGGGGGCGAA    7440
GCGCCGCGGC CAGGCCAGGG CGTCGGCGAT GACGGTGTAG ACGACCTCGG CGGGGCGTC    7500
GACGTCGATC GAGTGGGTGG TGTGCTGGAT GGTGCTCATG GGTGGGACCG GCCCTTTCCG    7560
TCGGCGGGGT GAAGTTCGGC GGGGTGCGTG GGGTGCGGCT CAGTAGATGC CGAGGCCACC    7620
GCAGACGTTG ATCGCCTGCG CGGTGACCGA CGCGGCGTCG GGGTGGTCA GGTAGTCGAC    7680
CATGCCGGCG ACCTCCTCCG CGGTGGAGTA GCGGCCGAGC GGGATCTTCT GCTCGAAGCG    7740
CGAGAGCACG TCCTCCTCGG TGGTCGCCCA GGTCGCGGCG TACGCCTGGC GGACCCGCAC    7800
GGCCATCGGC GTCTCGACGT AGCCGGGGCA GACGGCGTTG ACCGTGGTGC CGGTGTGGGC    7860
GAGTTCCTTG GCCAGCGCCT TGGTGAAGCC GATGACGCCG GCCTTGGAGG CCGAGTAGGG    7920
GGCGCCCAGC GGGACACCCT GCTTGCCGCC GGTGGAGGCG ACGCTGATGA TCCGCCCGTG    7980
```

```
CCCGGCCGCC  TCCATGCCGC  CGGTGGTGAG  GACCTCGCGG  GTGACGCGGA  AGACGCTGGT   8040
GAGGTTGGTG  TCGATCACGT  CCTGCCACAG  CTCGTCGGTG  AGGGTGGAGG  TGACGCCACC   8100
GCCGTTGCGT  CCGGCGTTGT  TGACCAGCAC  GCCGATCGCG  CCGAAGCGGT  CCACCGCCGC   8160
CCGGACGAGC  CTGCTCACGT  CCGGCGCGGA  GCGGACGTCG  GCCGCGAGGC  CGTCCACCTC   8220
CAGGCCCTCG  CCGCGCAGGC  GGGCGACCGT  CTCGGCGACG  CCCTGCGCGG  TGCGGGCGCA   8280
GATGAAGACG  CTCAGCCCGC  GCCGGGCCAG  CCGCTCGGCG  CTGGCCAGTC  CGATGCCGCT   8340
GGTCGCCCCG  GTCACCAGGG  CGACGTCGCC  GGTCGTCACG  GTGCTCATCG  CATCGATCTC   8400
CTGTCTCGCT  CACGGATCGC  GGGCCCGGCG  GGCCCGCCGG  TCGGGCCCG   CCCCGCGCC    8460
CCGTCGGGAA  CCCGGGGGGA  CAGGCCCCGG  GCCGACCCTG  CCCGGACGGC  TTCGACTGCG   8520
GTTCGAGCGC  GCCGCACACG  CCGACCGCTC  CAACGGGATT  CGAAGCGCGG  GTGGGAGCGT   8580
CGGCGCTGCC  CAACCACCGA  CGCAACGAGG  AGGCCCGGAG  CATGACCGGT  TCGCTCTACG   8640
AGGAGGTCCA  GCACTTCTAC  GGGCGGCAGA  TGCGCCACCT  GGACGAGGGT  GAGGTCACCG   8700
AGTGGGCCGC  GACCTTCACC  GAGGACGGCG  TGTTCGCCGC  CAACGCCCGC  CGCACCCGC    8760
AGGAGGGGCG  CGCGGCGATC  GAGCAGGGCG  CCCGGGAAGC  CGCGCAGCGC  CTGGCCGATG   8820
CCGGAATCCG  GCACCGGCAC  TGGCTGGGGA  TGCTGGAGGT  CGCCGCGCAG  CCGGACGGCC   8880
TGGTGCTCGC  CAAGACCTAC  GCGCTGATCG  TCGCGACGCC  CAAGGGCGGG  CCGGCCGCCG   8940
TGCACCTGAG  CTGCAGCTGT  GAGGACCAGC  TGGTGCGCGT  CGACGGCGAG  TTGAAGGTCC   9000
GGCACCGCCG  GGTGCACCGG  GACGACCTGC  CCGCCTGAGA  GGAGGCCACC  GTGGACCTCC   9060
CACGGGACAG  TACGACCTTC  GGTCCGCCGC  TGGACGTGGT  GGCGGAGCTG  ATCGGCGGGC   9120
CCCGGATCGA  CGACCTCGTC  CGTCGCGCGG  CTGAGCTGAC  GCCTCGTCAT  GTAGCTCTGG   9180
TGCACGGTGA  CCTGGTGCTC  GACCACGCCG  CGCTGGAGGC  CCGGGTGAGC  GACTGCGCCG   9240
AGGCGCTGCG  CGCCGCGTTC  GGCGGTCCCG  GCACGGTCAT  CGCGATCGCC  GCCGAACTGA   9300
CCGTCGACTT  CGCCGTCACC  TTCCTGGGCA  TCTCCCGCTC  CGGGAACACC  AGCGCCATGT   9360
TCAACCCGCT  CGTCCCGGAC  GACACCCTGG  TGCACGTCCT  GAACTCCTGC  GGCGCCCGGG   9420
CGGCCGTGCT  GTCGCCCCGG  ATGCACCGCC  GTGTCCTGGC  CCTGCGGGAC  CGGCTGCCGC   9480
TGCTGCGGCA  ACTGGTGGTG  ACCGCCGACG  CGCTCGACGG  CACGCCCGTC  CTGGACGCCC   9540
TGGAGCGCAC  CGCCGTCCCG  GCCGGCGAGG  TGGTGGAGAC  CGCCTGCCTG  CAGTTCACCA   9600
GCGGCACCAC  CGGCGCGCCG  AAGACCGTCC  GGCTCAGCCA  CCGCAACCTG  CTGGTGAACG   9660
CGGCGCAGTC  GGCGCACGCC  CACCGGCTGA  CGGCCGACGC  CGTCTCGCTC  AACAACCTGC   9720
CCTCCTTCCA  CCTGATGCAC  CTGAACACCG  CGCTCGCGGT  CGGCGCGACG  CACGTGCTCT   9780
GCCCGGAGGA  GGACCGCGCG  GCGCTGGTGG  GACTGGCCCG  TACCTGGCGG  GCCTCGCACC   9840
TGTACAGCCT  GCCGGTGCGG  TTGTCCCGGC  TCGCCGGGGA  CGAGCGGCTG  CCCGGCTTCC   9900
GCATCCCCTC  GCTACGGGCG  GTGCTGTCCG  GTGGATCGGC  GCTGCCGCCC  CGGACGACGA   9960
CCGCCCTGCA  GGAGCACTTC  GGGGTGCCGG  TCGTCCAGGG  CTACGGCCTC  GCCGAGACGT  10020
CCCCGTCGAC  GCACTTCGAC  CTGCCCGAGG  GGCCCACCCT  CGGCTCCAGT  GGGCCCCGG   10080
TCGCCGGGAC  GGCCTGCCGG  ATCGTGGACG  TGCGCACCGG  CGCGGTGCTG  CCGGTGGGCG  10140
AGCGCGGTGA  GATCCAGGTC  CGGGGCCCGC  AGTTGATGCT  GGGCTACCTG  GGCGACGGGC  10200
CCACCGACGC  CGTCGACGCG  GACGGCTGGT  TCCGCACCGG  TGACGTCGGC  CGGATCGACG  10260
AGGCCGGCCG  CCTGTTCGTC  GTCGACCGGA  TCAAGGACGT  CTTCAAGTGC  GACAACTGGC  10320
TGGTGTCGCC  GACCGAGATC  GAGCGGGTGC  TGATGCGGCA  CCCGGCCGTC  GCCGACTGTG  10380
```

```
TGGTCTTCGA  CCAGCCCGAC  GAGCTGAGCG  GCGCCGTCGC  CGTCGGCCTC  GTCGTGCCGC    10440

GCGGCGAGGG  CGTCGACCCG  GCCGCCCTGG  CCGCGTTCGC  GAACGCCCGG  CTCCCCTACT    10500

ACGAGCACCT  GAAGCAGCTG  CGCCTGGTGG  AGGGCATCCC  GCGCTCCGCC  ACGGGCAAGG    10560

TCCAGCGGCG  CGAGCTCCGT  GACCGGCTGT  TCGGCTCCCT  CTGACCCGCA  CCACCCCACC    10620

CGTCCGACCC  ACCACAGGAG  GAACACCGTG  TACACCTTCA  TCAACCGTTT  CACCGTCACC    10680

GGGGACGTCG  CCGAGTTCGA  GACGCTCGTC  GGCGAGATCA  GCGAGTTCAT  GAGCGGCCGG    10740

CCCGGCTTCC  GCTCGCACCG  GCTGTACCGC  TGCGCCACGG  ACGCCTCGGT  GTACGTGGAG    10800

ACCGCCGAGT  GGGACGACGC  GGCCTCGCAC  CGGGCGGCGA  CCGGCTCGCC  GGAGTTCCGC    10860

GCCCGGGTCG  GCAAGGTGAT  GAGCCTGGCC  AAGGCCGAGC  CGGCCCCGTT  CGACCTGCTC    10920

GCGCAGCACG  GCGCCTGAGA  GGGGGAGCAC  CATGACGGAC  AACGGCGAGA  TCATTGCGCA    10980

GCCGGTGATC  CAGCTGCGCG  AGCTGGGGCT  GGCGGCGGCC  GGCGCCGCCG  CCGTGCGGGC    11040

CGCGGCCCGG  CTGGGCCTGG  CTGACGCCCT  GGGCGAGGAG  CCCGCCGGCG  CGGCCGAGCT    11100

GGCCCGGGCC  GTGAACGCGG  ACCCGGACAC  CCTGCAGCGG  CTGCTGCGCG  CCCTGGCCTG    11160

CTACGGCGTG  TTCGCCGAGC  AGCCGGACGG  TCGGTACGTG  CACACCGGCG  CCTCCCGGCT    11220

GCTGCGCGAG  GACACCCCGC  GCAGCCTGAA  GGACATGGTG  CTCTGGGGCA  CCGAGCCGTG    11280

GACCTGGGAG  CTGTGGGGCC  ACCTCGACGA  GGCGGTGCGC  ACCGGCAAGG  CCGTCTTCCC    11340

CGAGCTGCAC  GGCATGGACT  TCTTCGACCA  CCTGCACGCC  CACTCCCCCG  AGTCGGCGGC    11400

CGTGTTCGAC  CGGGCGATGA  CCCAGTCCAG  CCGGCTCTCC  GCGCTCGCGT  TGGCCGACCG    11460

GCTGGACCTC  GGCGGGGTCG  GCACGGTGGT  GGACATCGCC  GGTGGCCAGG  GGCACGTGCT    11520

GGCCACCCTG  CTGGAGCGCA  ACCCCGGTCT  GCGCGGCACC  CTGCTGGACC  TGCCCGAGGT    11580

CGTCTCCGGG  GCCGACGCCC  GGCTGCGGCC  GGGCGGTGCG  CTGGCCGGGC  GCGCCACGCT    11640

GCTCGGCGGC  GACTGCCGGC  GGGAGATCCC  GGTGCAGGCC  GACGTCTACC  TGCTGAAGAA    11700

CATCCTGGAG  TGGGACGACG  AGAGCACCGT  CCTGACGCTG  CGCAACGTCG  TCCGGGCGGC    11760

TGCTCCGGGC  AGCCGGGTGA  TCGTGGTCGA  GAACCTGGTG  GACGGCAGCC  CCGAGCTGCG    11820

GTTCACCACG  GCGATGGACC  TCCTGCTGCT  GCTCAACGTC  GGCGGCCGCA  AGCACACCAG    11880

GGCCGGCCTG  GTCTCGCTGA  TCGAGGAGGC  GGGCCTGACC  CGGGCCGAGG  TCCGTCCGGT    11940

CAACTCCTAC  CTGCACCTGG  TGGAGAGCGT  GGTGCCCGAA  CGGGGCTGAC  CCGCCCGCCC    12000

ACGGCCGCCG  CCCCCGGACC  CGTCCGGGGG  CGGCGGCCGT  GCTGGTCCGG  GGGCGGCGGC    12060

CCTCGCACTG  TCCGGGGGCG  GCGGTGAGCC  CTCGGCACGG  CCGACGGGGC  TCGGGGGGGC    12120

GGAACGGGAA  GGGGAGCGGG  GTCAGATGCC  CTCGGCGAGC  CGCTTCACCG  CCTGCTCGAC    12180

CCGCTCGTCG  GTCTCGGTGA  CGGCCACCCG  CACGTGCCGG  GCGGCCGCAG  CGCCGTAGAA    12240

CTCACCGGGC  GCCACCAGGA  TGCCGCGGTC  GGCCAGCGCA  CCGACGGTCG  TCCAGCACGG    12300

CTCGTCCCTG  GTCGCCCAGA  GGAACAGCGC  ACCGGCCGAG  TGCTCGATCC  GGAAGCCGGC    12360

GTCCACCAGC  GCCCCGCGCA  GCAGCTCGCG  CCGCCGGGCG  TAGCGCTGGC  GCTGGGCCGC    12420

CAGGTGCGCG  TCGTCACCGA  GCGCGGCGAC  CATGGCGGCC  TGCACCGGGG  CGGGGACCAT    12480

GTGGCCGGCG  TGCTTGCGCA  CCTCCAGCAG  CGTCGCGATG  ACGGCCGGGT  CGCCGGCGGC    12540

GAAGCCCGCC  CGGTAGCCGG  CCAGGTTGAA  GCGCTTGGAC  AGCGAGTGCA  CCGCCAGTAC    12600

GCCGTGGTGG  TCGCCGCCGG  TGACCTCGGC  GTGGAGCACC  GAGCGGGTCG  AGCGCTCCCA    12660

CACGTGGTCC  AGGTAGCACT  CGTCGTTGAC  CACCAGGGTG  CCGCGCTCGC  GCGCCCACTC    12720

GACGACCGCG  CGCAGTTCGG  CGGCGTCGAG  CACCCGGCCC  TCCGGGTTGG  ACGGGGAGTT    12780
```

-continued

```
CAGCCACAGC AGGCGCGGCG CGGGGCCGTC GTAGCTCAGC GGGTCGTCCG TCCGGACGAA    12840
GGTGGCACCG GCCAGTCGAG CGCTCACCTC GTAGGTGGGG AAGGACAGTT GGGGGGCAAG    12900
GACGACGTCC CCCGGGCCCA GGCCCAGCAT GGTGGGCAGC CAGGCGATCA GCTCCTTGGT    12960
GCCGACCGCC GGGATCACGG CCTCCGGCTC GACGCTCACG CCCTCGCGGC GCAGCAGCCA    13020
GGCCGCGGCG GCGGCCCGCA GCGCGGGCGT GCCCTCGGTG GACGGGTAGC CCGGGGCGTC    13080
GGCCGCGGCG GCCAGGGCCG CGCGCACGGC CTCCGGGGTC GGGTCGACCG GGTCACCGAG    13140
CGCCAGGTTG ACCAACCCGT CGGGGTGGGC GGCCGCGCGC CTGCGGTACG GAACAGAAC    13200
GTCCAGGGG AACTTCGGCA GCCGCTCGAT CATGCCTGCG CCCCCGCCCC GACGTTGCGG    13260
GCCAGCGGCG GAGCCTGGCA GTCGGAGTCG ATGCCCAGG AGACGATCCG CTCCGGCGTG    13320
ATCCGGATCA GCTCGTCGTC GACGTGCGGC AGGATCTCCT TGCCGCCGGT CGCCAGCGCG    13380
ACGGCGGTGC CCCGGATCTC GATCCCGCGG ACGACCCAGC GCTGCGCGTC CACGATGTCG    13440
TCCACCACCA GCGACACCCG CGGATGCCCC TGCACGTGGC GGTACTTGAG GCTGCGGGCC    13500
ATGCCGCGCC CGGTCACGTC GACGGTGCCG AGCTCGGCGT TGTAGTGGAA GCCCAGCGGG    13560
ACGACGTGCG GCTGTCCCCG GCCGTCCACG GTGGCCAGGC GGGCGAGCGG CTGCGAGGCC    13620
AGGTAGGCGG CCTCTTTCGC GGTGAATGGC ATGGCTGTCC TCGGTGTCTG CGGGTCAGGG    13680
TCGGCGCCCA CGCTAGGCAG CCTGCTTCGA GCGGCCTTGG TGCCGTTCGG CCTGCTCGCG    13740
TACCCGCGCT GGACTCCGGC TCGAAGTCCG GCTGACACGG TGAGGCCGTC GTACCGGACC    13800
GAGACGGGAG GTCGCGTTGG ACTGCGATGT GGTGGTGGCG GGAGCGGGGC CGACGGGCCT    13860
GATGCTCGCC TGCGAACTGG CCCTGGGCGG AGCCCGGGCG GTGGTGGTGG AACGGCGCCG    13920
CGAGCCGGAG AAGCACTCCA AGGCCATGGG CATGCAGGGC CGCACCGTGG AACTGCTCGA    13980
ACTGCGCGGG CTGCTCGACC GCTTCAAGGA GGGCGCGGGC GTGCTGCAGG GCGGCAACTT    14040
CGCCAGCCTG GGCGTGCCGA TGCGCTTCGA GGAGTTCGAC ACCCGCCACC CGTACGTGCT    14100
GCTGGTGCCC CAACTGCGCA CCGAGGAGCT GCTCGCCGAA CGGGCCCGCG AACTGGGCGT    14160
GCGGATCGTG CGCGGCTCGG GCGTCACCGG CTTCGCCCAG GACGCCGACG GGGTCACCGT    14220
CGAGACGGAC ACGGGCCTGC TTCGGGCACG GTACCTGGTC GGCTGCGACG GCGGCGGCAG    14280
CACCGTCCGC AAGGCCGCCG GCATCGGCTT CACCGGACAG GACCCGCACA TGTACGCCCT    14340
CATCGGCGAC ATGCGCTTCA GCGGCGACCT GCCGCGCGGC GAGGGCCTCG GCCCAATGCG    14400
GCCGGTGGGC CTGGTCAACC CCGCCAAGCG GTCCTGGTTC GGCGCCTTCC AGCACCAGCC    14460
GGGCGTCTAC CGGGCCACCG TCGCCTGGTT CGACCGGCCC TTCGCCGACC GCCGCGCCCC    14520
GGTCACCGAG GAGGAGATGC GCGCCGCACT GGTCGAGCAC ACCGGCAGTG ACCACGGGAT    14580
GCACGACGTC ACCTGGCTGT CCCGCCTCAC CGACGTCTCC CGGCTGGCCG ACTCCTACCG    14640
GCTGGGCCGG GTGCTGCTGG CCGGCGACGC CGCGCACATC CACCTGCCGG CCGGCGGCCA    14700
GGGGCTCAAC CTGGGCTTCC AGGACGCCGT CAACCTCGGC TGGAAGCTGG CCGCCGTGGT    14760
CCGCGGCCAC GGCACCGAGG AGCTGCTGGA CAGCTACGGC CGCGAGCTGT CGCCCGATCG    14820
CCGACGGGTG GTGCGCAACA CCCGCACCCA GGCCGTCCTG ATCGACCCGG ACCCGCGGTA    14880
CGAGGCACTG CGCCAGACCT TCCGCGACCT GATGGCGCTG CCCGACACCA ACCGCCACAT    14940
CGCCGGCATG CTCTCCGGCT TCGACGTCGC CTACGGCGGC GGCGACCACC CTCTGGTCGG    15000
CCGCCGGATG CCGGACGCCG AGCTGATCAC CGCGGACGGG CCGCGGAGGA TCAGCGATTG    15060
CTTCGCCGGG GCCCGCGGTC TGCTGCTGCT CCCCGAACAG GGCCCGACCG CCTCGCCGCT    15120
GGCCGCCTGG GCGGACCGCG TGGACACCCT GACCGTCAAG TCGGGCGGCC CGGACCCGGA    15180
```

| | | | | | | |
|---|---|---|---|---|---|---|
| CACCGCCCAC | CTCGTCCGCC | CGGACGGCTA | CGTGGCCTGG | GCCGGCGAAC | CGGCCCGCAC | 15240 |
| CGAGGAACTG | CACCACGCCG | CGACCACCTG | GTTCGGCGCG | GCGGCCTGAT | CCCCCTCCCC | 15300 |
| CTGAGAAAGG | ACGCACGATG | ACCTCGTCCA | CCGACAGCGC | CGCCGCCCGC | GCGCGCCGGA | 15360 |
| TCGTCGCCCT | CAACACCGCC | TACTTCCAGG | CGAAGGCGCT | GCAGAGCGCG | GTCGAGCTCG | 15420 |
| GCCTCTTCGA | GCTGCTCGCC | GAGCGCTCCG | CCGGGCTCGA | CCAGATCCGC | GCCGAACTGG | 15480 |
| GCGTCCGGCA | CCGGCTGTTC | AAGGACTTCC | TGAACGCCCT | GGTCGGCCTC | GGCCTGCTGG | 15540 |
| ACGAGCAGGA | CGGCGGCTAC | CGGGCCTCCG | AGCTCGCCCG | GGAGTTCCTG | CTCCCCGGCC | 15600 |
| CCACGTACCT | CGGCGGCACC | GCCCGCCAGC | ACGCTCGGCT | GCACTACCAC | GCCTGGGCGC | 15660 |
| AGCTGACCGA | CGCGCTGCGC | GACGGCAAGG | CCAAGTCGGC | CGTGGCCGCG | CAGGGCCAGC | 15720 |
| TGGCCTACCC | CAAGCAGTAC | GAGGACCTGG | ACCGCGCCCG | GCAGATCATG | CTGCACATGG | 15780 |
| ACGCCCACAA | CGGTTTCACG | GCCGACGAGT | TGGCGCGCGC | GATCGACTGG | AGCCGGTACA | 15840 |
| CCTCCTTCGT | GGACGTCGGC | GGCGGGCGCG | GCAACGTCGC | CTCCCGGATC | GTCACCGCCC | 15900 |
| ACCCGCACCT | GCGCGGCGGG | GTCTTCGACC | TGCCGGCGCT | GCGCCCGCTC | TTCGAGGAGC | 15960 |
| TGGTGGCCTC | GGCCGGAACC | GCCGACCGGG | TGGACTTCCA | CGGCGGTGAC | TTCTTCGCCA | 16020 |
| CCGACCTGCC | GGAGGCGGAC | GTGGTGATCT | TCGGTCACGC | CTGCCGGACT | GGGCCGGTCG | 16080 |
| GGGACCGCAG | GGAGCTGCTG | CGCCGCGCCC | ACAAGGCGGT | GCGCCCGGGC | GGCCTGGTGG | 16140 |
| TGCTGTACGA | CGCCATGATC | GACCCGGAGG | AGCGCGACCC | CGAGGTCCTG | CTGCAGCGGA | 16200 |
| TCAACCACAC | CATGATCCGG | GACGAGGCCG | GGGCCTACTC | GCTGCAGGAG | GCCCGCGCCT | 16260 |
| ACCTGGAGGA | GGCCGGCTTC | ACCGTCGACC | GGATCGCCGC | CTCCGACACC | ATCACCCGCG | 16320 |
| ACCACTTCGC | CATCGGCGTC | AAGTCGGTCT | GAAGGAAAAG | GAGTTCGACA | TGACCGACAC | 16380 |
| AACCGCGGAT | CAGACGCGGC | ACGGCGACCG | GCCGTACGAC | GTCGTCATCA | TCGGCAGCGG | 16440 |
| GCTGTCGGGC | ACCATGCTCG | GCTCGATCCT | CGCCAAGCAC | GGCTTCCGGA | TCATGCTGCT | 16500 |
| GGACGGTGCC | CACCACCCCC | GCTTCGCCGT | CGGCGAGTCC | ACCATCGGGC | AGACGCTGGT | 16560 |
| GGTGCTGCGG | CTGATCTCGG | ACCGGTACGG | GGTGCCGGAG | ATCGCCAACC | TGGCGAGCTT | 16620 |
| CCAGGACGTC | CTCGCCAACG | TCAGCAGTTC | GCACGGGCAG | AAGAGCAACT | TCGGCTTCAT | 16680 |
| GTTCCACCGG | GACGGCGAGG | AGCCGGACCC | GAACGAGACC | AGCCAGTTCC | GCATCCCCTC | 16740 |
| GATCGTCGGC | AACGCGGCCC | ACTTCTTCCG | CCAGGACACC | GACTCCTACA | TGTTCCACGC | 16800 |
| CGCGGTGCGC | TACGGCTGCG | ACGCCCGGCA | GTACTACCGG | GTGGAGAACA | TCGAGTTCGA | 16860 |
| CGACGGCGGG | GTGACCGTCT | CCGGCGCGGA | CGGCAGCACC | GTCCGGGCCC | GCTACCTGGT | 16920 |
| CGACGCCAGC | GGCTTCCGCT | CGCCGCTGGC | ACGGCAGTTG | GGGCTGCGGG | AGGAGCCGAG | 16980 |
| CCGGCTCAAG | CACCACGCCC | GCTCGATCTT | CACCCACATG | GTCGGAGTGG | ACGCGATCGA | 17040 |
| CGACCACGTG | GACACGCCGG | CCGAGCTTCG | CCCGCCGGTG | CCGTGGAACG | ACGGGACGAT | 17100 |
| GCACCACATC | TTCGAGCGCG | GCTGGATGTG | GATCATCCCG | TTCAACAACC | ACCCCGGGGC | 17160 |
| CACCAACCCG | CTGTGCAGCG | TCGGCATCCA | GCTCGACGAG | CGCCGCTACC | CCGCCCGGCC | 17220 |
| GGACCTGACG | CCCGAGGAGG | AGTTCTGGTC | CCACGTGGAC | CGCTTCCCGG | CGGTGCAGCG | 17280 |
| GCAGTTGAAG | GGCGCCCGCA | GCGTGCGCGA | GTGGGTGCGA | ACGGACCGCA | TGCAGTACTC | 17340 |
| CTCGAGCCGG | ACGGTCGGCG | AGCGCTGGTG | CCTGATGTCG | CACGCGGCCG | GCTTCATCGA | 17400 |
| CCCGCTCTTC | TCCCGCGGCC | TGTCCAACAC | CTGCGAGATC | ATCAACGCGC | TGTCCTGGCG | 17460 |
| GCTGATGGCC | GCGCTGCGCG | AGGACGACTT | CGCGGTCGAG | CGCTTCGCCT | ACGTGGAGGA | 17520 |
| ACTGGAGCAG | GGCCTGCTGG | ACTGGAACGA | CAAGCTGGTC | AACAACTCCT | TCATCTCCTT | 17580 |

```
CTCGCACTAC  CCGCTGTGGA  ACTCGGTCTT  CCGGATCTGG  GCCTCGGCCA  GCGTGATCGG    17640
CGGCAAGCGC  ATCCTCAACG  CACTGACCAG  GACCAAGGAG  ACCGGCGACG  ACAGCCACTG    17700
CCAGGCGCTG  GACGACAACC  CGTACCCGGG  CCTGTGGTGT  CCGCTGGACT  TCTACAAGGA    17760
GGCCTTCGAC  GAGCTCACCG  AGCTGTGCGA  GGCCGTGGAC  GCCGGGGACA  CCACGGCCGA    17820
GGAGGCCGCG  CGGGTGCTGG  AGCAGCGGGT  CCGCGAGTCG  GACTGGATGC  TGCCGGCCCT    17880
GGGCTTCAAC  GACCCCGACA  CCCACCACAT  CAACCCGACG  GCGGACAAGA  TGATCCGGAT    17940
CGCGGAGTGG  GCCACCGGTC  ACCACCGCCC  GGAGATCCGT  GAGCTGCTGG  CCGCCAGCGC    18000
CGAGGAGGTC  AGGGCGGCGA  TGCGGGTCAA  GCCGTAACAC  GAGGGGCAAC  GGGCAGCAGC    18060
GTCCGCGGGA  CGGCTGCTCC  CGGACGCGGG  CCTCGCCGTT  CGCCGCACGC  GGGCGGGCTC    18120
AGCCCTCGGC  CGCCAGGGTC  AGGGCGGCCG  TCCGCGGATC  CTCCTCCACC  GGCCAGCGGG    18180
CGTAGGAGCG  CGCGCAGTAC  ATCAGCGGGC  TGGGCACCCT  CGGGCCGGGG  CCCGCCGGCC    18240
CACCACCGCG  CCGATCACGA  TGGTGTGGTC  GCCCGCTGTC  GAGGGCCGCG  GCCGACCCGG    18300
CACTCGGCGT  GCGCGACGAC  GTCGGCCGAC  AGTGACCGGC  ACGCCACCGG  CGCTGCCCGG    18360
CTCCCACCGG  GACGTCCCGG  AAGCGGTCGT  CCACGGGCGC  GGCGAAGCGC  GGGGACGTGG    18420
ACTCCCCCTC  CGCCGCGCAG  CACGTTGACG  GCGAACTCGC  CGCGCTCCAG  GAGGGCCTTC    18480
AGCACCCGGC  TGTCGCGGTT  GATGCAGACC  CAGCAGCAGG  GGCGGGGCCT  TGGAGACGCT    18540
GCAGGCGGCC  GAACAGGTCA  ACCCGTACGG  CTCCCGTCC   GGTCCCAGGG  TCGTCACCAC    18600
GGTGACCCCG  GTCGGCAGGG  CGCCCATGAT  CGACAGGAAG  GTGTCGCCGT  CCACCAGGCC    18660
GGGAGCCAGG  TCCAGCGGCA  GGGACAGGGG  TTCGGGGGGC  ATCGGTCCTC  CACTCTCGGC    18720
GGGTCGGTGT  CCCCATGCTC  GCGGGGCGCC  TTCGAGCCGG  CGCCGGGCCG  TCGTCGGGCC    18780
CTCCGCGCAC  GCGAACGGGC  GCGCAAACGG  GCGCGCGAAC  GGGCGCGCGC  GAGGGCGCGC    18840
GGACGCGGCC  GGAGCCGGAG  CGGAAAAGCG  CGTACCCCCG  GCACGGGGGT  GACCGGGGGT    18900
ACGCGCGGTT  CAGGGGGTCG  CGTGCGCGCG  CTCACTCCTC  GTCGCGCAGT  TCCCGCAGCG    18960
GGAAGGTGAG  CAGGAAGCCC  ACCGCAAGGA  TCAGGCCGCC  GACCAGGAAC  ATCGTGTCGA    19020
AGCCCGAGGT  GAAGGCGTCG  ACCGCCGAGG  CGCTCAGGCC  GCCGGTGGAG  TCCGGGTCGG    19080
AGAGCGCACG  GCGCACGGCC  TCGTCCGGGT  CGGCCCCGTC  GAGCCTGCCG  GCGGCGACGC    19140
CGAACAGCAC  CGACATGAAG  ACGGCGGCGC  CGCTCGTGCC  GCCGAGCTGG  CGGAACAGCC    19200
CGGAGGCGGC  GTTGGCCACG  CCCAGCTCGG  ACTTGGGCGC  CGAGCTCTGG  ATCGCCAGGG    19260
TGATGACGGT  CTGGGAGAGC  CCGATGCCGA  AGCCCAGCCA  GGCCGCGATC  ACCACGATCA    19320
CCGCGAGCGG  GGTGTCCGCG  CCCGCGGCGG  AGAGCGACAG  CAGTGCTCCG  GCCATCGAGC    19380
CGAGGCCCAC  GATCGCGGGC  TTCTTGTAGC  GGTTCCACTT  CTTGATGATC  TTGGCGCAGA    19440
TCGTCTGGGA  GACGATCGCC  CCGGTCATCA  CCGGGATGAT  CACCAGTCCG  GCGACGGTGG    19500
CACTGCGCCC  CTGCACCAGC  TGCAGGAACA  GCGGCAGGGT  GGAGACCGTA  CCGAAGATGC    19560
CGACGCCGAT  GGTGAAGTTG  ACGGCCGTGG  TCATCGTGAT  GCCACCGCGC  CGGAACAGCC    19620
GTAGCGGGAC  CATCGCCTCC  AGCCCGCGGG  CCCGTTCGGC  GAGCACGAAC  AGCACCAGGC    19680
CGATCAGCGA  GACGGCGAAC  AGCGTCAGCG  AACGCGCCGA  TCCCCAGCCC  CAGTCGAGGC    19740
CCTCCTCCGC  CACGATCAGC  AGCGGCACCA  GGCAGAGCGC  CAGGGTGAGC  GCCCCCCGGA    19800
AGTCGATCGG  GTGGTCCACC  CTGCGGTGCG  GCAGGTTGAG  CGCCTTGCGC  ACGCTGAGCA    19860
GCGCCACGAG  ACCGAGCGGC  ACGTTGATCA  GGAAGGCCCA  GCGCCAGCCG  GTCACCCCGA    19920
GGATCTCGCC  GGCGCCCGCG  AACAGGCCCC  CGACGAGCGG  GCCGAGCACA  CTGGCCGCCA    19980
```

```
CCCAGGCCAT  CATCAGGTAC  GAGAAGTAGC  GCCCGCGCTC  GCGCACCGGG  GCGAGGTCGG  20040
CGATGACGGC  CGTCGGCAGC  GACATCAGCC  CGGCGCCGCC  GAAGCCCTGG  AGGACGCGGG  20100
CGATCGCCAG  CGTCTCCATC  GAGTTCGCCA  TCGCGCAGGC  CGCCGAGCCG  ACGATGAAGA  20160
CCGCGATCGC  CGCCAGATAG  AGCGGCTTGC  GGCCGTAGAT  GTCGGACAGC  TTGCCGTAGA  20220
ACGGCATCGC  GATCGTGGAG  CTGACCAGGT  AGCCGGTGAT  CACCCAGGCC  TGGACGGTCT  20280
GGCCGTGCAG  TTGGTCGCCG  ATCGTACGCA  GCGCGGTGGA  GACGATCGTC  TGGTCGAGTG  20340
CGGCGAGCAG  CACGGCCAAC  AGGAGCCCGG  ACAGCGCGGT  GATGATCTGG  CGGTGAGTGA  20400
AGCCGGCGGG  GCCGCCGGCC  TCGTCCGCGA  CGGCCTCGCC  GGTCTGCGAG  GTGGCGTTCG  20460
CCATTCCCAT  TTCTCCCACC  GAATTCGACA  AGGTCTTGTC  GAACTGAGCG  TAGTGGGCTA  20520
CCGTGGCGGA  ATGACAAGTT  CTTGCCGAAA  TCCCGGCCCG  GACGAGGCTA  GGCTGGCCGT  20580
GGAGAGCCTG  CGATTAGGCT  GCCCCCATGA  CCGATCTCTC  CCCCGCGGCC  GAGACCTTGA  20640
GTGACATCAC  CACCGAACTG  TTCGCCGTCA  ACGGAGCCCT  GCTGCGCGCG  GGCGACGCGC  20700
TGTCCGCCCG  CTTCGGGCTC  ACCTCCGCGC  GCTGGCAGGT  CCTCGGGCTG  CTGGCCGAGG  20760
GGCCGCAGAG  CGCCGCCCAC  CTGGCGCGCG  AGCGGGCTGC  GCCGCCAGCC  GTCCAGCAGA  20820
CCGTGGTGAA  GCTGGTCGAG  GAGGGCCTGG  TCAGCACCTC  CCCCAACCCG  GCCGACCGGC  20880
GGGCCCCGTT  GGTCTCGCTG  ACCGCCAAGG  GCACCGACGC  CCTCGCCCGG  ATCGAACCCG  20940
CCGAACGCCT  GTGGATGGAG  CACCTCGCGG  GCGGCCTGGA  TCCGGACGAC  CTGACAGGCC  21000
ACGCTGCGGC  TGCTGCGTGG  CTTCGGGCGG  TCCTGGCCGA  GGGGCTGCCC  CCGACGGCGG  21060
TCGGCGGCGC  GGACGCCGCC  GACGTCACAG  GTCCAGCGTG  ACCTCGTACT  CGGCGAGCCA  21120
GGAGTTGAGC  CACAGCACCA  GCTCCAGACT  GCCCCGGTCG  TAGGGCCGGC  TCACCGCCCC  21180
GGTCGGACGG  GCAGCCGCGG  CCAGGGCCCG  CTCGCGGTCC  AGCAGCGGCA  GCACCGGAGC  21240
GTCCGGATCG  GCGAGCACCC  CGGCCAGTTC  GGCCCGCAGG  GCGCCCTCGT  AGCCCGGATC  21300
CTGGGTCGCC  GGGTACGGGG  TCTTCACCCG  CTCGACCACC  GAGCGCGGCA  GCAGGTCGGC  21360
CACCGCCGCC  CGCAGCAGGC  TCTTCTCCCG  GCCGTCGAAA  CTCTTCATCT  CCCAGGGCAC  21420
GTTGAAGACG  TACTCCACGA  GCCGGTGGTC  GCAGAACGGC  ACCCGCACCT  CGAGGCCGAC  21480
CGCCATGCTC  ATCCGGTCCT  TGCGGTCGAG  CAGGGTCTGC  ACGAAGCGGG  TCAGGTTCAG  21540
GTGACCGATC  TCGCGCATCC  GCCTCTCGGG  CGCCGACTCA  CCCGGCAGCA  CCGGCACTTC  21600
GGCGAGCGCC  TCGGCGTACC  GGGCCGCCCG  GTAGCCGTCC  AGGTCGAGCT  TGTCCAGCAG  21660
ACCCGCCTGG  AACAGCGAGC  TGCCGCCGAA  GTAGCGCGCC  GAACCCGGGG  TGAGCCACGG  21720
GAAGGTGGCC  GCCCGCAGGG  CCAACGGGTT  GCGGAACCAC  CGGTAGCCGC  CGAAGAGTTC  21780
GTCCGCGGCC  TCGCCGGACA  GCGCCACCGT  GACGTTCTCC  CGCACCGCGC  GGAAGAACAG  21840
GTAGAGCGAG  GGCCACATGT  CGCCCCAGTA  CGCGGGCGGC  AGGTCGGTGG  CGCGCAGCAC  21900
CGCGGAACGC  ACCGCCGGGT  CCGACAGGCC  GGGGCTGTCC  AGCAGCACCT  CCAGGTGGTC  21960
CGCTCCGACG  TGCCCCGCCA  GCTCGCGCAC  GTACGGCGCG  TCCGCCTCCC  GCCGGACGGC  22020
GTCGGAGGCG  AAGGCGTCGG  CGGCGCCCCG  GAAGTCCACC  GAGAAGGAGC  GCACCGGCCC  22080
GCTGCGGGCG  GCCAGCGCCG  TCACGGCCGA  CGAGTCCAGG  CCGCCGGAGA  GCAGCGTGCC  22140
CAGCGGGACG  TCCGAGACCA  GCTGACGGGT  GACGGTGTCG  GCGAGCAGGT  CACGGACGGT  22200
GCCGATGGTC  GTCGGCAGGT  CGTCGGTGTG  CTCGCGGGCC  TCCAGCCGCC  AGTACGTCTG  22260
CCGGCGCACC  CCGCCGCGCC  CCACCCGGAC  GAGCTGACCC  GGACGGACCT  CGACGAGCCC  22320
GGAGAAGACG  GCCGCCTCGG  GCGTCTTCAC  CATGTCCAGC  ACCTCGCACA  GCCCGTCCGG  22380
```

```
GCCGACCCGG  CGGGACAGGG  TCCGGTCCGC  CAGGACGGCC  TTGGGCTCCG  AGCCGAAGCG   22440
CACGCCGGCG  GCGGTCGGCC  AGTAGTAGAG  CGGCTTGACG  CCCATCCGGT  CGCGGACCAG   22500
CAGGAGTTCC  TCGCTGTGCT  CGTCCCAGAC  GGCGAAGGCG  AACATCCCGT  TGAGCCTCTC   22560
GACCAGCGCG  GCGCCCCACT  GGAGGTAGCC  GCGCAGGACG  ACCTCGGTAT  CGCAGGACGT   22620
CCTGAACCGG  TGGCCGTGCG  AGGTGAGTTC  GGCGCGCAGC  TCACGGAAGT  TGTAGATCTC   22680
GCCGCTGAAG  GTGATCGCCG  CGCCGCGGCC  CTCGTGTTCC  GCGGTCATCG  GCTGCCGGCC   22740
GTGCTCGGGG  TCGATCACCG  ACAGGCGCCG  GTGACCGAGC  CCGGCCGCGC  GGCCGAACCA   22800
GAGGCCCTCG  GCGTCCGGCC  CCCGGCAGGC  CATGGTGTCG  GTCATCGCCT  GGAGCAGGTC   22860
CCGGCGGTGT  TCGGCCGGGG  CGTCGTAGTC  GACCACCCCC  ACGATTCCGC  ACATGCTCAG   22920
CCGGCCGTGG  CGAGACCGAG  GTTGACCGCG  TCCAGGAGCA  TCCGCGGCGT  GGTGGCCTCC   22980
ACCACGGTCT  CGTCGGGCAG  GGTGATGCCG  CGCTCGCGCT  CGATGGTGTT  GAGGGTGTTG   23040
AACAGGGCGA  GCGAGTCGTA  GCCGAGGTCG  GCGAAGGGGA  CGTCCAGGAT  GTCGTCGAGG   23100
GCGACGCCCT  CGTCGGCTCC  GGCAGCCTCC  TTCAGCGCGG  CGATCAGGTC  GTCAAGGGTG   23160
AACTCTGCCA  TGGCTGTTCC  TCACATCGGT  GGGTCGGTCT  GTCGAATCCG  GAAGGTCAGG   23220
CGGGCGGTCG  GCCGGCCCGG  TCAACTGGTC  AGTACGAGAG  CGCTGTTGAA  GCCGCCGTGG   23280
CCGCGGGCGA  GGACCAGCGC  GCTGCCCAGC  CGGGCCGGCC  TCGGCGGTCC  CAGCACCAGG   23340
TCGAGGTCCG  GGTGGGCCGG  CCGGCCGATG  TGCACGGACG  GCGGGATCAC  CCCGTCCCGC   23400
AGGGAGAGCA  GCGCGGCCGC  GACGTCCAGC  GGGGCGCCAC  CGGCCAGCAG  CCGGCCGGTC   23460
ATCGTCTTGG  GCGCCGTCAC  CGGCACCCCG  CGCGGGCCGA  ACACCGCGCC  CAGCACCTCG   23520
GCCTCGGCGC  GGTCCTGCTC  GGCCACACCG  CTGGCGTCGG  CGAAGACCAC  GTCGACGTCG   23580
GAGGGGCCGA  TCCCGGCGTC  GGCGAGCGCC  GTGTCGATCG  CCCGGCGCAG  CCCGGGCGGG   23640
CGCCCGGAGC  CGGGTCGGGG  GTCGAAGGTG  GCCGCGTAGC  CGGCGATCCG  CCCGTAGTGG   23700
CGGTGCTGCC  CGCGCTCGGC  GGCGCCGTCC  GGGGTCTCCA  GCACGAGCAG  TGCGCCGCCC   23760
TCGCCCGGCA  CCCCGCCGGA  GGCGTCGGCG  TCGAAGGGCA  GGAAGGCCCG  CTGCGGGTCC   23820
CGCCGGGGGC  TGACCGTGCC  GCTGCGGCTG  AGGCAGAGCC  ACGACCAGGG  GCAGAGCGAG   23880
CCGTCCACCG  CGCCGGCCAG  CATCAGCGCG  GTGCCCTCGC  GCACGTGCCG  GCGGGCCTTG   23940
GCCAGCGCGT  CCAGGCCGCC  CGCCTGCTCG  GCCACCAGGG  CCGAACCGGG  GCCGCGCATG   24000
CCGTGCCGGA  TCGAGATCTG  CCCGGTGTTG  ACCGGGTAGA  ACCACGCGAA  GGACTGGTAG   24060
GCGCTGACGT  AGGCCGGGCC  CTTGCTCCAC  AGCGCCTGGA  GTTCCTTCTG  GCCGAACTCG   24120
AAGCCGCCGG  CCGAGGCGGC  CGTCACGACG  CCGGCGGAGA  AGTCCGGCAT  CGTCGTCGGG   24180
TCCGCCCCCG  CGTCGGCGAG  CGCCTCCTCG  GCCGCGACCA  GGGCCAGCCG  CGTCATGTGG   24240
TCGGTCTGCG  GCAGCAGTCG  GCCCGGCAGG  TGTTCCTCCG  GCGTGAAGTT  CACCTCGCCG   24300
GCCACGTGCG  CCCGGTACCC  GGTGGAGTCG  AAGCGGGTCA  GCGGCCCGAG  ACCGGACCGG   24360
CCCGCCAGTG  TGGCGTCCCA  GTACTCCGCA  ACGCCCAGC   CGTTCGGTGC  CACCACGCCG   24420
ATCCCGGTCA  CCACGACGTC  GGTCATCCCC  GGCTCCACTC  CGGCTCGGCG  AGCACGATCG   24480
CGCTCTGGAA  GCCGCCGAAG  CCGCTCGCCA  CGCTGAGCAC  CGTGCGCACC  CGCTGTTCCC   24540
GCGCCACCAG  CGGCACGTAG  TCGAGGTCGC  ACTCGGGATC  GGGCACGTGC  AGGTTGGCCG   24600
TGGCGGCAC   CACCGAGTGC  TCGATCGCCA  GCGCGCTGGC  GGCGAACTCC  AGGGCGCAGA   24660
CCGCGCCCAG  CGAGTGTCCG  ATCATCGACT  TGATCGAGCT  GACCGGCACC  CGGTAGGCGT   24720
GGTCGCCCAG  GCTCTTCTTG  AACGCGGCGG  TCTCGTGCCG  GTCGTTCTGC  TTGGTCGCCG   24780
```

```
AGCCGTGCGC GTTGACGTAG CCGACGTCCT CGGGGTTCAT CCGGCTGCGG TCGAGCGCGA   24840
CCCGGATAGC CTCGGCCATC TCGTTCCCGT CGACCCGCAG CCCGGTCATG CTGTAGGAGT   24900
TGCAGCGCCC GGCGTAGCCG GTGACCTCGG CGTAGATGTG CGCGCCGCGC CGGATCGCGT   24960
GCTCCCGCTC CTCCAGCACG AACATCGCCG CGCCCTCGCC GAGGGCGAAG CCGTTGCGGG   25020
TCAGGTCGAA GGGGCGCGAG GCGCTCTCGG GTTCGTCGTT GCGCGGGGTG GTCGCCTTGA   25080
TCGCGTCGAA GCAGGCCACC GTGATCGGGG AGATCGCCGC GTCCGAGGCG CCGGCCAGCA   25140
TCACGTCGGC CGCGTCGTCG CGGATCAGGT CGCAGGCGTG CGCGATCACG TCGATCCCCG   25200
AGGTGCATCC GGTCGACACC ACGCCCACCG GACCCTCCGC CTCGACCAGC CAGGCCAGTT   25260
CGGTGGCCAT CGAGGACGGG ACGAAGTAGT CGTAGAGGTA CGGGACGCCG TGCGCGTCGT   25320
CGACCAGCCG CTTGCGGCCC TCGTCGCTCA CCACGGCGAA CTCGCGGTCC AGACTGATCG   25380
TCATCCCACA GGCGGTGCCG GCCATCACCC CGGTGCGGAT CGGGTCGTTG ACGCCCGACA   25440
CCCCCGAGTC GTCCAGCGCC TCGCGCGCGG CGACCACCGC GAACTGCGCG GTGCGGTCCC   25500
ATTGACGGAT CTGACGCTGC GTCAACCCCG CGGCCTGCGG GTCGAAGTCG CACTCGGCGG   25560
CGACCCTGGA CCGGAACGGC GAGGGGTCGA AGGTCGAGAT CGTCCGGGTC GCGGTCCGGC   25620
CGGCCGTCAG CAGCTCCAG AACGCCTTGG TGCCCACCTC GCCCGGTGCC ACCACGCCGA   25680
TCCCGGTGAC CACCACGCGC CGGCGGCCGT CGTCAACTCC CACCACTGCT CCCCCTGTCG   25740
ATCTCCCCGT GCGTGTCCGG CGTCATGCCC TGACCTCCTG TCCGTGCGGC CCGTCCGCGG   25800
GCTCGGGCGG GCGGGGACTT GAGCCGGATC AGATCGTCCT GGCAGGCGTT CGCGGCGGCT   25860
TCGAGCCGCC GTCCACGCGC CTCCGGCCCC CGCCTTCCCG CCGCGGCGGG AAGAGCCGCA   25920
CGCACGACGG CGGCGGCGCC GCACCCACGG CGGCGGGAAG ACGACGCGAA CCGGCGTCGA   25980
AGGGCGCCCC CTAGCGTCTG GCCGCATGGA CATCGACACC GACATCTGCG TGGTCGGCGG   26040
CGGCCCGGCC GGGCTGACCC TCGCCCTGCT GCTGGTCCGC TCGGGCCTGC GCGTCACCGT   26100
GCTGGAACGC AGCCGCTCCC TGGACCGGGC CTACCGCGGC GAGATCCTCC AACCCGGCGG   26160
CCAGGCCTTG CTGGACGAGC TGGGCGTGCT CGGCCCGGCC CGGGCGCACG GCGCCGTCGA   26220
GCACGACCGC TTCCTGCTCG AGGAGCACGG ACGCGTCCTC ATCGACGGCG ACTACCGGCG   26280
CCTGCCCGGG CCGTACAACT GCCTGCTGAG CCTGCCCCAG CGGCACCTGC TGACCGAACT   26340
GCTCGCGGCC TGCGAACGCC ACGAAGGATT CCGCCAGTTC GCGGGCGCCA AGGCCACCGC   26400
CCTGATCGAG GAGGGCGGCT TCGTCCGCGG TGTGGTCGCG GGCGGCGCGG GCGGCTCCCC   26460
CGACCGGGTG GTGCGGGCCC GCTGCGTCGT CGCCGCGGAC GGCCGCTTCT CCAAGGTCCG   26520
CTCGCTCGCC GGGATCGGCT ACCGGCGCCA GGAGCTGTTC AGCCAGGACG TCCTGTGGTT   26580
CCGGCTGAGC GCACCGCCGC GCACGGACAC CCGACGCCCG TGCGACGTCC GGGTCTTCCG   26640
GGCCGGCGGC AATCCGGTAC TCAGCTACCG CTCGGTGCCC GAGGCGCTCC AGCTCGGCTG   26700
GACCCTCCCG CACGGCGGCT TCCGCAAGCT GGCCGACCGC GGCATCGGCC ACATCGTCGA   26760
CCAACTCGTC GACGCCGCAC CGGAGTACGC CGACCTGATC CGCCAGGAGA TCACCGGCTT   26820
CGGCGACGTC TCCCTGCTGG ACGTCTTCTC CGGCAGCGCC GAGCACTGGG TGCGCGACGG   26880
CCTGCTCCTG ATCGGCGATG CCGCCCACAC CCACAGCCCG ATCGGCGCCC AGGGGATCAA   26940
CCTGGCCGTC CCGCCGCCGC GTCGGGCCCA CCCGGTGCTG GTCGAGGCCG TCCGCGGCGG   27000
CGACGCGGCG CGGCCCGGCT CGCCCCGTAC GAACGGCAAC GCCGCCCCG AAGTGGAACG   27060
GATCACCCGG ATCCAGCAGG TCCAGAGCCG CATGATGCTC TCCACCGGGC GCATCTCCTC   27120
CACGGTGCGC CCCCGGGCCG CGGCGCTGGT GTCCAGGACC CCGCTGTACG GGGCCGTGCT   27180
```

```
GCGCCGGATC GCCTTCGGCA CCGCGCCCGT CCGGCTGCGC GCCGATCTGC TCGCCGGGGC    27240
GGGGCGGTGA GCGGCGGGGC AGCGATCGCC GCCGGCGACT CGGCGACGGC GAGCGGGGTG    27300
CTCCTCGCCC TCGCCGTCGT CCTCGCCAGC GCGTTCGTCT GCGGCCGGCT CGCCGCCCGG    27360
GTGCGCCAGC CCGTCGTCAT GGGGGAGATC GTCGGCGGGG TGGCCCTCGG CCCCAGCCTG    27420
CTCGGGCTGC TGCCGGGGCA CCTGGACGCC TCACTGTTCC CGGCGGAGGT CCAGTCCTAC    27480
CTGCGGGTGC TGTCCCAACT GGGCCTGGTG CTCTTCATGT TCACCGTCGG CCTGCGCTTC    27540
GACGTCGGCC ACCTGCGCGG CGCCGGGCGC CGGGTGACAG CGGTGTCGCT CAGCTCGGTG    27600
GCCCTGCCGT TCGCGCTCGG CGTGGGGCTC GCGGTGCTGC TCTACCCCTG GTTCGACAAG    27660
GCCCAGTTGA GCACCGACGG GAGGCTCGGC CCGGCCCTGT TCCTGGGCGC GGCGATGTCC    27720
ATCACGGCCT TTCCCGTCCT CGCCCGGATC ATCGCCGAGC GACGGATGCA GCACGACCCG    27780
CTCGGCAGCC TGTCATTGGC CTGCGCGGCC TTCCAGGACT TCCTCGCCTG GTGCGCGCTG    27840
GCGGTGGTGG TGGCGGTGGT GGAGGCCAAG GGCCTCTGGT CGCTGGGACG GCTGGCGCTC    27900
GACACGGCGG TGGTGGTCCT GGTGCTGGTC GGCGTCGTCC GCCCGCTCCT CTCCCGGCTG    27960
CTCGCCCCCG GCCGGCGCCG TCCCCTCCCC CGGCCGTGGA TCCACGCGGT GCTCGTCACC    28020
GGCACCCTGG TCACCGCCTG GGTCACGGCC GAGATCGGCC TGGACGCGGT GTTCGGGGCG    28080
TTCATGTTCG GTGCGGCGGT GCCCCGGGAC CGGATCGAGG CGATCGCGCC CGACGTCCCG    28140
GAGCAGATCG AGCGGGCGGG TCTCCTGCTG CTGCCGGCCT TCTTCGCGGT GACCGGCCTC    28200
GCCGTCGACC TCACCGGCCT CGGGCTGCGC GGCCTGGCCG TCGTGGCGGC GGTGCTGGTG    28260
GCGGCCTGCG CCGGCAAGTT CGTCGGTGCG GTCGCCGCCG CCCGGGCCAC CGGCTCGAGC    28320
CGGCGCGAGG CGCGGGTGCT CGGCATCCTG CTCAACGCCC GGGGCCTGAC CGAGCTGGTC    28380
ATCCTCAACG TGGGCCACCG GCTCGGGGTG ATCGACACCC GGATGTTCAC CGCCATGGTG    28440
GTGATGGCCC TGGTCACGAC GCTGATGACG GGGCCGCTCC TGGAGCGCCA CACGGCGGGC    28500
TCCGCCGGAT CCGCCACGCT CCCGGACCCG GCGCCCGAGG CCGCACAGGC CTCGCGGACA    28560
ACCTCCTGAT GGCGGGCCGG CCACGACCTC CGGGGGGCGT GCCCCTCACG GCGGCTCCGT    28620
CCACCCGGAG ACCCGGCGCA GCCGCGACTC AGCCGCCGCT CGACCGGGCT GAGCGGAACG    28680
TCGGGGCGCA GCCGCTCCGG GTGCCCCGAC GGTGGCCCGC CCCCGGCAGG GCCGCCCGGC    28740
TCGCCGGGCG CCGGACCGGC CCGGGCTGCG GCGGCGGGGC CACGTAGCCG GCCATCTGCC    28800
CCAGCGCCGC CAGTCCGCGC AGGAGCACGG CCAGCAGATC GAGGAGCCGT TCGTTCGGTT    28860
CGCACATCCG CCGAGCATGG CGACCGGTCC TGAAGCGCGG TTCGAGCGGT ACGGGAGGGG    28920
CGCCGGGCAC GGCGGAGAGG ACAGCCCGGC ACCCTCGGAA CCGCTGGAGC ATGACCACGG    28980
CGCCGTCGGA GCTGCGGGTG CCCGTCACAC TGACGATCCG CCGCAGGAGG GTCGGGCGTG    29040
TCCGAGGGTT CCCGCCGGAC CGGCCCCGAG CCTCACTGGT ACCGGTAGGT GGCGGCCACC    29100
GCGAGGTGGT CGCTGCCGTC CCGGGGCAGG GTGCGGGAGT CCACCGGCTT CAGCCCGCCC    29160
TTGCTCATGA TCTGGTCGAT CCGCGCCATC GGGAACGCCG CGGGCCAGCT GAAGCCGAAG    29220
CCGTCCCCGG CCGCGCCCTG GGCCGAGCGC ATCTGCGAGG TGACCGGTGC CAGGCTGCGG    29280
TCGTTCATGG TGCCGTTGAG GTCGCCGAGC AGCAGGACCT TCTTCACCGG CTCGGCCTGG    29340
ATCGCGTCGC CGAGCGCCTG GGCGCTGACG TCCCGCTGGT GGGCGGTGAA GCCGCTCTCG    29400
GCCTTGAGCC GGACGGACGG CAGGTGCGCG ACGTACACCG CGACCGGGCC CTGGGGGGTG    29460
GTGACCCGGG CCCGGAAGGC CCTGGTCCAA CCGATCTTCA GGTCCACCGA GGAGACCTCG    29520
CCGATCGGGT ACTTCGACCA GAGTCCGACC GTCCCCTCCA CCGTGTGGTG CGGGTACGCC    29580
```

-continued

| | | | | | | |
|---|---|---|---|---|---|---|
| CCGGCGAGCC | CGGTCTCGTA | CGACCGCAGC | TGGTTGCCGG | CCAGTTCCTG | GAGCGCGACG | 29640 |
| ATCTGGGCGT | CCGAGGCGAC | CAGGCCGCGG | ATGGTGCCCG | GCACGTCGGT | GTTCCCGGCC | 29700 |
| TCGACGTTGT | GGGTGACCAC | CGTCCAGTCG | CCGGTGCCGC | CGCTCTTGTC | GGACACCAGC | 29760 |
| CCGCCGAACA | GGTTGGCCCA | CAGCACGGCG | GGCACCAGCA | GGGCGAGCAG | CGCGGTGGCG | 29820 |
| GAGCGGCGCA | GCAGCGCGGG | CACCAGCAGC | ACCGGGACGG | CCAGGCCGAC | CCAGGGCAGG | 29880 |
| AAGGTCTCCA | GCAGGCTGCC | GAGGTTGCCG | ACGCTGTTCG | GCATCTCGGC | GTGGAAGGCC | 29940 |
| AGCAGCACCG | CGGTGAGCAG | GGCCAGCAGG | GCGATCGGCC | AAGTGGGCGG | CCGTCGGGAT | 30000 |
| C | | | | | | 30001 |

What is claimed is:

1. A combination of two plasmids for cloning the nucleic acid molecule which encodes the proteins of the biosynthetic pathway of tetracycline, chlortetracycline, 6-demethylchlortetracycline, 6-demethyltetracycline, 7-chloro-5a,11a-dehydrotetracycline or 2-decarboxamido-2-acetyltetracycline, wherein said plasmids have characteristic structures in which one plasmid contains an origin of replication for replication in a host cell, an antibiotic resistance gene that is expressed in an actinomycete and at least three tandem cohesive end sites; and the second plasmid contains an origin of replication for replication in an actinomycete and at least three tandem cohesive end sites.

* * * * *